(12) United States Patent
Kukla et al.

(10) Patent No.: US 7,276,510 B2
(45) Date of Patent: Oct. 2, 2007

(54) HIV REPLICATION INHIBITORS

(75) Inventors: Michael Joseph Kukla, Maple Glen, PA (US); Donald William Ludovici, Quakertown, PA (US); Robert William Kavash, Glenside, PA (US); Bart Lieven Daniel De Corte, Southampton, PA (US); Jan Heeres, Vosselaar (BE); Paul Adriaan Jan Janssen, Vosselaar (BE); Lucien Maria Henricus Koymans, Retie (BE); Marc René de Jonge, Tilburg (NL); Koen Jeanne Alfons Van Aken, Kortriik (BE); Alain Krief, Namur (BE); Ruben Gerardus George Leenders, Nijmegen (NL)

(73) Assignee: Janssen Pharmaceutica, Inc., Beerse (BE)

( * ) Notice: Subject to any disclaimer, the term of this patent is extended or adjusted under 35 U.S.C. 154(b) by 315 days.

(21) Appl. No.: 10/275,931

(22) PCT Filed: May 3, 2001

(86) PCT No.: PCT/EP01/04991

§ 371 (c)(1),
(2), (4) Date: Nov. 8, 2002

(87) PCT Pub. No.: WO01/85700

PCT Pub. Date: Nov. 15, 2001

(65) Prior Publication Data

US 2003/0171374 A1    Sep. 11, 2003

Related U.S. Application Data

(60) Provisional application No. 60/202,472, filed on May 8, 2000.

(51) Int. Cl.
| C07D 239/46 | (2006.01) |
| C07D 239/48 | (2006.01) |
| A61K 31/505 | (2006.01) |
| C07D 401/12 | (2006.01) |

(52) U.S. Cl. .................. 514/272; 514/275; 544/321; 544/323; 544/330; 544/331; 544/332

(58) Field of Classification Search ............. 544/321, 544/323, 330, 331, 332; 514/272, 275
See application file for complete search history.

(56) References Cited

U.S. PATENT DOCUMENTS 4,659,363 A * 4/1987 Hubele et al. .............. 514/272
5,332,745 A * 7/1994 Carter et al. ............... 514/275
6,878,717 B2 * 4/2005 De Corte et al. ........... 514/269

FOREIGN PATENT DOCUMENTS

| EP | 0270111 A | 6/1988 |
| EP | 0588762 A | 3/1994 |
| EP | 0795549 A | 9/1997 |
| EP | 0834507 A | 4/1998 |
| EP | 0945443 A | 9/1999 |
| GB | 854011 | * 11/1960 |
| GB | 1132244 | * 10/1968 |
| WO | WO9118887 A | 12/1991 |
| WO | WO9510506 A | 4/1995 |
| WO | WO9719065 A | 5/1997 |
| WO | WO9841512 A | 9/1998 |
| WO | WO9931073 A | 6/1999 |
| WO | WO9950256 A | 10/1999 |
| WO | WO 0039101 A | 7/2000 |

OTHER PUBLICATIONS

Karp et al., CAPLUS Abstract 100:139059, 1984.*
Pfleiderer et al., CAPLUS Abstract 75:88577, 1971.*
van Heezwijk et al., PubMed Abstract (Antivir Ther 6(4):201-29) Dec. 2001.*
Marcus et al., PubMed Abstract (Intervirology 45(4-6):260-6) 2002.*
Miles, Medline Abstract (Community Pract vol. 78, Issue 8, pp. 292-294) Aug. 2005.*

* cited by examiner

Primary Examiner—Deepak Rao

(57) ABSTRACT

This invention concerns HIV replication inhibitors of formula (I)

the N-oxides, the pharmaceutically acceptable addition salts, the quaternary amines and the stereochemically isomeric forms thereof, provided that when Q is halo then Z is N; or when Q is polyhalo$C_{1-6}$alkyl then Y is hydrogen or $C_{1-6}$alkyl; their use as a medicine, their processes for preparation and pharmaceutical compositions comprising them.

49 Claims, No Drawings

HIV REPLICATION INHIBITORS

CROSS REFERENCE TO RELATED APPLICATIONS

This Application is a National Stage Application under 35 U.S.C. § 371 of PCT/EP01/04991, filed May 3, 2001, which claims priority to U.S. Provisional Application Ser. No. 60/202,472, filed May 8, 2000, all of which are incorporated herein by reference in their entirety.

The present invention concerns substituted amino pyrimidine or triazine derivatives having Human Immunodeficiency Virus (HIV) replication inhibiting properties. It also relates to their use as a medicine, their processes for preparation and pharmaceutical compositions comprising them.

WO 99/50250 and WO 00/27825 disclose substituted amino pyrimidine derivatives having HIV replication inhibiting properties.

EP 0,834,507, WO 99/50256 and WO 00/27828 disclose substituted amino triazine derivatives having HIV replication inhibiting properties.

WO 95/10506 concerns N-alkyl-N-aryl-pyrimidinamines having antagonistic activity at the CRF (Corticotropin Releasing Factor) receptor. Said compounds are claimed to have a therapeutic effect on psychiatric disorders and neurological diseases.

EP 0,270,111 describes pyrimidine derivatives having fungicidal activity.

The present compounds differ from the prior art compounds by their structure and by their improved HIV replication inhibiting properties.

The present invention concerns the use of a compound for the manufacture of a medicament for the prevention or the treatment of HIV (Human Immunodeficiency Virus) infection wherein the compound is a compound of formula (I)

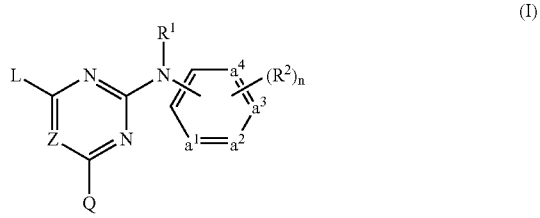

(I)

a N-oxide, a pharmaceutically acceptable addition salt, a quaternary amine and a stereochemically isomeric form thereof, wherein
-$a^1$=$a^2$-$a^3$=$a^4$- represents a bivalent radical of formula —CH=CH—CH=CH— (a-1);

—N=CH—CH=CH— (a-2);

—N=CH—N=CH— (a-3);

—N=CH—CH=N— (a-4);

—N=N—CH=CH— (a-5);

n is 0, 1, 2, 3 or 4; and in case -$a^1$=$a^2$-$a^3$=$a^4$- is (a-1), then n may also be 5;

$R^1$ is hydrogen; aryl; formyl; $C_{1-6}$alkylcarbonyl; $C_{1-6}$alkyl; $C_{1-6}$alkyloxycarbonyl;
$C_{1-6}$alkyl substituted with formyl, $C_{1-6}$alkylcarbonyl, $C_{1-6}$alkyloxycarbonyl, $C_{1-6}$alkylcarbonyloxy;
$C_{1-6}$alkyloxy$C_{1-6}$alkylcarbonyl substituted with $C_{1-6}$alkyloxycarbonyl;

each $R^2$ independently is hydroxy, halo, $C_{1-6}$alkyl optionally substituted with cyano or —C(=O)$R^6$, $C_{3-7}$cycloalkyl, $C_{2-6}$alkenyl optionally substituted with one or more halogen atoms or cyano, $C_{2-6}$alkynyl optionally substituted with one or more halogen atoms or cyano, $C_{1-6}$alkyloxy, $C_{1-6}$alkyloxycarbonyl, carboxyl, cyano, nitro, amino, mono- or di($C_{1-6}$alkyl)amino, polyhalomethyl, polyhalomethyloxy, polyhalomethylthio, —S(=O)$_p$$R^6$, —NH—S(=O)$_p$$R^6$, —C(=O)$R^6$, —NHC(=O)H, —C(=O)NHNH$_2$, —NHC(=O)$R^6$, —C(=NH)$R^6$ or a radical of formula

(c)

wherein each $A_1$ independently is N, CH or CR$^6$; and $A_2$ is NH, O, S or NR$^6$;

L is $C_{1-10}$alkyl, $C_{2-10}$alkenyl, $C_{2-10}$alkynyl, $C_{3-7}$cycloalkyl, whereby each of said groups may be substituted with one or two substituents independently selected from
$C_{3-7}$cycloalkyl,
indolyl or isoindolyl, each optionally substituted with one, two, three or four substituents each independently selected from halo, $C_{1-6}$alkyl, hydroxy, $C_{1-6}$alkyloxy, cyano, aminocarbonyl, nitro, amino, polyhalomethyl, polyhalomethyloxy and $C_{1-6}$alkylcarbonyl,
phenyl, pyridyl, pyrimidinyl, pyrazinyl or pyridazinyl, wherein each of said aromatic rings may optionally be substituted with one, two, three, four or five substituents each independently selected from the substituents defined in $R^2$; or L is —$X^1$—$R^3$ or —$X^2$-Alk-$R^4$ wherein
Alk is $C_{1-4}$alkanediyl;
$R^3$ or $R^4$ each independently are phenyl, pyridyl, pyrimidinyl, pyrazinyl or pyridazinyl, wherein each of said aromatic rings may optionally be substituted with one, two, three, four or five substituents each independently selected from the substituents defined in $R^2$; and
$X^1$ $X^2$ each independently are —NR$^7$—, —NH—NH—, —N=N—, —O—, —C(=O)—, —CHOH—, —S—, —S(=O)$_p$—;

Q represents cyano, hydroxy, mercapto, carboxyl, formyl, halo, cyano$C_{1-6}$alkyl, hydroxy$C_{1-6}$alkyl, mercapto$C_{1-6}$alkyl, amino$C_{1-6}$alkyl, mono- or di($C_{1-4}$alkyl)-amino$C_{1-6}$alkyl, aminocarbonyl, mono- or di($C_{1-4}$alkyl)aminocarbonyl, $C_{1-6}$alkyloxy, $C_{1-6}$alkylthio, $C_{1-6}$alkylS(=O)$_p$, $C_{1-6}$alkylcarbonyl, $C_{1-6}$alkylcarbonyloxy, $C_{1-6}$alkyloxycarbonyl, $C_{1-6}$alkylcarbonyloxy$C_{1-6}$alkyl, $C_{2-6}$alkenyl, $C_{2-6}$alkenyloxyamino, $R^5$—C(=O)—$C_{1-6}$alkyloxyamino, $C_{2-6}$alkynyl, polyhalo$C_{1-6}$alkyl, hydroxypolyhalo$C_{1-6}$alkyl, Het or $C_{1-6}$alkyloxy$C_{1-6}$alkyl wherein each hydrogen atom may optionally be substituted with $C_{1-6}$alkyloxy;

Z is C—Y or N wherein
Y represents hydrogen, hydroxy, halo, $C_{1-6}$alkyl, $C_{3-7}$cycloalkyl, $C_{2-6}$alkenyl optionally substituted with one or more halogen atoms, $C_{2-6}$alkynyl optionally substituted with one or more halogen atoms, $C_{1-6}$alkyl substituted with cyano or —C(=O)$R^8$, $C_{1-6}$alkyloxy, $C_{1-6}$alkyloxycarbonyl, carboxyl, cyano, nitro, amino, mono- or di($C_{1-6}$alkyl)amino, polyhalomethyl, polyhalomethyloxy, polyhalomethylthio, —S(=O)$_p$$R^8$, —NH—S (=O)$_p$R$^8$, —C(=O)R$^8$, —NHC(=O)H, —C(=O)NHNH$_2$, —NHC(=O)R$^8$, —C(=NH)R$^8$ or aryl;

R$^5$ is hydrogen or a radical of formula

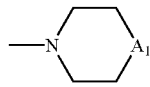
(d)

with A$_1$ being CH$_2$ or O;

R$^6$ is methyl, amino, mono- or dimethylamino or polyhalomethyl;

R$^7$ is hydrogen; aryl; formyl; C$_{1-6}$alkylcarbonyl; C$_{1-6}$alkyl; C$_{1-6}$alkyloxycarbonyl; C$_{1-6}$alkyl substituted with formyl, C$_{1-6}$alkyl carbonyl, C$_{1-6}$alkyloxycarbonyl, C$_{1-6}$alkylcarbonyloxy; C$_{1-6}$alkyloxyC$_{1-6}$alkylcarbonyl substituted with C$_{1-6}$alkyloxycarbonyl;

R$^8$ is methyl, amino, mono- or dimethylamino or polyhalomethyl;

p is 1 or 2;

aryl is phenyl or phenyl substituted with one, two, three, four or five substituents each independently selected from halo, C$_{1-6}$alkyl, C$_{3-7}$cycloalkyl, C$_{1-6}$alkyloxy, cyano, nitro, polyhaloC$_{1-6}$alkyl, polyhaloC$_{1-6}$alkyloxy, aminocarbonyl, tetrazolyl;

Het is imidazolyl, thiazolyl, oxazolyl, pyrazolyl, isothiazolyl, isoxazolyl, triazolyl, tetrazolyl optionally substituted with imino, a radical of formula (c) as described hereinabove, imidazolidinyl, pyrazolidinyl, thiazolidinyl, isothiazolidinyl, oxazolidinyl, isoxazolidinyl optionally substituted with hydroxy, isoxazolidinone, or a radical of formula

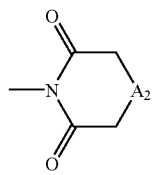
(e-1)

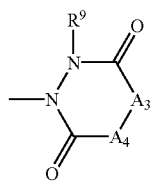
(e-2)

with A$_2$ being O, CH$_2$ or a direct bond;
A$_3$ being CH$_2$ or NH;
A$_4$ being CH$_2$ or a direct bond; or
A$_3$-A$_4$ representing CH=CH;
R$^9$ being hydrogen or C$_{1-4}$alkylcarbonyl;

provided that when Q is halo then Z is N; or when Q is polyhaloC$_{1-6}$alkyl then Y is hydrogen or C$_{1-6}$alkyl.

As used hereinbefore or hereinafter C$_{1-4}$alkyl as a group or part of a group defines straight or branched chain saturated hydrocarbon radicals having from 1 to 4 carbon atoms such as methyl, ethyl, propyl, 1-methylethyl, butyl and the like; C$_{1-6}$alkyl as a group or part of a group defines straight or branched chain saturated hydrocarbon radicals having from 1 to 6 carbon atoms such as the group defined for C$_{1-4}$alkyl and pentyl, hexyl, 2-methylbutyl and the like; C$_{1-10}$alkyl as a group or part of a group defines straight or branched chain saturated hydrocarbon radicals having from 1 to 10 carbon atoms such as the groups defined for C$_{1-6}$alkyl and heptyl, octyl, nonyl, decyl, 2-methyl-heptyl, 3-ethyl-heptyl and the like; C$_{1-4}$alkanediyl defines straight or branched chain saturated bivalent hydrocarbon radicals having from 1 to 4 carbon atoms such as methylene, 1,2-ethanediyl or 1,2-ethylidene, 1,3-propanediyl or 1,3-propylidene, 1,4-butanediyl or 1,4-butylidene and the like; C$_{3-7}$cycloalkyl is generic to cyclopropyl, cyclobutyl, cyclopentyl, cyclohexyl and cycloheptyl; C$_{2-6}$alkenyl defines straight and branched chain hydrocarbon radicals having from 2 to 6 carbon atoms containing a double bond such as ethenyl, propenyl, butenyl, pentenyl, hexenyl and the like; C$_{2-10}$alkenyl defines straight and branched chain hydrocarbon radicals having from 2 to 10 carbon atoms containing a double bond such as the groups defined for C$_{2-6}$alkenyl and heptenyl, octenyl, nonenyl, decenyl and the like; C$_{2-6}$alkynyl defines straight and branched chain hydrocarbon radicals having from 2 to 6 carbon atoms containing a triple bond such as ethynyl, propynyl, butynyl, pentynyl, hexynyl and the like; C$_{2-10}$alkynyl defines straight and branched chain hydrocarbon radicals having from 2 to 10 carbon atoms containing a triple bond such as the groups defined for C$_{2-6}$alkynyl and heptynyl, octynyl, nonynyl, decynyl and the like.

As used herein before, the term (=O) forms a carbonyl moiety when attached to a carbon atom, a sulfoxide moiety when attached to a sulfur atom and a sulfonyl moiety when two of said terms are attached to a sulfur atom.

The term halo is generic to fluoro, chloro, bromo and iodo. As used in the foregoing and hereinafter, polyhalomethyl as a group or part of a group is defined as mono- or polyhalosubstituted methyl, in particular methyl with one or more fluoro atoms, for example, difluoromethyl or trifluoromethyl; polyhaloC$_{1-6}$alkyl as a group or part of a group is defined as mono- or polyhalosubstituted C$_{1-6}$alkyl, for example, the groups defined in halomethyl, 1,1-difluoroethyl and the like. In case more than one halogen atoms are attached to an alkyl group within the definition of polyhalomethyl or polyhaloC$_{1-6}$alkyl, they may be the same or different.

Het is meant to include all the possible isomeric forms of the heterocycles mentioned in the definition of Het, for instance, imidazolyl also includes 2H-imidazolyl.

The Het radical may be attached to the remainder of the molecule of formula (I) through any ring carbon or heteroatom as appropriate, if not otherwise specified. Thus, for example, when the heterocycle is imidazolyl, it may be 1-imidazolyl, 2-imidazolyl, 4-imidazolyl and the like.

When any variable (eg. aryl, R$^2$, etc.) occurs more than one time in any constituent, each definition is independent.

Lines drawn into ring systems from substituents indicate that the bond may be attached to any of the suitable ring atoms.

For therapeutic use, salts of the compounds of formula (I) are those wherein the counterion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not are included within the ambit of the present invention.

The pharmaceutically acceptable addition salts as mentioned hereinabove are meant to comprise the therapeutically active non-toxic acid addition salt forms which the compounds of formula (I) are able to form. The latter can conveniently be obtained by treating the base form with such appropriate acids as inorganic acids, for example, hydrohalic acids, e.g. hydrochloric, hydrobromic and the like; sulfuric acid; nitric acid; phosphoric acid and the like; or organic acids, for example, acetic, propanoic, hydroxy-acetic, 2-hydroxypropanoic, 2-oxopropanoic, oxalic, malonic, succinic, maleic, fumaric, malic, tartaric, 2-hydroxy-1,2,3-propanetricarboxylic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids. Conversely the salt form can be converted by treatment with alkali into the free base form.

The compounds of formula (I) containing acidic protons may be converted into their therapeutically active non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. primary, secondary and tertiary aliphatic and aromatic amines such as methylamine, ethylamine, propylamine, isopropylamine, the four butylamine isomers, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline, the benzathine, N-methyl-D-glucamine, 2-amino-2-(hydroxymethyl)-1,3-propanediol, hydrabamine salts, and salts with amino acids such as, for example, arginine, lysine and the like. Conversely the salt form can be converted by treatment with acid into the free acid form. The term addition salt also comprises the hydrates and solvent addition forms which the compounds of formula (I) are able to form. Examples of such forms are e.g. hydrates, alcoholates and the like.

The term "quaternary amine" as used hereinbefore defines the quaternary ammonium salts which the compounds of formula (I) are able to form by reaction between a basic nitrogen of a compound of formula (I) and an appropriate quaternizing agent, such as, for example, an optionally substituted alkylhalide, arylhalide or arylalkylhalide, e.g. methyliodide or benzyliodide. Other reactants with good leaving groups may also be used, such as alkyl trifluoromethanesulfonates, alkyl methanesulfonates, and alkyl p-toluenesulfonates. A quaternary amine has a positively charged nitrogen. Pharmaceutically acceptable counterions include chloro, bromo, iodo, trifluoroacetate and acetate. The counterion of choice can be introduced using ion exchange resins.

It will be appreciated that some of the compounds of formula (I) and their N-oxides, addition salts, quaternary amines and stereochemically isomeric forms may contain one or more centers of chirality and exist as stereochemically isomeric forms.

The term "stereochemically isomeric forms" as used hereinbefore defines all the possible stereoisomeric forms which the compounds of formula (I), and their N-oxides, addition salts, quaternary amines or physiologically functional derivatives may possess. Unless otherwise mentioned or indicated, the chemical designation of compounds denotes the mixture of all possible stereochemically isomeric forms, said mixtures containing all diastereomers and enantiomers of the basic molecular structure as well as each of the individual isomeric forms of formula (I) and their N-oxides, salts, solvates or quaternary amines substantially free, i.e. associated with less than 10%, preferably less than 5%, in particular less than 2% and most preferably less than 1% of the other isomers. In particular, stereogenic centers may have the R- or S-configuration; substituents on bivalent cyclic (partially) saturated radicals may have either the cis- or trans-configuration. Compounds encompassing double bonds can have an E or Z-stereochemistry at said double bond. Stereochemically isomeric forms of the compounds of formula (I) are obviously intended to be embraced within the scope of this invention.

The N-oxide forms of the present compounds are meant to comprise the compounds of formula (I) wherein one or several nitrogen atoms are oxidized to the so-called N-oxide.

Some of the compounds of formula (I) may also exist in their tautomeric form. Such forms although not explicitly indicated in the above formula are intended to be included within the scope of the present invention.

Whenever used hereinafter, the term "compounds of formula (I)" is meant to also include their N-oxide forms, their salts, their quaternary amines and their stereochemically isomeric forms. Of special interest are those compounds of formula (I) which are stereochemically pure.

The invention also concerns a compound of formula (I')

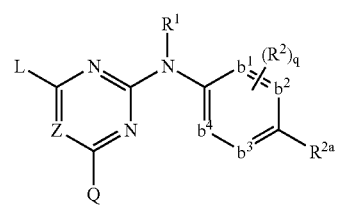

(I')

the N-oxides, the pharmaceutically acceptable addition salts, the quaternary amines and the stereochemically isomeric forms thereof, wherein
-$b^1$=$b^2$-C($R^{2a}$)=$b^3$-$b^4$=represents a bivalent radical of formula

| —CH=CH—C($R^{2a}$)=CH—CH= | (b-1); |
| —N=CH—C($R^{2a}$)=CH—CH= | (b-2); |
| —CH=N—C($R^{2a}$)=CH—CH= | (b-3); |
| —N=CH—C($R^{2a}$)=N—CH= | (b-4); |
| —N=CH—C($R^{2a}$)=CH—N= | (b-5); |
| —CH=N—C($R^{2a}$)=N—CH= | (b-6); |
| —N=N—C($R^{2a}$)=CH—CH= | (b-7). | q is 0, 1, 2; or where possible q is 3 or 4;
$R^1$ is hydrogen; aryl; formyl; $C_{1-6}$alkylcarbonyl; $C_{1-6}$alkyl; $C_{1-6}$alkyloxycarbonyl; $C_{1-6}$alkyl substituted with formyl, $C_{1-6}$alkylcarbonyl, $C_{1-6}$alkyloxycarbonyl, $C_{1-6}$alkylcarbonyloxy; $C_{1-6}$alkyloxy$C_{1-6}$alkylcarbonyl substituted with $C_{1-6}$alkyloxycarbonyl;
$R^{2a}$ is cyano, aminocarbonyl, mono- or di(methyl)aminocarbonyl, $C_{1-6}$alkyl substituted with cyano, aminocarbonyl or mono- or di(methyl)aminocarbonyl, $C_{2-6}$alkenyl substituted with cyano, or $C_{2-6}$alkynyl substituted with cyano;
each $R^2$ independently is hydroxy, halo, $C_{1-6}$alkyl optionally substituted with cyano or —C(=O)$R^6$, $C_{3-7}$cycloalkyl, $C_{2-6}$alkenyl optionally substituted with one or more halogen atoms or cyano, $C_{2-6}$alkynyl optionally substituted with one or more halogen atoms or cyano, $C_{1-6}$alkyloxy, $C_{1-6}$alkyloxycarbonyl, carboxyl, cyano, nitro, amino, mono- or di($C_{1-6}$alkyl)amino, polyhalomethyl, polyhalomethyloxy, polyhalomethylthio, —S(=O)$_p$$R^6$, —NH—S(=O)$_p$$R^6$, —C(=O)$R^6$, —NHC(=O)H, —C(=O)NHNH$_2$, —NHC(=O)$R^6$, —C(=NH)$R^6$ or a radical of formula

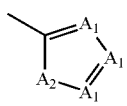

(c)

wherein each $A_1$ independently is N, CH or $CR^6$; and $A_2$ is NH, O, S or $NR^6$;

L is $C_{1-10}$alkyl, $C_{2-10}$alkenyl, $C_{2-10}$alkynyl, $C_{3-7}$cycloalkyl, whereby each of said groups may be substituted with one or two substituents independently selected from $C_{3-7}$cycloalkyl, indolyl or isoindolyl, each optionally substituted with one, two, three or four substituents each independently selected from halo, $C_{1-6}$alkyl, hydroxy, $C_{1-6}$alkyloxy, cyano, aminocarbonyl, nitro, amino, polyhalomethyl, polyhalomethyloxy and $C_{1-6}$alkylcarbonyl, phenyl, pyridyl, pyrimidinyl, pyrazinyl or pyridazinyl, wherein each of said aromatic rings may optionally be substituted with one, two, three, four or five substituents each independently selected from the substituents defined in $R^2$; or L is $-X^1-R^3$ or $-X^2$-Alk-$R^4$ wherein Alk is $C_{1-4}$alkanediyl;

$R^3$ or $R^4$ each independently are phenyl, pyridyl, pyrimidinyl, pyrazinyl or pyridazinyl, wherein each of said aromatic rings may optionally be substituted with one, two, three, four or five substituents each independently selected from the substituents defined in $R^2$; and $X^1$ or $X^2$ each independently are $-NR^7-$, $-NH-NH-$, $-N=N-$, $-O-$, $-C(=O)-$, $-CHOH-$, $-S-$, $-S(=O)_p-$;

Q represents cyano, hydroxy, mercapto, carboxyl, formyl, halo, cyano$C_{1-6}$alkyl, hydroxy$C_{1-6}$alkyl, mercapto$C_{1-6}$alkyl, amino$C_{1-6}$alkyl, mono- or di($C_{1-4}$alkyl)-amino$C_{1-6}$alkyl, aminocarbonyl, mono- or di($C_{1-4}$alkyl)aminocarbonyl, $C_{1-6}$alkyloxy, $C_{1-6}$alkylthio, $C_{1-6}$alkylS(=O)$_p$, $C_{1-6}$alkylcarbonyl, $C_{1-6}$alkylcarbonyloxy, $C_{1-6}$alkyloxycarbonyl, $C_{1-6}$alkylcarbonyloxy$C_{1-6}$alkyl, $C_{2-6}$alkenyl, $C_{2-6}$alkenyloxyamino, $R^5-C(=O)-C_{1-6}$alkyloxyamino, $C_{2-6}$alkynyl, polyhalo$C_{1-6}$alkyl, hydroxypolyhalo$C_{1-6}$alkyl, Het or $C_{1-6}$alkyloxy$C_{1-6}$alkyl wherein each hydrogen atom may optionally be substituted with $C_{1-6}$alkyloxy;

Z is C—Y or N wherein

Y represents hydrogen, hydroxy, halo, $C_{1-6}$alkyl, $C_{3-7}$cycloalkyl, $C_{2-6}$alkenyl optionally substituted with one or more halogen atoms, $C_{2-6}$alkynyl optionally substituted with one or more halogen atoms, $C_{1-6}$alkyl substituted with cyano or $-C(=O)R^8$, $C_{1-6}$alkyloxy, $C_{1-6}$alkyloxycarbonyl, carboxyl, cyano, nitro, amino, mono- or di($C_{1-6}$alkyl)amino, polyhalomethyl, polyhalomethyloxy, polyhalomethylthio, $-S(=O)_pR^8$, $-NH-S(=O)_pR^8$, $-C(=O)R^8$, $-NHC(=O)H$, $-C(=)NHNH_2$, $-NHC(=O)R^8$, $-C(=NH)R^8$ or aryl;

$R^5$ is hydrogen or a radical of formula

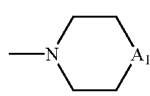

(d)

with $A_1$ being $CH_2$ or O;

$R^6$ is methyl, amino, mono- or dimethylamino or polyhalomethyl;

$R^7$ is hydrogen; aryl; formyl; $C_{1-6}$alkylcarbonyl; $C_{1-6}$alkyl; $C_{1-6}$alkyloxycarbonyl; $C_{1-6}$alkyl substituted with formyl, $C_{1-6}$alkylcarbonyl, $C_{1-6}$alkyloxycarbonyl, $C_{1-6}$alkylcarbonyloxy; $C_{1-6}$alkyloxy$C_{1-6}$alkylcarbonyl substituted with $C_{1-6}$alkyloxycarbonyl;

$R^8$ is methyl, amino, mono- or dimethylamino or polyhalomethyl;

p is 1 or 2;

aryl is phenyl or phenyl substituted with one, two, three, four or five substituents each independently selected from halo, $C_{1-6}$alkyl, $C_{3-7}$cycloalkyl, $C_{1-6}$alkyloxy, cyano, nitro, polyhalo$C_{1-6}$alkyl, polyhalo$C_{1-6}$alkyloxy, aminocarbonyl, tetrazolyl;

Het is imidazolyl, thiazolyl, oxazolyl, pyrazolyl, isothiazolyl, isoxazolyl, triazolyl, tetrazolyl optionally substituted with imino, a radical of formula (c) as described hereinabove, imidazolidinyl, pyrazolidinyl, thiazolidinyl, isothiazolidinyl, oxazolidinyl, isoxazolidinyl optionally substituted with hydroxy, isoxazolidinone, or a radical of formula

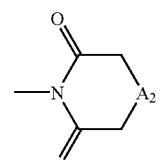

(e-1)

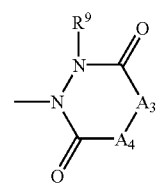

(e-2)

with $A_2$ being O, $CH_2$ or a direct bond;

$A_3$ being $CH_2$ or NH;

$A_4$ being $CH_2$ or a direct bond; or $A_3$-$A_4$ representing CH=CH;

$R^9$ being hydrogen or $C_{1-4}$alkylcarbonyl;

provided that when Q is halo then Z is N; or when Q is polyhalo$C_{1-6}$alkyl then Y is hydrogen or $C_{1-6}$alkyl.

Another interesting group of compounds are those compounds of formula (I) or (I') wherein Q is cyano, hydroxy, mercapto, carboxyl, formyl, cyano$C_{1-6}$alkyl, hydroxy-$C_{1-6}$alkyl, mercapto$C_{1-6}$alkyl, amino$C_{1-6}$alkyl, mono- or di($C_{1-4}$alkyl)amino-$C_{1-6}$alkyl, aminocarbonyl, mono- or di($C_{1-4}$alkyl)aminocarbonyl, $C_{1-6}$alkyloxy-$C_{1-6}$alkyl wherein each hydrogen atom may optionally be substituted with $C_{1-6}$alkyloxy, $C_{1-6}$alkyloxy, $C_{1-6}$alkylthio, $C_{1-6}$alkylS(=O)$_p$, $C_{1-6}$alkylcarbonyl, $C_{1-6}$alkylcarbonyloxy, $C_{1-6}$alkyloxycarbonyl, $C_{1-6}$alkylcarbonyloxy$C_{1-6}$alkyl, $C_{2-6}$alkenyl, $C_{2-6}$alkenyloxyamino, $R^5-C(=O)-C_{1-6}$alkyloxyamino, $C_{2-6}$alkynyl, hydroxypolyhalo$C_{1-6}$alkyl, or Het.

Also an interesting group of compounds are those compounds of formula (I) or (I') wherein Q is cyano, hydroxy, mercapto, carboxyl, hydroxy$C_{1-6}$alkyl, mono- or di($C_{1-4}$alkyl)amino$C_{1-6}$alkyl, aminocarbonyl, $C_{1-6}$alkyloxy$C_{1-6}$alkyl wherein each hydrogen atom may optionally be substituted with $C_{1-6}$alkyloxy, $C_{1-6}$alkyloxy, $C_{1-6}$alkylthio, $C_{1-6}$alkylS(=O), $C_{1-6}$alkyloxycarbonyl, halo, polyhalo$C_{1-6}$alkyl, $C_{2-6}$alkenyloxyamino, $R^5-C(=O)-C_{1-6}$alkyloxyamino, a radical of formula (c) or (e-1) or (e-2), imidazolyl, triazolyl, tetrazolyl optionally substituted with imino, isoxazolidinyl optionally substituted with hydroxy, isoxazolidinone.

A further interesting group of compounds are those compounds of formula (I) or (I') wherein Q is cyano, hydroxy, mercapto, carboxyl, hydroxy$C_{1-6}$alkyl, mono- or di ($C_{1-4}$alkyl)amino$C_{1-6}$alkyl, aminocarbonyl, $C_{1-6}$alkyloxy$C_{1-6}$ alkyl wherein each hydrogen atom may optionally be substituted with $C_{1-6}$alkyloxy, $C_{1-6}$alkyloxy, $C_{1-6}$alkylthio, $C_{1-6}$alkylS(=O), $C_{1-6}$alkyloxycarbonyl, $C_{2-6}$alkenyloxyamino, $R^5$—C(=O)—$C_{1-6}$alkyloxyamino, a radical of formula (c) or (e-1) or (e-2), imidazolyl, triazolyl, tetrazolyl optionally substituted with imino, isoxazolidinyl optionally substituted with hydroxy, isoxazolidinone.

Still a further interesting group of compounds are those compounds of formula (I) or (I') wherein Z is C—Y.

Still another interesting group of compounds are those compounds of formula (I) or (I') wherein Z is N.

Also an interesting group of compounds are those compounds of formula (I) or (I') wherein Z is C—Y and Q is hydroxy$C_{1-6}$alkyl, mono- or di($C_{1-4}$alkyl)amino$C_{1-6}$alkyl, $C_{1-6}$alkyloxy$C_{1-6}$alkyl wherein each hydrogen atom may optionally be substituted with $C_{1-6}$alkyloxy, carboxyl, $C_{1-6}$alkyloxycarbonyl, polyhalo$C_{1-6}$alkyl, aminocarbonyl, imidazolyl.

Also an interesting group of compounds are those compounds of formula (I) or (I') wherein Z is C—Y and Q is hydroxy$C_{1-6}$alkyl, mono- or di($C_{1-4}$alkyl)amino$C_{1-6}$alkyl, $C_{1-6}$alkyloxy$C_{1-6}$alkyl wherein each hydrogen atom may optionally be substituted with $C_{1-6}$alkyloxy, carboxyl, $C_{1-6}$alkyloxycarbonyl, aminocarbonyl, imidazolyl.

Yet another interesting group of compounds are those compounds of formula (I) or (I') wherein Z is N and Q is cyano, hydroxy, $C_{1-6}$alkyloxy, $C_{1-6}$alkylthio, sulfhydryl, $C_{1-6}$alkylS(=O), aminocarbonyl, halo, $C_{2-6}$alkenyloxyamino, $R^5$—C(=O)—$C_{1-6}$alkyloxyamino, a radical of formula (c) or (e-1) or (e-2), imidazolyl, triazolyl, tetrazolyl optionally substituted with imino, isoxazolidinyl optionally substituted with hydroxy, isoxazolidinone.

Also an interesting group of compounds are those compounds of formula (I) or (I') wherein Z is N and Q is cyano, hydroxy, $C_{1-6}$alkyloxy, $C_{1-6}$alkylthio, sulfhydryl, $C_{1-6}$alkylS(=O), aminocarbonyl, $C_{2-6}$alkenyloxyamino, $R^5$—C(=O)—$C_{1-6}$alkyloxyamino, a radical of formula (c) or (e-1) or (e-2), imidazolyl, triazolyl, tetrazolyl optionally substituted with imino, isoxazolidinyl optionally substituted with hydroxy, isoxazolidinone.

Yet another interesting group of compounds are those compounds of formula (I) or (I') wherein L is $C_{1-10}$alkyl, $C_{2-10}$alkenyl, $C_{2-10}$alkynyl, $C_{3-7}$cycloalkyl, whereby each of said groups may be substituted with one or two substituents independently selected from $C_{3-7}$cycloalkyl; indolyl or isoindolyl, each optionally substituted with one, two, three or four substituents each independently selected from halo, $C_{1-6}$alkyl, hydroxy, $C_{1-6}$alkyloxy, cyano, aminocarbonyl, nitro, amino, polyhalomethyl, polyhalomethyloxy and $C_{1-6}$alkylcarbonyl; phenyl, pyridyl, pyrimidinyl, pyrazinyl or pyridazinyl, wherein each of said aromatic rings may optionally be substituted with one, two, three, four or five substituents each independently selected from the substituents defined in $R^2$; or L is —$X^1$—$R^3$.

Still another interesting group of compounds are those compounds of formula (I) or (I') wherein Y is hydroxy, halo, $C_{3-7}$cycloalkyl, $C_{2-6}$alkenyl optionally substituted with one or more halogen atoms, $C_{2-6}$alkynyl optionally substituted with one or more halogen atoms, $C_{1-6}$alkyl substituted with cyano or —C(=O)$R^8$, $C_{1-6}$alkyloxy, $C_{1-6}$alkyloxycarbonyl, carboxyl, cyano, nitro, amino, mono- or di($C_{1-6}$alkyl)amino, polyhalomethyl, polyhalomethyloxy, polyhalomethylthio, —S(=O)$_p R^8$, —NH—S(=O)$_p R^8$, —C(=O)$R^8$, —NHC(=O)H, —C(=O)NHNH$_2$, —NHC(=O)$R^8$, —C(=NH)$R^8$ or aryl.

Also an interesting group of compounds are those compounds of formula (I) wherein -$a^1$=$a^2$-$a^3$=$a^4$-represents a bivalent radical of formula

(a-1)

or

(a-2).

Also an interesting group of compounds are those compounds of formula (I') wherein -$b^1$=$b^2$-C($R^{2a}$)=$b^3$-$b^4$=represents a bivalent radical of formula

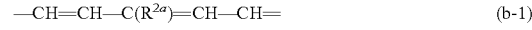
(b-1)

or

(b-3).

Still another interesting group of compounds are those compounds of formula (I) or (I') wherein L is —X—$R^3$ wherein $R^3$ is 2,4,6-trisubstituted phenyl, wherein each substituent is independently selected from chloro, bromo, fluoro, cyano or $C_{1-4}$alkyl.

Particular compounds are those compounds of formula (I) or (I') wherein the moiety in the 2 position of the pyrimidine ring is a 4-cyano-anilino group or a 4-aminocarbonyl-anilino group.

Preferred compounds are those compounds of formula (I) or (I') wherein the moiety in the 2 position of the pyrimidine ring is a 4-cyano-anilino group, L is —X—$R^3$ wherein $R^3$ is a 2,4,6-trisubstituted phenyl, Z is N or C—Y with Y being halo or hydrogen and Q is hydroxy$C_{1-6}$alkyl, $C_{1-6}$alkyloxy$C_{1-6}$alkyl, halo, polyhalo$C_{1-6}$alkyl, aminocarbonyl, mono- or di($C_{1-4}$alkyl)aminocarbonyl, cyano or Het.

Preferred compounds of formula (I) or (I') are selected from
4-[[[5-bromo-4-(4-cyano-2,6-dimethylphenoxy)-6-hydroxymethyl]-2-pyrimidinyl]amino]benzonitrile;
4-[[[6-chloro-4-(2,4,6-trimethylphenylamino)]-1,3,5-triazin-2-yl]amino]benzonitrile;
4-[[[6-trifluoromethyl-2-(4-cyanophenylamino)]-4-pyrimidinyl]amino]-3,5-dimethylbenzonitrile;
6-[(4-cyanophenyl)amino]-4-[(2,4,6-trimethylphenyl)amino]-1,3,5-triazine-2-carboxamide;
4-[[[5-bromo-4-(4-cyano-2,6-dimethylphenoxy)-6-methoxymethyl]-2-pyrimidinyl]amino]benzonitrile;
4-[[[5-bromo-4-(4-cyano-2,6-dibromophenoxy)-6-hydroxymethyl]2-pyrimidinyl]amino]benzonitrile;
2-[(4-cyanophenyl)amino]-6-[(2,4,6-trimethylphenyl)amino]-4-pyrimidine carboxamide;
5-bromo-2-[(4-cyanophenyl)amino]-6-[(2,4,6-trimethylphenyl)amino]-4-pyrimidine carboxamide;
their N-oxides, pharmaceutically acceptable addition salts, quaternary amines and stereochemically isomeric forms thereof.

In general, compounds of formula (I) can be prepared by reacting an intermediate of formula (II) wherein $W_1$ is a suitable leaving group such as, for example, a halogen, hydroxy, triflate, tosylate, thiomethyl, methylsulfonyl, trifluoromethylsulfonyl and the like, with an amino derivative of formula (III) under solvent-free conditions or in a suitable solvent such as, for example, water, ethanol, 1-methyl-2-pyrrolidinone, N,N-dimethylformamide, 1,4-dioxane, 1,2-dimethoxy-ethane, tetrahydrofuran, dimethyl sulfoxide, tetraline, sulfolane, acetonitrile, toluene and the like, optionally under a reaction-inert atmosphere such as, for example, oxygen free argon or nitrogen, optionally in the presence of a suitable acid such as, for example, 1 N hydrochloric acid in diethyl ether or the like or a suitable base, such as N,N-diisopropylethanamine, NaI, BuOH, and optionally in the presence of a suitable catalyst, such as for example tetrakis(triphenylphosphine) palladium. This reaction can be performed at a temperature ranging between 50° C. and 250° C.

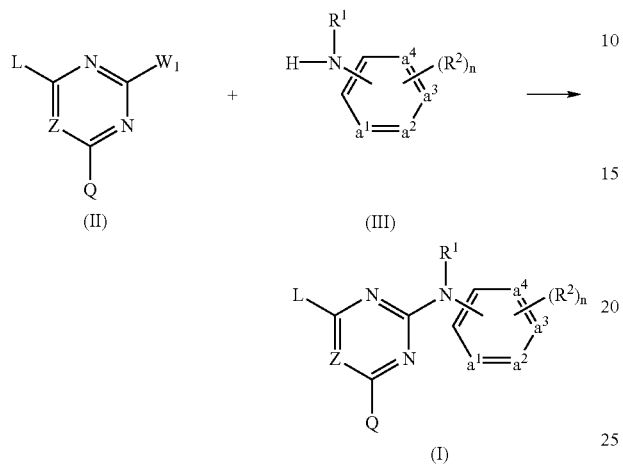

Alternatively, a compound of formula (I) wherein L represents $C_{1-10}$alkyl, $C_{2-10}$alkenyl, $C_{2-10}$alkynyl, $C_{3-7}$cycloalkyl, whereby each of said groups may be substituted with one or two substituents independently selected from $C_{3-7}$cycloalkyl; indolyl or isoindolyl, each optionally substituted with one, two, three or four substituents each independently selected from halo, $C_{1-6}$alkyl, hydroxy, $C_{1-6}$alkyloxy, cyano, aminocarbonyl, nitro, amino, polyhalomethyl, polyhalomethyloxy and $C_{1-6}$alkylcarbonyl; phenyl, pyridyl, pyrimidinyl, pyrazinyl or pyridazinyl, wherein each of said aromatic rings may optionally be substituted with one, two, three, four or five substituents each independently selected from the substituents defined in $R^2$, said L being represented by $L_a$, and said compounds being represented by formula (I-a), can also be prepared by reacting an intermediate of formula (III) with an intermediate of formula (IV) and an intermediate of formula (V) in the presence of magnesium and in the presence of a suitable solvent such as diethylether, benzene, 1,4-dioxane, N,N-diethylethanamine.

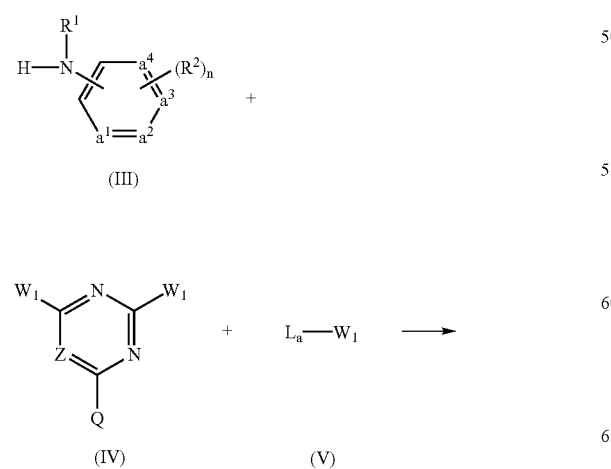

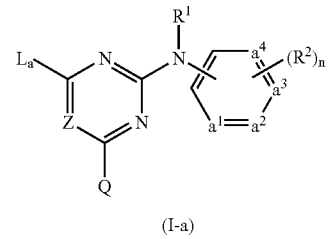

In this and the following preparations, the reaction products may be isolated from the reaction medium and, if necessary, further purified according to methodologies generally known in the art such as, for example, extraction, crystallization, distillation, trituration and chromatography.

The compounds of formula (I) wherein L is a radical of formula $-NR^7-R^3$, said compounds being represented by formula (I-b), can be prepared by reacting an intermediate of formula (VI) wherein $W_2$ is a suitable leaving group such as, for example, a halogen or a triflate, with an intermediate of formula (VII) under solvent-free conditions or in an appropriate solvent such as, for example, ethanol, 1-methyl-2-pyrrolidinone, N,N-dimethylformamide, 1,4-dioxane, tetrahydrofuran, dimethyl sulfoxide, tetraline, sulfolane, acetonitrile and the like, under a reaction-inert atmosphere such as, for example, oxygen free argon or nitrogen, and optionally in the presence of a suitable acid such as, for example, 1 N hydrochloric acid in diethyl ether or the like or a suitable base, such as N,N-diisopropylethanamine. This reaction can be performed at a temperature ranging between 50° C. and 250° C.

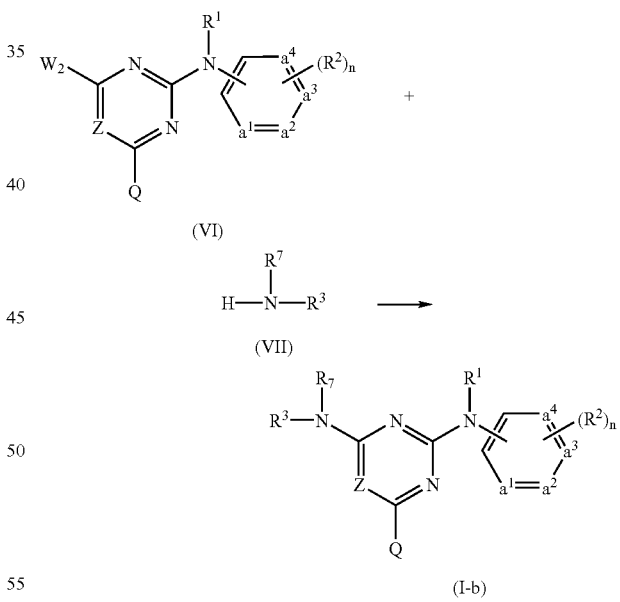

The compounds of formula (I) wherein L is a radical of formula $-X^1-R^3$ or $-X^2$-Alk-$R^4$, said L being represented by $L_b$, and said compounds being represented by formula (I-c), can be prepared by reacting an intermediate of formula (VI) wherein $W_2$ is a suitable leaving group such as, for example a halogen or a triflate, with an intermediate of formula (VIIII) in an appropriate solvent such as, for example, 1-methyl-2-pyrrolidinone, 1,4-dioxane, dimethyl sulfoxide, tetraline, sulfolane, tetrahydrofuran, acetone, acetone/water and the like under a reaction-inert atmosphere such as, for example, oxygen free argon or nitrogen, and in the presence of a suitable base such as, for example, sodium hydride, potassium hydride, sodium hydroxide, N,N-diisopropylethanamine or the like. This reaction can be performed at a temperature ranging between 50° C. and 250° C.

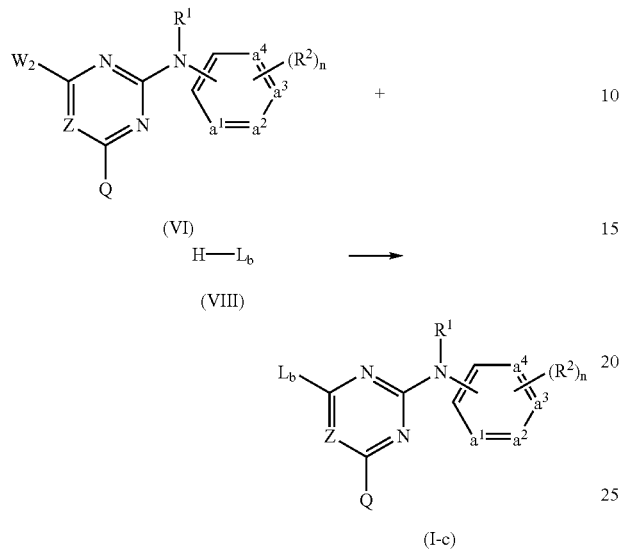

The compounds of formula (I) wherein Q is a radical of formula (e-1), said compounds being represented by formula (I-d), can be prepared by reacting an intermediate of formula (IX-a) with an intermediate of formula (X), wherein $W_3$ represents a suitable leaving group, such as a halogen, e.g. chloro, bromo and the like.

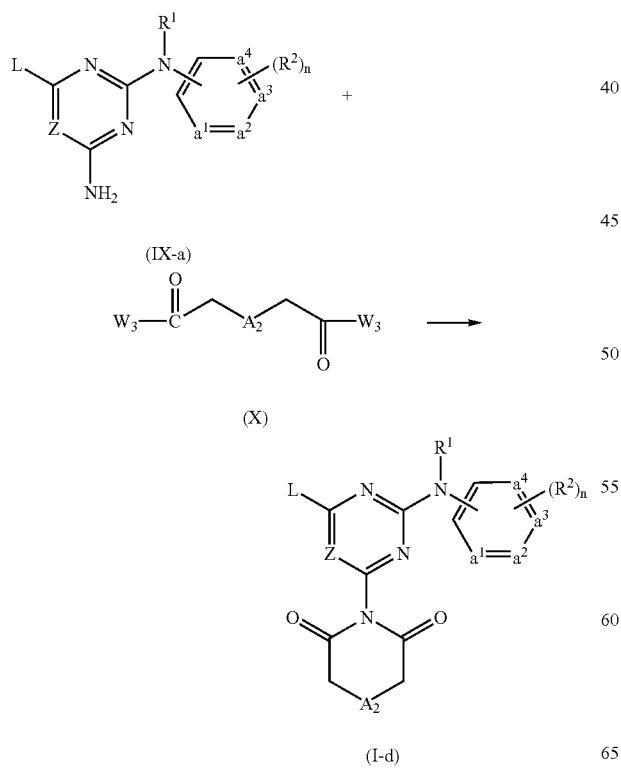

The compounds of formula (I), wherein Q is a radical of formula (e-2), said compounds being represented by formula (I-e), can be prepared by cycling an intermediate of formula (IX-b) in the presence of a suitable carbonic derivative, such as for example acetic acid anhydride, and in the presence of a suitable base, such as sodium acetate.

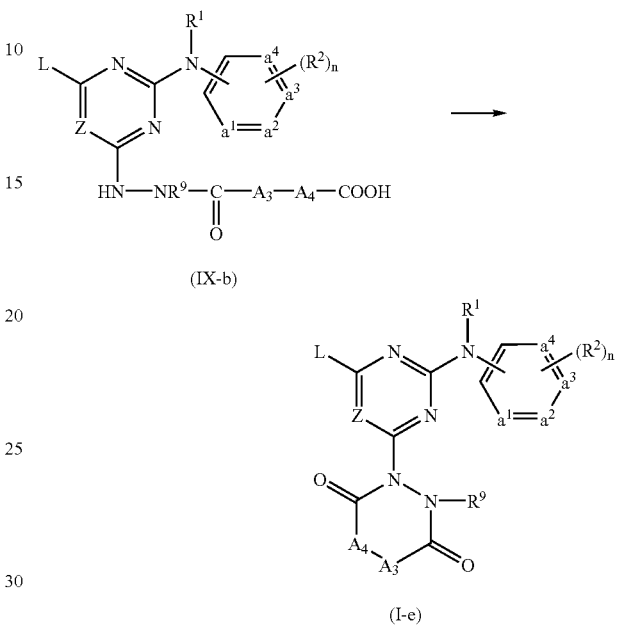

The compounds of formula (I-e), wherein $A_3$ is NH and $A_4$ is a direct bond, said compounds being represented by formula (I-e-1), can be prepared by reacting an intermediate of formula (IX-c) with a carbonic derivative, such as for example carbonic dichloride, in the presence of a suitable solvent, such as for example dioxane.

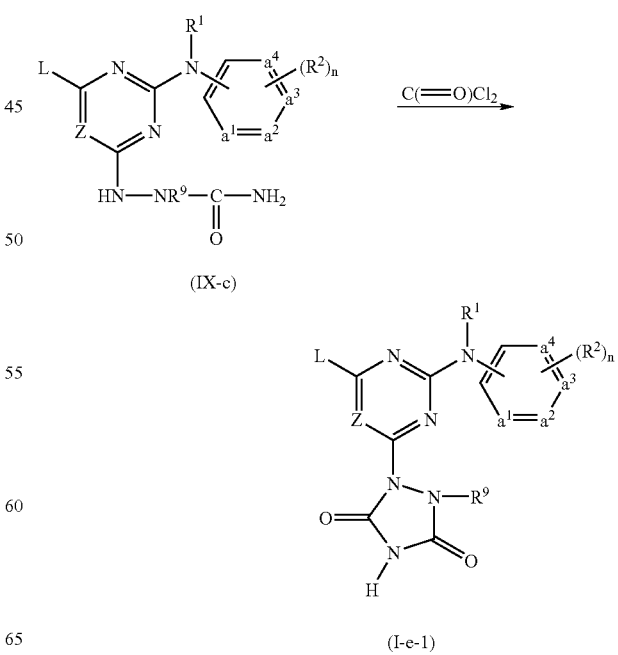

The compounds of formula (I), wherein Q is isoxazolidinone, said compounds being represented by formula (I-f), can be prepared by reacting an intermediate of formula (IX-d) with $W_4$—$CH_2$—$CH_2$—$C(=O)$—$W_4$, wherein $W_4$ represents a suitable leaving group, such as a halogen, e.g. chloro, bromo and the like, in the presence of a suitable base, such as for example N N-diethylethanamine, and a suitable solvent, such as tetrahydrofuran.

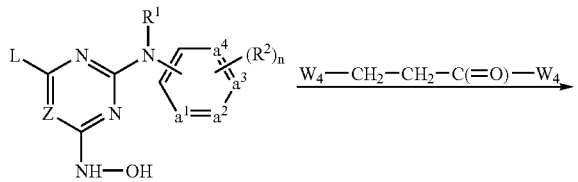

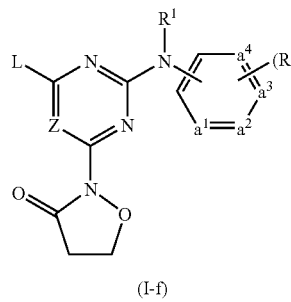

The compounds of formula (I) wherein Z is N, said compounds being represented by formula (I-g), can be prepared by reacting an intermediate of formula (XXIII) with an intermediate of formula (XXIV) and an intermediate of formula (XXV) in the presence of a suitable base, such as for example sodium acetate or $Na_2CO_3$, and a suitable solvent, such as acetonitrile.

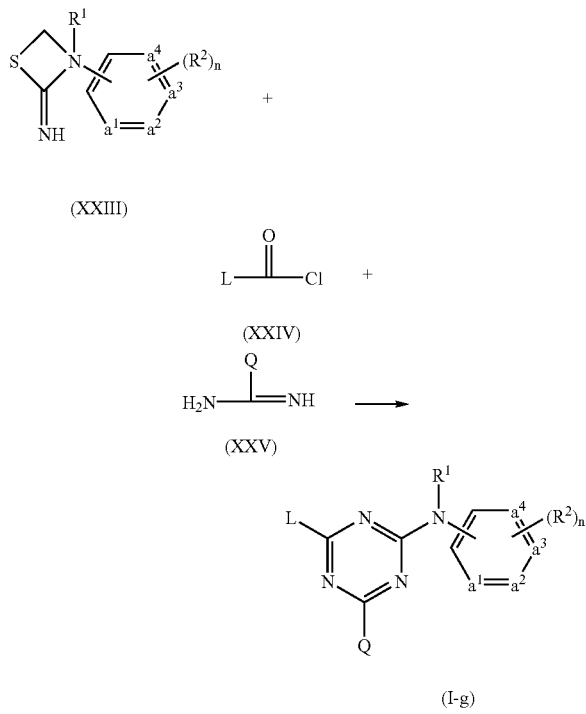

The compounds of formula (I) may further be prepared by converting compounds of formula (I) into each other according to art-known group transformation reactions.

The compounds of formula (I) may be converted to the corresponding N-oxide forms following art-known procedures for converting a trivalent nitrogen into its N-oxide form. Said N-oxidation reaction may generally be carried out by reacting the starting material of formula (I) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. tert.butyl hydro-peroxide. Suitable solvents are, for example, water, lower alcohols, e.g. ethanol and the like, hydrocarbons, e.g. toluene, ketones, e.g. 2-butanone, halogenated hydrocarbons, e.g. dichloromethane, and mixtures of such solvents.

For instance, compounds of formula (I) wherein Q is halo, can be converted into a compound of formula (I) wherein Q is cyano, by reaction with a suitable cyano-introducing agent, such as sodium cyanide or copper(I) cyanide, optionally in the presence of a suitable catalyst, such as for example tetrakis(triphenylphosphine) palladium and in the presence of a suitable solvent, such as N,N-dimethyl-aniline or 1-methyl-2-pyrrolidinone. A compound of formula (I) wherein Q is cyano, can further be converted into a compound of formula (I) wherein Q is aminocarbonyl, by reaction with HCOOH, in the presence of a suitable acid, such as hydrochloric acid. A compound of formula (I) wherein Q and $R^2$ are both cyano, can be converted into a compound of formula (I) wherein Q and $R^2$ are both aminocarbonyl by reaction with HCOOH, in the presence of a suitable acid, such as hydrochloric acid. A compound of formula (I) wherein Q is cyano, can also further be converted into a compound of formula (I) wherein Q is tetrazolyl, by reaction with sodium azide in the presence of ammonium chloride and N,N-dimethylacetoacetamide.

Compounds of formula (I) wherein Q is halo can also be converted into a compound of formula (I) wherein Q is mercapto, by reaction with disodium sulfide in the presence of a suitable solvent, such as, for example, 1,4-dioxane.

Compounds of formula (I) wherein Q is halo can also be converted into a compound of formula (I) wherein Q is $C_{1-6}$alkylthio, by reaction with a suitable reagent such as alkaline metal-S—$C_{1-6}$alkyl, e.g. sodium-S—$C_{1-6}$alkyl, in the presence of a suitable solvent, such as N,N-dimethyl sulfoxide. The latter compounds of formula (I) can further be converted into a compound of formula (I) wherein Q is $C_{1-6}$alkyl-S(=O)—, by reaction with a suitable oxidizing agent, such as a peroxide, e.g. 3-chlorobenzenecarboperoxoic acid, in the presence of a suitable solvent, such as an alcohol, e.g. ethanol.

Compounds of formula (I) wherein Q is halo can also be converted into a compound of formula (I) wherein Q is $C_{1-6}$alkyloxy, by reaction with, for example, LiO$C_{1-6}$alkyl, in the presence of a suitable solvent, such as an alcohol, e.g. methanol.

Compounds of formula (I) wherein Q is halo can also be converted into a compound of formula (I) wherein Q is hydroxy, by reaction with a suitable carboxylate ester, e.g. sodium acetate, in a suitable reaction-inert solvent, such as, for example, N,N-dimethyl sulfoxide, followed by treating the obtained reaction product with a suitable base, such as pyridine, and acetyl chloride.

Compounds of formula (I) wherein Q is halo can also be converted into a compound of formula (I) wherein Q represents imidazolyl, thiazolyl, oxazolyl, pyrazolyl, isothiazolyl, isoxazolyl, triazolyl, tetrazolyl optionally substituted with imino, a radical of formula (c), imidazolidinyl, pyrazolidinyl, thiazolidinyl, isothiazolidinyl, oxazolidinyl, isoxazolidinyl optionally substituted with hydroxy, isoxazolidinone, said Q being represented by -$Q_b$, by reaction with H-$Q_b$ in the presence of a suitable base, such as, for example sodium hydroxide, potassium carbonate, sodium hydride, in the presence of a suitable solvent, such as, for example, 1,4-dioxane, N,N-dimethylacetamide, N,N-dimethylformamide Compounds of formula (I) wherein Q is chloro, can be converted into a compound of formula (I) wherein Q is fluoro, by reaction with a suitable fluoride salt, such as for example potassium fluoride, in the presence of a suitable solvent, e.g. sulfolane.

Compounds of formula (I) wherein Q represents $C_{1-6}$alkyloxy$C_{1-6}$alkyl, can be converted into a compound of formula (I) wherein Q represents hydroxy$C_{1-6}$alkyl, by reducing the ether in the presence of a suitable agent, such as, for example, tribromoborane, and a suitable solvent, such as methylene chloride. Compounds of formula (I) wherein Q represents hydroxy$C_{1-6}$alkyl can be converted into a compound of formula (I) wherein Q represents halo$C_{1-6}$alkyl by reaction with a suitable halo-introducing agent, such as for example $SOCl_2$, in the presence of a suitable solvent, such as tetrahydrofuran and a suitable base, such as for example N,N-diethylethanamine. Compounds of formula (I) wherein Q represents halo$C_{1-6}$alkyl can be converted into a compound of formula (I) wherein Q represents mono- or di($C_{1-4}$alkyl)amino$C_{1-6}$alkyl, by reaction with a suitable amine, such as a mono- or di($C_{1-4}$alkyl)amine.

Compounds of formula (I) wherein Q represents $C_{1-6}$alkyloxycarbonyl, can be converted into a compound of formula (I) wherein Q represents aminocarbonyl or mono- or di($C_{1-4}$alkyl)aminocarbonyl by reaction with a suitable agent such as ammonia, $NH_2(C_{1-4}$alkyl), $AlCH_3[N(C_{1-4}$alkyl)$_2$]Cl optionally in the presence of a suitable acid, such as for example hydrochloric acid, and in the presence of a suitable solvent such as an alcohol, e.g. methanol, tetrahydrofuran, N,N-diisopropylethanamine, an alcohol, e.g. methanol. Compounds of formula (I) wherein Q represents $C_{1-6}$alkyloxycarbonyl, can also be converted into a compound of formula (I) wherein Q represents carboxyl by reaction with a suitable base, such as for example LiOH and the like, in the presence of a suitable solvent, such as for example an alcohol, e.g. methanol, and water.

Compounds of formula (I) wherein Q represents carboxyl can be converted into a compound of formula (I) wherein Q represents aminocarbonyl or mono-or di(C1-4alkyl)aminocarbonyl, by reaction with a suitable agent such as ammonia, ammonium chloride, $NH_2(C_{1-4}$alkyl), $AlCH_3[N(C_{1-4}$alkyl)$_2$]Cl in the presence of $SOCl_2$ and a suitable solvent, such as for example N,N-dimethylformamide and water.

Compounds of formula (I) wherein Q is a radical of formula (e-2), wherein $R^9$ is $C_{1-4}$alkylcarbonyl, can be converted into a compound of formula (I) wherein Q is a radical of formula (e-2), wherein $R^9$ is hydrogen, in the presence of a suitable solvent, such as an alcohol, e.g. methanol.

Compounds of formula (I) wherein Y is hydrogen can be converted into a compound wherein Y is halo, by reaction with a suitable halogenating agent, such as, for example $Br_2$ or 1-(chloromethyl)-4-fluoro-1,4-diazoniabicyclo[2,2,2]octane bis[tetrafluoro-borate], in the presence of a suitable solvent, such as tetrahydrofuran, water, acetontrile, chloroform and optionally in the presence of a suitable base such as N,N-diethylethanamine or a suitable acid, such as for example acetic acid. The same type of reaction can be used to introduce a halo atom as $R^2$.

Some of the compounds of formula (I) and some of the intermediates in the present invention may contain an asymmetric carbon atom. Pure stereochemically isomeric forms of said compounds and said intermediates can be obtained by the application of art-known procedures. For example, diastereoisomers can be separated by physical methods such as selective crystallization or chromatographic techniques, e.g. counter current distribution, liquid chromatography and the like methods. Enantiomers can be obtained from racemic mixtures by first converting said racemic mixtures with suitable resolving agents such as, for example, chiral acids, to mixtures of diastereomeric salts or compounds; then physically separating said mixtures of diastereomeric salts or compounds by, for example, selective crystallization or chromatographic techniques, e.g. liquid chromatography and the like methods; and finally converting said separated diastereomeric salts or compounds into the corresponding enantiomers. Pure stereochemically isomeric forms may also be obtained from the pure stereochemically isomeric forms of the appropriate intermediates and starting materials, provided that the intervening reactions occur stereospecifically.

An alternative manner of separating the enantiomeric forms of the compounds of formula (I) and intermediates involves liquid chromatography, in particular liquid chromatography using a chiral stationary phase.

Some of the intermediates and starting materials are known compounds and may be commercially available or may be prepared according to art-known procedures or some of the compounds of formula (I) or the described intermediates may be prepared according to the procedures described in EP-0834507, WO99/50250, WO99/50256, WO 00/27825 and WO 00/27828.

Intermediates of formula (II) wherein L is —$X^1$—$R^3$ or —$X^2$-Alk-$R^4$, said L being represented by -$L_b$, and said intermediates being represented by formula (II-a), can be prepared by reacting an intermediate of formula (IV) wherein each $W^1$ is as defined previously, with an intermediate of formula (VIII) in the presence of a suitable solvent such as, for example, 1,4-dioxane, 2-propanol, acetone or the like, and in the presence of a suitable base such as, for example, N,N-diethylethanamine or N,N-diisopropylethanamine, $K_2CO_3$, NaI or the like.

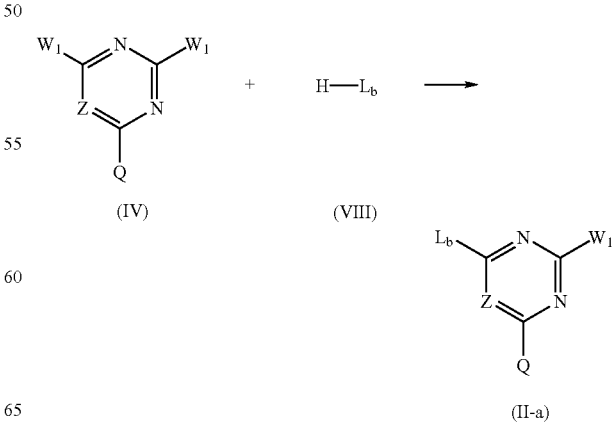

Intermediates of formula (II) wherein Q is Het, said intermediates being represented by formula (II-b), can be prepared by reacting an intermediate of formula (II-c) wherein $W_1$ is as previously defined, with H-Het in the presence of a suitable solvent, such as for example N,N-dimethylacetamide and a suitable base, such as for example dipotassium carbonate.

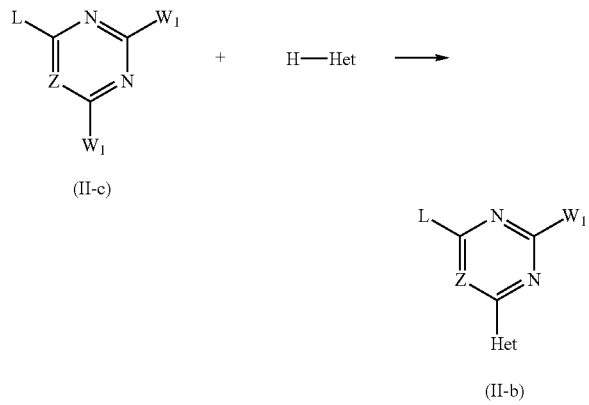

Intermediates of formula (VI) can be prepared by reacting an intermediate of formula (IV-a) wherein $W_2$ is a suitable leaving group such as, for example, a halogen, with an intermediate of formula (III) in the presence of a suitable solvent such as, for example, 1-methyl-2-pyrrolidinone, 1,4-dioxane, tetrahydrofuran or the like, in the presence of a suitable acid such as, for example, 1 N hydrochloric acid in diethyl ether or a suitable base, such as for example N,N-diethylethanamine. This reaction can be performed at a temperature ranging between 50° C. and 250° C.

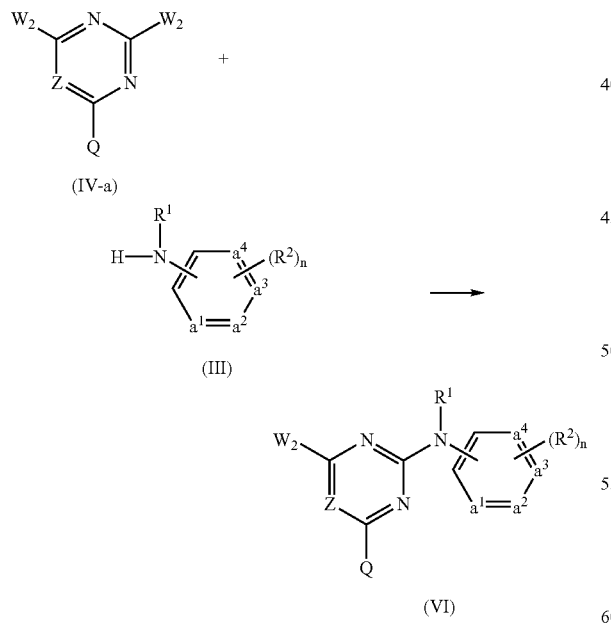

Alternatively, intermediates of formula (VI) can be prepared by reacting an intermediate of formula (XII) with a leaving group introducing agent of formula (XI), wherein $W_2$ represents the leaving group and R represents the remaining of the leaving group introducing agent, an example of a suitable leaving group introducing agent of formula (XI) is phosphorous oxychloride. The reaction can be performed under a reaction-inert atmosphere such as, for example, oxygen free argon or nitrogen and at a temperature ranging between 20° C. and 150° C.

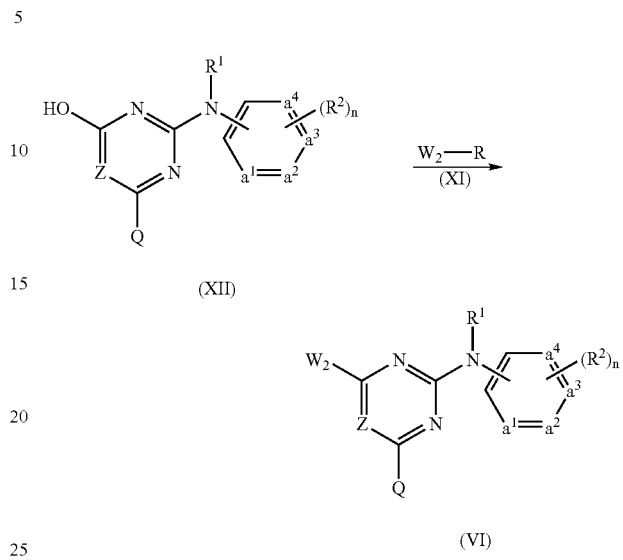

Intermediates of formula (XII) can be prepared by reacting an intermediate of formula (XIII) or a functional derivative thereof, with an intermediate of formula (III). This reaction may be performed under solvent-free conditions or in an appropriate solvent such as, for example, diglyme, tetraline or the like under a reaction-inert atmosphere such as, for example, oxygen free argon or nitrogen, and optionally in the presence of a base such as, for example, sodium hydride, potassium hydride or the like. This reaction can be performed at a temperature ranging between 100° C. and 250° C.

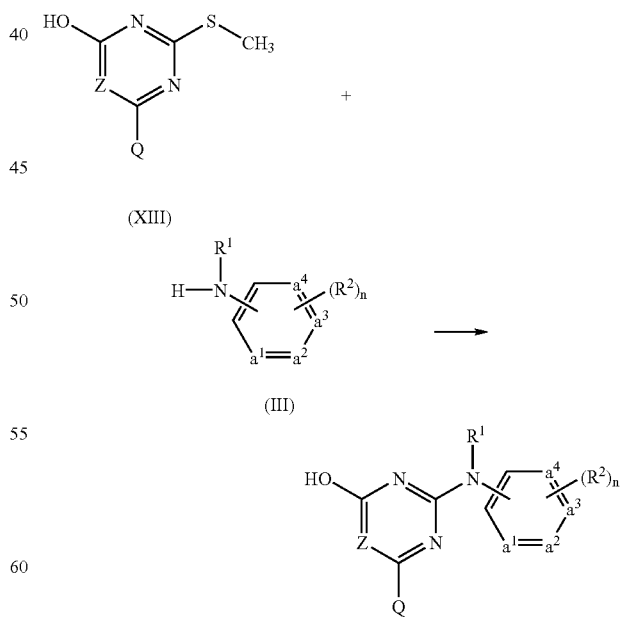

Intermediates of formula (XII) can also be prepared by reacting an intermediate of formula (XIV) wherein $W_3$ is a suitable leaving group, such as for example $C_{1-6}$alkyloxy, and Z and Q are as defined for a compound of formula (I), with an intermediate of formula (XV) in an appropriate solvent such as an alcohol, for example ethanol, or the like, and in the presence of a suitable base such as, for example, sodium ethoxide or the like, under a reaction-inert atmosphere such as, for example, oxygen free argon or nitrogen. The reaction can be performed at a temperature ranging between 20° C. and 125° C.

prepared by reacting an intermediate of formula (XVII) with an intermediate of formula (XVIII) wherein $W_5$ is a suitable leaving group, such as for example phenoxy, in a suitable solvent, such as for example N,N-dimethylformamide.

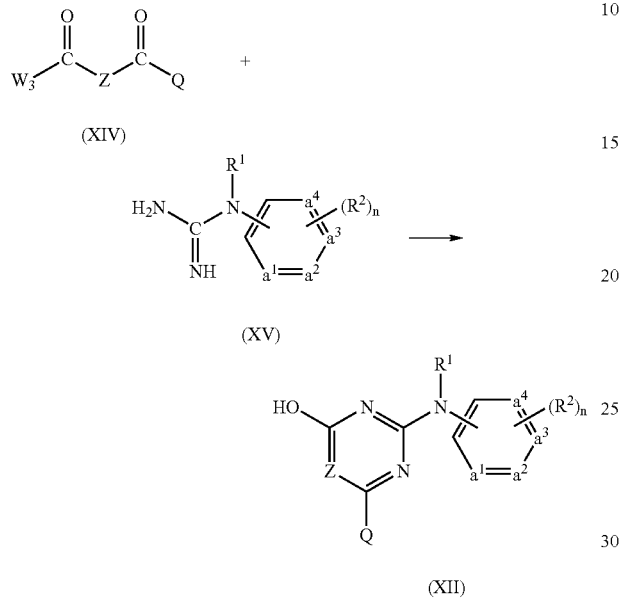

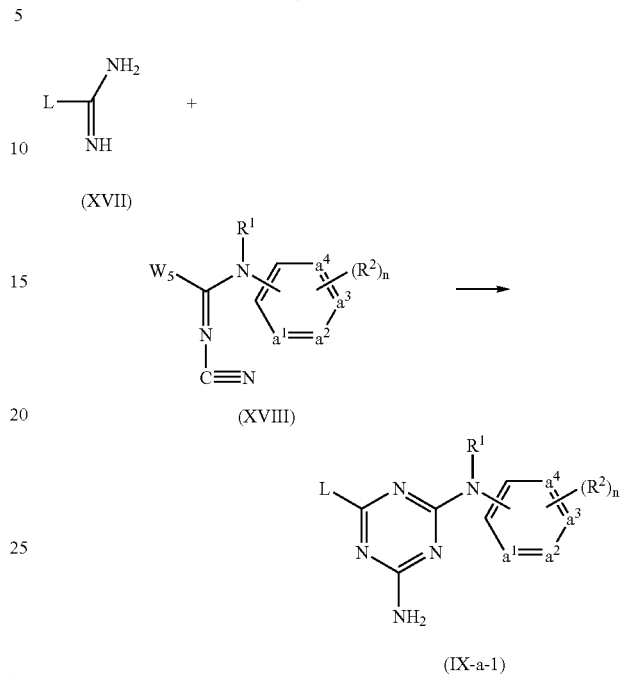

A convenient way of preparing an intermediate of formula (VI) wherein Z is C—Y and Y is a bromine or chloro atom, said intermediates being represented by formula (VI-a), involves the introduction of a bromine or chloro atom to an intermediate of formula (XVI), wherein $W_2$ is as previously defined, using N-bromosuccinimide or N-chlorosuccinimide in a reaction-inert solvent such as, for example, chloroform, carbon tetrachloride or the like. This reaction can be performed at a temperature ranging between 20° C. and 125° C.

Intermediates of formula (XVIII) can be prepared by reacting an intermediate of formula (XIX) with an intermediate of formula (XX) in the presence of a suitable solvent, such as for example N,N-dimethylformamide, under a reaction-inert atmosphere such as, for example, oxygen free argon or nitrogen, preferably at elevated temperatures.

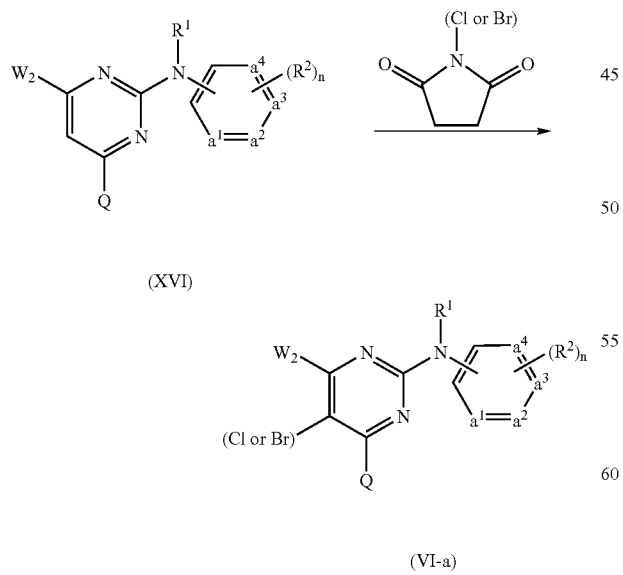

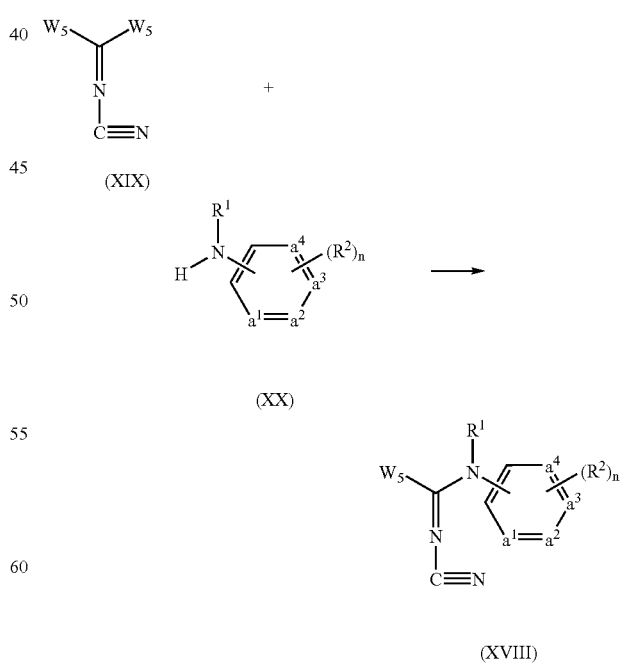

Intermediates of formula (IX-a) wherein Z is N, said intermediates being represented by formula (IX-a-1), can be Intermediates of formula (IX-b) wherein -$A_3$-$A_4$-represents —CH═CH—, said intermediates being represented by formula (IX-b-1), can be prepared by reacting an intermediate of formula (XXI) with 2,5-furandione in the presence of a suitable solvent, such as for example tetrahydrofuran.

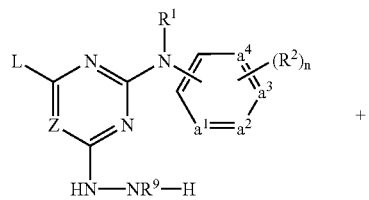

(XXI)

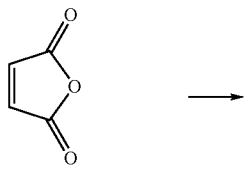

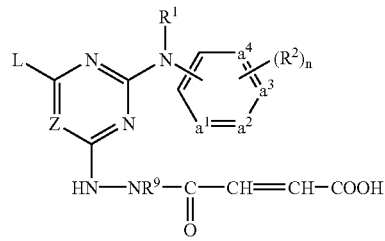

(IX-b-1)

9le;2qIntermediates of formula (IX-c) can be prepared by reacting a compound of formula (I-g) with an intermediate of formula (XXII) in the presence of a suitable solvent, such as for example pyridine or an alkanol, e.g. ethanol and the like, and a suitable base, such as for example sodium hydroxide.

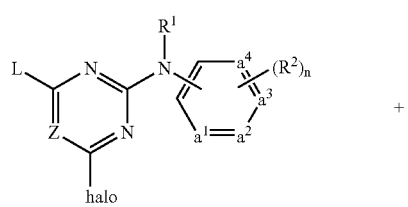

(I-g)

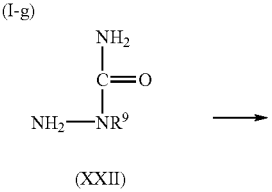

(XXII)

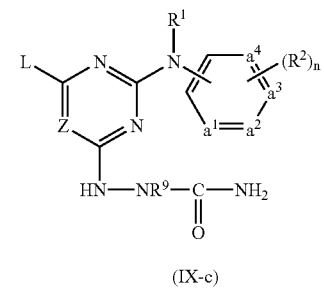

(IX-c)

Intermediates of formula (XXIII) can be prepared by hydrolyzing an intermediate of formula (XXVI) in the presence of a suitable acid, such as hydrochloric acid and the like, and a suitable solvent, such as for example dioxane.

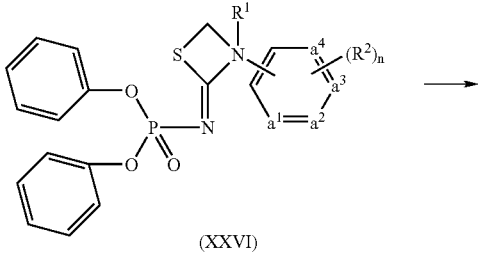

(XXVI)

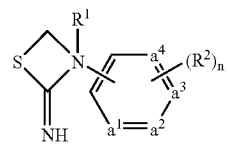

(XXIII)

Intermediates of formula (XXVI) can be prepared by cyclizing an intermediate of formula (XXVII) in the presence of diiodo-methane and in the presence of a suitable base such as $K_2CO_3$ and a suitable solvent, such as for example 2-propanone.

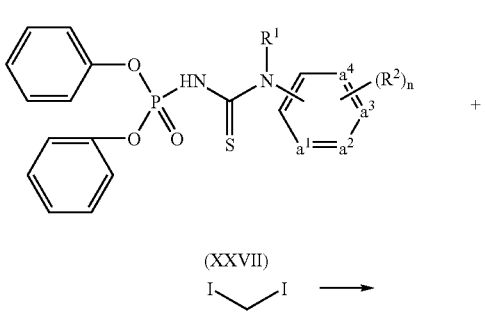

(XXVII)

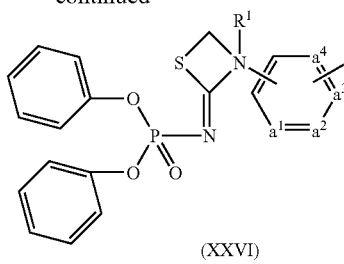

(XXVI)

Intermediates of formula (XXVII) can be prepared by reacting an intermediate of formula (III) with phosphor (isothiocyanatidic) acid, diphenyl ester in the presence of a suitable solvent, such as for example methylene chloride.

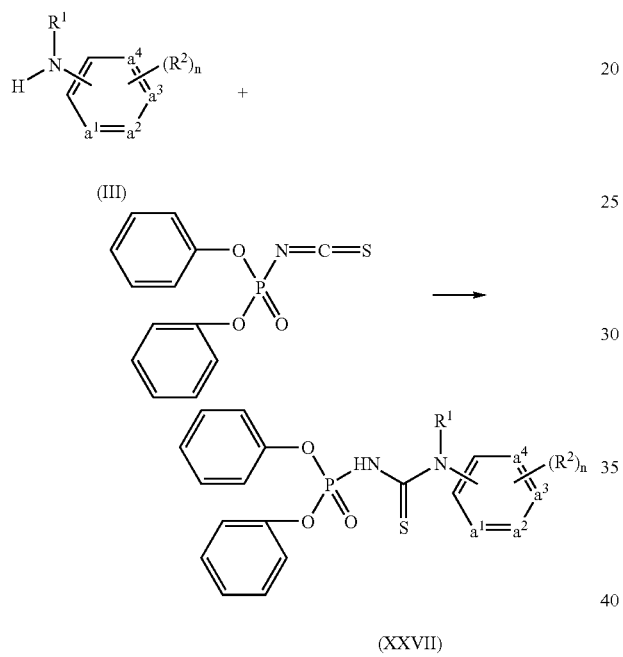

(XXVII)

The compounds of formula (I) as prepared in the hereinabove described processes may be synthesized as a mixture of stereoisomeric forms, in particular in the form of racemic mixtures of enantiomers which can be separated from one another following art-known resolution procedures. The racemic compounds of formula (I) may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials.

It will be appreciated by those skilled in the art that in the processes described above the functional groups of intermediate compounds may need to be blocked by protecting groups.

Functional groups which it is desirable to protect include hydroxy, amino and carboxylic acid. Suitable protecting groups for hydroxy include trialkylsilyl groups (e.g. tert-butyldimethylsilyl, tert-butyldiphenylsilyl or trimethylsilyl), benzyl and tetrahydropyranyl. Suitable protecting groups for amino include tert-butyloxycarbonyl or benzyloxycarbonyl. Suitable protecting groups for carboxylic acid include $C_{1-6}$alkyl or benzyl esters.

The protection and deprotection of functional groups may take place before or after a reaction step.

The use of protecting groups is fully described in 'Protective Groups in Organic Chemistry', edited by J W F McOmie, Plenum Press (1973), and 'Protective Groups in Organic Synthesis' $2^{nd}$ edition, T W Greene & P G M Wutz, Wiley Interscience (1991).

The compounds of formula (I) and (I') show antiretroviral properties (reverse transcriptase inhibiting properties), in particular against Human Immunodeficiency Virus (HIV), which is the aetiological agent of Acquired Immune Deficiency Syndrome (AIDS) in humans. The HIV virus preferentially infects human T-4 cells and destroys them or changes their normal function, particularly the coordination of the immune system. As a result, an infected patient has an everdecreasing number of T-4 cells, which moreover behave abnormally. Hence, the immunological defense system is unable to combat infections and neoplasms and the HIV infected subject usually dies by opportunistic infections such as pneumonia, or by cancers. Other conditions associated with HIV infection include thrombocytopaenia, Kaposi's sarcoma and infection of the central nervous system characterized by progressive demyelination, resulting in dementia and symptoms such as, progressive dysarthria, ataxia and disorientation. HIV infection further has also been associated with peripheral neuropathy, progressive generalized lymphadenopathy (PGL) and AIDS-related complex (ARC).

The present compounds also show activity against multi drug resistant HIV strains, in particular multi drug resistant HIV-1 strains, more in particular the present compounds show activity against HIV strains, especially HIV-1 strains, that have acquired resistance to art-known non-nucleoside reverse transcriptase inhibitors. Art-known non-nucleoside reverse transcriptase inhibitors are those non-nucleoside reverse transcriptase inhibitors other than the present compounds. The present compounds also have little or no binding affinity to human α-1 acid glycoprotein.

Due to their antiretroviral properties, particularly their anti-HIV properties, especially their anti-HIV-1-activity, the compounds of formula (I) or (I'), their N-oxides, pharmaceutically acceptable addition salts, quaternary amines and stereochemically isomeric forms thereof, are useful in the treatment of individuals infected by HIV and for the prophylaxis of these infections. In general, the compounds of the present invention may be useful in the treatment of warm-blooded animals infected with viruses whose existence is mediated by, or depends upon, the enzyme reverse transcriptase. Conditions which may be prevented or treated with the compounds of the present invention, especially conditions associated with HIV and other pathogenic retroviruses, include AIDS, AIDS-related complex (ARC), progressive generalized lymphadenopathy (PGL), as well as chronic CNS diseases caused by retroviruses, such as, for example HIV mediated dementia and multiple sclerosis.

The compounds of the present invention or any subgroup thereof may therefore be used as medicines against abovementioned conditions. Said use as a medicine or method of treatment comprises the systemic administration to HIV-infected subjects of an amount effective to combat the conditions associated with HIV and other pathogenic retroviruses, especially HIV-1. In particular, the compounds of formula (I) or (I') may be used in the manufacture of a medicament for the treatment or the prevention of HIV infections.

In view of the utility of the compounds of formula (I) or (I'), there is provided a method of treating warm-blooded animals, including humans, suffering from or a method of preventing warm-blooded animals, including humans, to suffer from viral infections, especially HIV infections. Said method comprises the administration, preferably oral administration, of an effective amount of a compound of formula (I) or (I'), a N-oxide form, a pharmaceutically acceptable addition salt, a quaternary amine or a possible stereoisomeric form thereof, to warm-blooded animals, including humans.

The present invention also provides compositions for treating viral infections comprising a therapeutically effective amount of a compound of formula (I) or (I') and a pharmaceutically acceptable carrier or diluent.

The compounds of the present invention or any subgroup thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, particularly, for administration orally, rectally, percutaneously, or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, diluents, lubricants, binders, disintegrating agents and the like in the case of powders, pills, capsules, and tablets. Because of their ease in administration, tablets and capsules represent the most advantageous oral dosage unit forms, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations which are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment. The compounds of the present invention may also be administered via inhalation or insufflation by means of methods and formulations employed in the art for administration via this way. Thus, in general the compounds of the present invention may be administered to the lungs in the form of a solution, a suspension or a dry powder. Any system developed for the delivery of solutions, suspensions or dry powders via oral or nasal inhalation or insufflation are suitable for the administration of the present compounds.

To aid solubility of the compounds of formula (I) or (I'), suitable ingredients, e.g. cyclodextrins, may be included in the compositions. Appropriate cyclodextrins are α-, β-, γ-cyclodextrins or ethers and mixed ethers thereof wherein one or more of the hydroxy groups of the anhydroglucose units of the cyclodextrin are substituted with $C_{1-6}$alkyl, particularly methyl, ethyl or isopropyl, e.g. randomly methylated β-CD; hydroxy$C_{1-6}$alkyl, particularly hydroxyethyl, hydroxy-propyl or hydroxybutyl; carboxy$C_{1-6}$alkyl, particularly carboxymethyl or carboxy-ethyl; $C_{1-6}$alkylcarbonyl, particularly acetyl. Especially noteworthy as complexants and/or solubilizers are β-CD, randomly methylated β-CD, 2,6-dimethyl-β-CD, 2-hydroxyethyl-β-CD, 2-hydroxyethyl-γ-CD, 2-hydroxypropyl-γ-CD and (2-carboxymethoxy)propyl-β-CD, and in particular 2-hydroxypropyl-β-CD (2-HP-β-CD).

The term mixed ether denotes cyclodextrin derivatives wherein at least two cyclodextrin hydroxy groups are etherified with different groups such as, for example, hydroxypropyl and hydroxyethyl.

The average molar substitution (M.S.) is used as a measure of the average number of moles of alkoxy units per mole of anhydroglucose. The average substitution degree (D.S.) refers to the average number of substituted hydroxyls per anhydroglucose unit. The M.S. and D.S. value can be determined by various analytical techniques such as nuclear magnetic resonance (NMR), mass spectrometry (MS) and infrared spectroscopy (IR). Depending on the technique used, slightly different values may be obtained for one given cyclodextrin derivative. Preferably, as measured by mass spectrometry, the M.S. ranges from 0.125 to 10 and the D.S. ranges from 0.125 to 3.

Other suitable compositions for oral or rectal administration comprise particles consisting of a solid dispersion comprising a compound of formula (I) or (I') and one or more appropriate pharmaceutically acceptable water-soluble polymers.

The term "a solid dispersion" used hereinafter defines a system in a solid state (as opposed to a liquid or gaseous state) comprising at least two components, in casu the compound of formula (I) or (I') and the water-soluble polymer, wherein one component is dispersed more or less evenly throughout the other component or components (in case additional pharmaceutically acceptable formulating agents, generally known in the art, are included, such as plasticizers, preservatives and the like). When said dispersion of the components is such that the system is chemically and physically uniform or homogenous throughout or consists of one phase as defined in thermo-dynamics, such a solid dispersion will be called "a solid solution". Solid solutions are preferred physical systems because the components therein are usually readily bioavailable to the organisms to which they are administered. This advantage can probably be explained by the ease with which said solid solutions can form liquid solutions when contacted with a liquid medium such as the gastro-intestinal juices. The ease of dissolution may be attributed at least in part to the fact that the energy required for dissolution of the components from a solid solution is less than that required for the dissolution of components from a crystalline or microcrystalline solid phase.

The term "a solid dispersion" also comprises dispersions which are less homogenous throughout than solid solutions. Such dispersions are not chemically and physically uniform throughout or comprise more than one phase. For example, the term "a solid dispersion" also relates to a system having domains or small regions wherein amorphous, microcrystalline or crystalline compound of formula (I) or (I'), or amorphous, microcrystalline or crystalline water-soluble polymer, or both, are dispersed more or less evenly in another phase comprising water-soluble polymer, or compound of formula (I) or (I'), or a solid solution comprising compound of formula (I) or (I') and water-soluble polymer. Said domains are regions within the solid dispersion distinctively marked by some physical feature, small in size, and evenly and randomly distributed throughout the solid dispersion.

Various techniques exist for preparing solid dispersions including melt-extrusion, spray-drying and solution-evaporation.

The solution-evaporation process comprises the following steps:
a) dissolving the compound of formula (I) or (I') and the water-soluble polymer in an appropriate solvent, optionally at elevated temperatures;
b) heating the solution resulting under point a), optionally under vacuum, until the solvent is evaporated. The solution may also be poured onto a large surface so as to form a thin film, and evaporating the solvent therefrom.

In the spray-drying technique, the two components are also dissolved in an appropriate solvent and the resulting solution is then sprayed through the nozzle of a spray dryer followed by evaporating the solvent from the resulting droplets at elevated temperatures.

The preferred technique for preparing solid dispersions is the melt-extrusion process comprising the following steps:
a) mixing a compound of formula (I) or (I') and an appropriate water-soluble polymer,
b) optionally blending additives with the thus obtained mixture,
c) heating and compounding the thus obtained blend until one obtains a homogenous melt,
d) forcing the thus obtained melt through one or more nozzles; and
e) cooling the melt till it solidifies.

The terms "melt" and "melting" should be interpreted broadly. These terms not only mean the alteration from a solid state to a liquid state, but can also refer to a transition to a glassy state or a rubbery state, and in which it is possible for one component of the mixture to get embedded more or less homogeneously into the other. In particular cases, one component will melt and the other component(s) will dissolve in the melt thus forming a solution, which upon cooling may form a solid solution having advantageous dissolution properties.

After preparing the solid dispersions as described hereinabove, the obtained products can be optionally milled and sieved.

The solid dispersion product may be milled or ground to particles having a particle size of less than 600 μm, preferably less than 400 μm and most preferably less than 125 μm.

The particles prepared as described hereinabove can then be formulated by conventional techniques into pharmaceutical dosage forms such as tablets and capsules.

It will be appreciated that a person of skill in the art will be able to optimize the parameters of the solid dispersion preparation techniques described above, such as the most appropriate solvent, the working temperature, the kind of apparatus being used, the rate of spray-drying, the throughput rate in the melt-extruder The water-soluble polymers in the particles are polymers that have an apparent viscosity, when dissolved at 20° C. in an aqueous solution at 2% (w/v), of 1 to 5000 mPa·s more preferably of 1 to 700 mPa·s, and most preferred of 1 to 100 mPa·s. For example, suitable water-soluble polymers include alkylcelluloses, hydroxyalkylcelluloses, hydroxyalkyl alkylcelluloses, carboxyalkylcelluloses, alkali metal salts of carboxyalkylcelluloses, carboxyalkylalkylcelluloses, carboxyalkylcellulose esters, starches, pectines, chitin derivates, di-, oligo- and polysaccharides such as trehalose, alginic acid or alkali metal and ammonium salts thereof, carrageenans, galactomannans, tragacanth, agar-agar, gummi arabicum, guar gummi and xanthan gummi, polyacrylic acids and the salts thereof, polymethacrylic acids and the salts thereof, methacrylate copolymers, polyvinylalcohol, polyvinylpyrrolidone, copolymers of polyvinylpyrrolidone with vinyl acetate, combinations of polyvinylalcohol and polyvinylpyrrolidone, polyalkylene oxides and copolymers of ethylene oxide and propylene oxide. Preferred water-soluble polymers are hydroxypropyl methylcelluloses.

Also one or more cyclodextrins can be used as water soluble polymer in the preparation of the above-mentioned particles as is disclosed in WO 97/18839. Said cyclodextrins include the pharmaceutically acceptable unsubstituted and substituted cyclodextrins known in the art, more particularly α, β or γ cyclodextrins or the pharmaceutically acceptable derivatives thereof.

Substituted cyclodextrins which can be used to prepare the above described particles include polyethers described in U.S. Pat. No. 3,459,731. Further substituted cyclodextrins are ethers wherein the hydrogen of one or more cyclodextrin hydroxy groups is replaced by $C_{1-6}$alkyl, hydroxy$C_{1-6}$alkyl, carboxy-$C_{1-6}$alkyl or $C_{1-6}$alkyloxycarbonyl-$C_{1-6}$alkyl or mixed ethers thereof. In particular such substituted cyclodextrins are ethers wherein the hydrogen of one or more cyclodextrin hydroxy groups is replaced by $C_{1-3}$alkyl, hydroxy$C_{2-4}$alkyl or carboxy$C_{1-2}$alkyl or more in particular by methyl, ethyl, hydroxyethyl, hydroxypropyl, hydroxybutyl, carboxy-methyl or carboxyethyl.

Of particular utility are the β-cyclodextrin ethers, e.g. dimethyl-β-cyclodextrin as described in Drugs of the Future, Vol. 9, No. 8, p. 577-578 by M. Nogradi (1984) and polyethers, e.g. hydroxypropyl β-cyclodextrin and hydroxyethyl β-cyclodextrin, being examples. Such an alkyl ether may be a methyl ether with a degree of substitution of about 0.125 to 3, e.g. about 0.3 to 2. Such a hydroxypropyl cyclodextrin may for example be formed from the reaction between β-cyclodextrin an propylene oxide and may have a MS value of about 0.125 to 10, e.g. about 0.3 to 3.

Another type of substituted cyclodextrins is sulfobutyl-cyclodextrines.

The ratio of the compound of formula (I) or (I') over the water soluble polymer may vary widely. For example ratios of 1/100 to 100/1 may be applied. Interesting ratios of the compound of formula (I) or (I') over cyclodextrin range from about 1/10 to 10/1. More interesting ratios range from about 1/5 to 5/1.

It may further be convenient to formulate the compounds of formula (I) or (I') in the form of nanoparticles which have a surface modifier adsorbed on the surface thereof in an amount sufficient to maintain an effective average particle size of less than 1000 nm. Useful surface modifiers are believed to include those which physically adhere to the surface of the compound of formula (I) or (I') but do not chemically bond to said compound.

Suitable surface modifiers can preferably be selected from known organic and inorganic pharmaceutical excipients. Such excipients include various polymers, low molecular weight oligomers, natural products and surfactants. Preferred surface modifiers include nonionic and anionic surfactants.

Yet another interesting way of formulating the compounds of formula (I) or (I') involves a pharmaceutical composition whereby the compounds of formula (I) or (I') are incorporated in hydrophilic polymers and applying this mixture as a coat film over many small beads, thus yielding a composition which can conveniently be manufactured and which is suitable for preparing pharmaceutical dosage forms for oral administration.

Said beads comprise a central, rounded or spherical core, a coating film of a hydrophilic polymer and a compound of formula (I) or (I') and optionally a seal-coating layer.

Materials suitable for use as cores in the beads are manifold, provided that said materials are pharmaceutically acceptable and have appropriate dimensions and firmness. Examples of such materials are polymers, inorganic substances, organic substances, and saccharides and derivatives thereof.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

Those of skill in the treatment of HIV-infection could determine the effective daily amount from the test results presented here. In general it is contemplated that an effective daily amount would be from 0.01 mg/kg to 50 mg/kg body weight, more preferably from 0.1 mg/kg to 10 mg/kg body weight. It may be appropriate to administer the required dose as two, three, four or more sub-doses at appropriate intervals throughout the day. Said sub-doses may be formulated as unit dosage forms, for example, containing 1 to 1000 mg, and in particular 5 to 200 mg of active ingredient per unit dosage form.

The exact dosage and frequency of administration depends on the particular compound of formula (I) or (I') used, the particular condition being treated, the severity of the condition being treated, the age, weight and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention. The effective daily amount ranges mentioned hereinabove are therefore only guidelines and are not intended to limit the scope or use of the invention to any extent.

The present compounds of formula (I) or (I') can be used alone or in combination with other therapeutic agents, such as anti-virals, antibiotics, immunomodulators or vaccines for the treatment of viral infections. They may also be used alone or in combination with other prophylactic agents for the prevention of viral infections. The present compounds may be used in vaccines and methods for protecting individuals against viral infections over an extended period of time. The prodrugs may be employed in such vaccines either alone or together with other compounds of this invention or together with other anti-viral agents in a manner consistent with the conventional utilization of reverse transcriptase inhibitors in vaccines. Thus, the present compounds may be combined with pharmaceutically acceptable adjuvants conventionally employed in vaccines and administered in prophylactically effective amounts to protect individuals over an extended period of time against HIV infection.

Also, the combination of an antiretroviral compound and a compound of formula (I) or (I') can be used as a medicine. Thus, the present invention also relates to a product containing (a) a compound of formula (I) or (I'), and (b) another antiretroviral compound, as a combined preparation for simultaneous, separate or sequential use in anti-HIV treatment. The different drugs may be combined in a single preparation together with pharmaceutically acceptable carriers. Said other antiretroviral compounds may be known antiretroviral compounds such as suramine, pentamidine, thymopentin, castanospermine, dextran (dextran sulfate), foscarnet-sodium (trisodium phosphono formate); nucleoside reverse transcriptase inhibitors, e.g. zidovudine (3'-azido-3'-deoxythymidine, AZT), didanosine (2',3'-dideoxyinosine; ddI), zalcitabine (dideoxycytidine, ddC) or lamivudine (2'-3'-dideoxy-3'-thiacytidine, 3TC), stavudine (2',3'-didehydro-3'-deoxythymidine, d4T), abacavir and the like; non-nucleoside reverse transciptase inhibitors such as nevirapine (11-cyclopropyl-5,11-dihydro-4-methyl-6H-dipyrido[3,2-b: 2',3'-e][1,4]diazepin-6-one), efavirenz, delavirdine, TMC-120, TMC-125 and the like; compounds of the TIBO (tetrahydro-imidazo[4,5,1-jk][1,4]-benzodiazepine-2(1H)-one and thione)-type e.g. (S)-8-chloro-4,5,6,7-tetrahydro-5-methyl-6-(3-methyl-2-butenyl)imidazo-[4,5,1-jk][1,4]benzodiazepine-2(1H)-thione; compounds of the α-APA (α-anilino phenyl acetamide) type e.g. α-[(2-nitrophenyl)amino]-2,6-dichlorobenzene-acetamide and the like; inhibitors of trans-activating proteins, such as TAT-inhibitors, e.g. RO-5-3335, or REV inhibitors, and the like; protease inhibitors e.g. indinavir, ritonavir, saquinavir, lopinavir (ABT-378), nelfinavir, amprenavir, TMC-126, BMS-232632, VX-175 and the like; fusion inhibitors, e.g. T-20, T-1249, AMD-3100 and the like; inhibitors of the viral integrase; nucleotide reverse transcriptase inhibitors, e.g. tenofovir and the like; ribonucleotide reductase inhibitors, e.g. hydroxyurea and the like.

By administering the compounds of the present invention with other anti-viral agents which target different events in the viral life cycle, the therapeutic effect of these compounds can be potentiated. Combination therapies as described above exert a synergistic effect in inhibiting HIV replication because each component of the combination acts on a different site of HIV replication. The use of such combinations may reduce the dosage of a given conventional antiretroviral agent which would be required for a desired therapeutic or prophylactic effect as compared to when that agent is administered as a monotherapy. These combinations may reduce or eliminate the side effects of conventional single anti-retroviral therapy while not interfering with the anti-viral activity of the agents. These combinations reduce potential of resistance to single agent therapies, while minimizing any associated toxicity. These combinations may also increase the efficacy of the conventional agent without increasing the associated toxicity.

The compounds of the present invention may also be administered in combination with immunomodulating agents, e.g. levamisole, bropirimine, anti-human alpha interferon antibody, interferon alpha, interleukin 2, methionine enkephalin, diethyldithiocarbamate, tumor necrosis factor, naltrexone and the like; antibiotics, e.g. pentamidine isethiorate and the like; or cholinergic agents, e.g. tacrine, rivastigmine, donepezil, galantamine and the like to prevent or combat infection and diseases or symptoms of diseases associated with HIV infections, such as AIDS and ARC, e.g. dementia. A compound of formula (I) or (I') can also be combined with another compound of formula (I) or (I').

Although the present invention focuses on the use of the present compounds for preventing or treating HIV infections, the present compounds may also be used as inhibitory agents for other viruses which depend on similar reverse transcriptases for obligatory events in their life cycle.

The following examples are intended to illustrate the present invention. Hereinafter, THF means tetrahydrofuran and DMF means N,N-dimethylformamide.

Experimental Part

As described hereinbelow, DMF stands for N,N-dimethylformamide; THF stands for tetrahydrofuran; HPLC stands for High Performance Liquid Chromatography.

Preparation of the Intermediate Compounds

EXAMPLE A1 a) Reaction under argon flow. A mixture of 4-aminobenzonitrile (0.0210 mol) and diphenyl N-cyano-carbonimidate (0.0210 mol) in DMF (25 ml) was stirred for 20 hours at 110° C. Water was added and the resulting precipitate was filtered off, to give a brownish solid. This fraction was recrystallized from CH₃CN. The precipitate was filtered off and dried. Yield: 1.67 g of phenyl N'-cyano-N-(4-cyanophenyl)-carbamimidate (interm. 1) (30%).

b) Reaction under argon flow. Intermediate (1) (0.00634 mol) was added to a solution of 2,6-dichlorobenzeneethanimidamide (0.00634 mol) in DMF (13 ml). The reaction mixture was stirred for three days at room temperature, then for two days at 60° C. Water was added and the resulting precipitate was filtered off, to give a pure white solid. This fraction was refluxed in CH₃CN (500 ml), cooled and the precipitate was filtered off and dried. Yield: 1.58 g of 4-[[4-amino-6-[(2,6-dichlorophenyl)methyl]-1,3,5-triazin-2-yl]amino]benzonitrile (interm. 2) (67%) (mp. 278-279° C.).

EXAMPLE A2 a) Preparation of Intermediate (3)

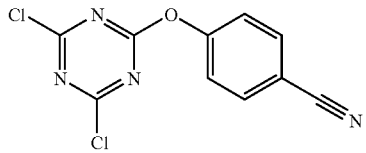

Reaction under argon atmosphere. 2,4,6-Trichloro-1,3,5-triazine (0.07440 mol) and THF (100 ml) were combined and cooled to −75° C. Then, 4-aminobenzonitrile (0.07440 mol) was added and the solution was stirred for 4 hours. Then, N,N-diethylethanamine (0.07440 mol)) was added dropwise and the reaction mixture was allowed to warm up slowly to room temperature and stirred for 3 days. After adding 1,4-dioxane (100 ml), the resulting precipitate was collected by filtration, washed with THF, and dried. Yield: 12.74 g of intermediate (3).

b) Preparation of Intermediate (9)

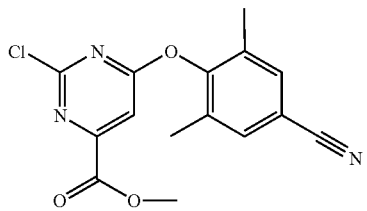

1.6 g (7.73 mmol) of 2-chloro-4-chloro-pyrimidine-6-carboxy methyl ester and 1.19 g (1.05 equiv.) of 4-hydroxy-3,5-dimethyl benzonitrile were dissolved in 20 ml of acetone and 1.28 g (1.2 equiv.) of K₂CO₃ and 58 mg (5 mol %) of NaI were added. The reaction was stirred at 20° C. overnight. After that the reaction mixture is cooled to 0° C. and filtered off. Acetone is evaporated and the residue is dissolved in ethyl acetate and washed with saturated aqueous NaHCO₃/H₂O 1/1. The organic layer was washed with brine, dried over Na₂SO₄ and evaporated. The residue was stirred in diisopropyl ether and the product was filtered off, the diisopropyl ether solution was cooled to 0° C. and more product was filtered off and dried. Yield: 2.16 g of intermediate (9) (88%).

EXAMPLE A3

Preparation of Intermediate (4)

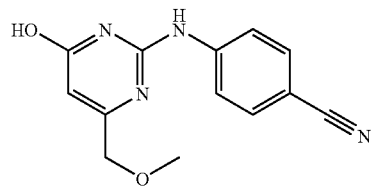

a) Ethanol (140 ml) was dried over sodium and distilled. Ethanol and sodium (0.0611 mol) were combined and stirred until homogeneous. N-(4-cyanophenyl)-guanidine monohydrochloride (0.05995 mol) and methyl 4-methoxy-3-oxobutanoate (0.05995 mol) were added. The mixture was stirred and refluxed for 5 hours and cooled to room temperature. The mixture was poured into a mixture of water (450 ml) and HOAc (50 ml). The mixture was stirred for 3 hours, filtered, washed with water, and air dried to produce 10.95 g white solid. The solid was dried at 95° C. overnight at 0.2 mm Hg. Yield: 10.19 g of intermediate (4) (66.4%) (264-265° C.).

b) Preparation of Intermediate (5)

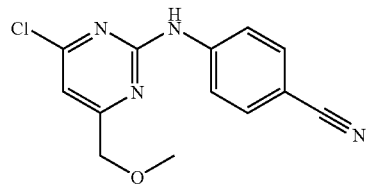

Intermediate (4) (0.0234 mol) was stirred and refluxed in POCl₃ (30 ml) for 20 minutes. The mixture was poured onto ice and filtered to yield 10.09 g off-white solid. The sample was dried at 80° C. for 16 hours at 0.2 mm Hg. Yield: 6.27 g of intermediate (5) (97.6%) (174-176° C.).

EXAMPLE A4

Preparation of Intermediate (6)

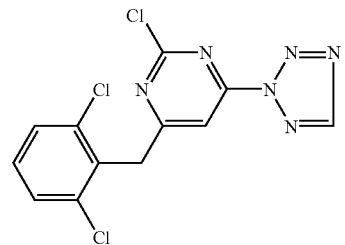

2,4-Dichloro-6-[(2,6-dichlorophenyl)methyl]pyrimidine (2 mmol), 1H-tetrazole (2 mmol), N,N-dimethylacetamide (20 ml) and K₂CO₃ (3.6 mol) were combined. The reaction mixture was stirred at 5° C. for 2 days. The mixture was poured to 5% HCl (50 ml) and then to ethyl acetate (50 ml). The layers were separated. The organic layer was extracted with brine (50 ml), dried over sodium sulfate, filtered, and the filtrate was concentrated. The product was purified by gradient elution from Silica gel 60 column (0-20% ethyl acetate in hexane). The desired fractions were collected and the solvent was evaporated. White solid was recrystallized from ethanol. Yield: 0.15 g of intermediate (6) (mp.: 167-169° C.).

EXAMPLE A5

Preparation of intermediate (7)

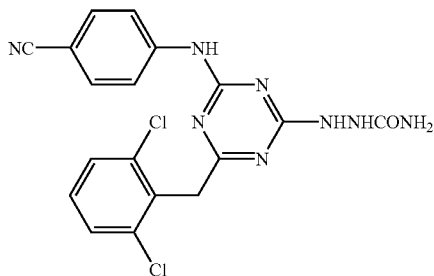

Hydrazinecarboxamide hydrochloride (0.0013 mol) was dissolved in boiling EtOH (50 ml), then was added NaOH (0.0013 mol), pyridine (0.0013 mol) and compound (1) (0.0013 mol). The mixture was refluxed for 6 hours. White solid obtained was separated via suction, brought in boiling methanol and dioxane and dried. Yield: 0.48 g of intermediate (7) (mp.: 149.5-252° C.).

EXAMPLE A6

Preparation of Intermediate (8)

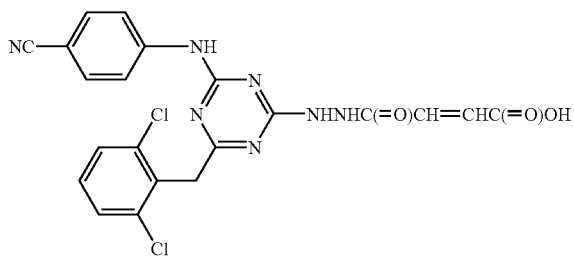

2,5-Furandione (3 mmol) was added to the solution of 4-[[4-[(2,6-dichlorophenyl)methyl]-6-hydrazino-1,3,5-triazin-2-yl]amino]benzonitrile (A) (2 mmol) in THF (40 ml). The THF solution was stirred for about 2 hours at room temperature. The 100% conversion of (A) to intermediate (8) was confirmed by HPLC. Then THF was removed in vacuum. The raw product was added to absolute ethanol (30 ml) and this heterogenous mixture was refluxed for about 5 minutes. The solid was filtered off, washed with hot chloroform (ca. 20 ml) and dried. Yield: 0.6 g of intermediate (8) (mp.: 229-231° C.).

EXAMPLE A7 a) Preparation of Intermediate (10)

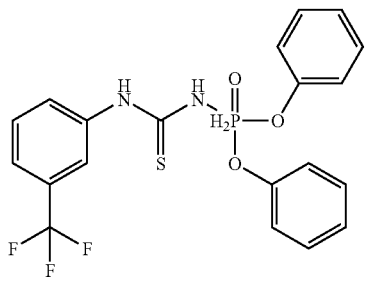

Phosphor(isothiocyanatidic) acid, diphenyl ester (0.155 mol) was stirred in CH₂Cl₂ (300 ml). 3-(trifluoromethyl)-benzenamine (0.155 mol) was added dropwise and the reaction mixture was stirred overnight at room temperature. The mixture was poured out into water and this mixture was stirred for 15 minutes. The layers were separated. The organic layer was washed with water, dried, filtered and the solvent was evaporated. The residue was triturated under diisopropyl ether, filtered off and dried. Yield: 45 g of interm. (10) (64%).

b) Preparation of Intermediate (11)

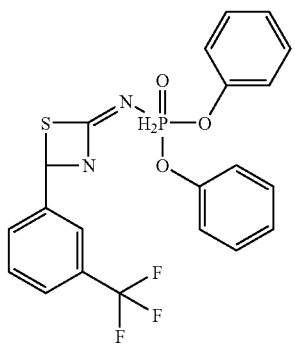

A mixture of interm. (10) (0.0995 mol) and K₂CO₃ (0.4 mol) in 2-propanone (500 ml) was stirred at room temperature. Diiodo-methane (0.2 mol) was added and the reaction mixture was stirred overnight. The mixture was filtered and the filtrate was evaporated. The residue was purified by column chromatography over silica gel (eluent: CH₂Cl₂/CH₃OH 99/10. The product fractions were collected and the solvent was evaporated. Yield: 42.3 g of interm. (11) (91.6%).

c) Preparation of Intermediate (12)

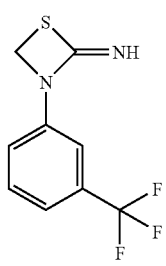

A mixture of interm. (11) (0.069 mol) in HCl 36% (300 ml) and dioxane (300 ml) was stirred overnight at 40° C. and the solvent was evaporated. The residue was triturated under CH₃CN, filtered off and dried. Yield: 13.8 g of interm. (12) (86.2%).

Preparation of the Final Compounds

EXAMPLE B1 a-1) 2,4-Dichloro-6-[(2,6-dichlorophenyl)methyl]-1,3-5-triazine (0.71 mol) was stirred in toluene (2200 ml) to obtain white suspension (I). N-ethyl-N-(1-methylethyl)-2-propanamine (124 ml) was added to a suspension of 4-aminobenzonitrile (0.71 mol) in THF (2200 ml), giving solution (II). Solution (II) was added dropwise to (I) over 105 minutes at 24-28° C. (water bath). The resulting reaction mixture was stirred overnight at room temperature. Water (2 liter) was added. The separated organic layer was washed twice with water (1.5 liter), and part of the solvent was evaporated. The product crystallized out, was filtered off and dried (vacuum, 40° C., 20 hours). Yield: 235.4 g of 4-[[4-chloro-6-[(2,6-dichlorophenyl)methyl]-1,3,5-triazin-2-yl]amino]-benzonitrile (85%) (compound 1) (243-244° C.).

a-2) Preparation of Compound 69

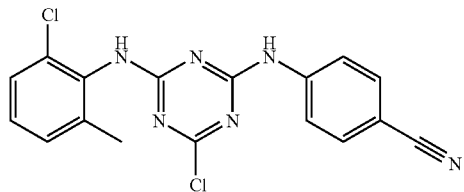

Reaction under argon flow. N-ethyl-N-(1-methylethyl)-2-propanamine (0.00714 mol) was added to a solution of 2-chloro-6-methylbenzenamine (0.00714 mol) in 1,4-dioxane (20 ml). A solution of intermediate (3) (0.00714 mol) in 1,4-dioxane (5 ml) was added. The reaction mixture was stirred and refluxed for 24 hours. The solvent was evaporated. CH₂Cl₂ was added. The organic layer was washed with a saturated aqueous NaHCO₃ solution, and the resulting precipitate was filtered off. Yield: 0.56 g of compound 69 (21.1%, white solid).

a-3) Preparation of Compound 70

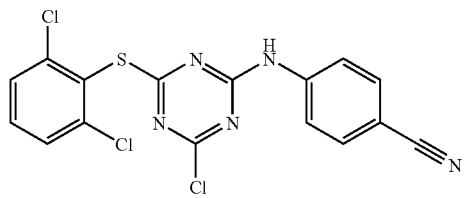

N-ethyl-N-(1-methylethyl)-2-propanamine (0.00752 mol) was added to intermediate (3) (0.00752 mol) in 1,4-dioxane (150 ml), under Argon. 2,6-Dichlorobenzenethiol (0.00752 mol) was added to this mixture, which was then stirred at room temperature for 16 hours. The solvent was evaporated, and the residue was dissolved in ethyl acetate, washed with NaHCO₃ and brine, then dried over Na₂SO₄, filtered and the filtrate was evaporated. This fraction was recrystallized from CH₃CN (250 ml). The filtrate from recrystallization was concentrated to approximately 50 ml, cooled, and filtered. Yield: 0.85 g of compound 70 (28%, white solid, used in next reaction step, without further purification) (268-269° C.).

a-4) Preparation of Compound 24

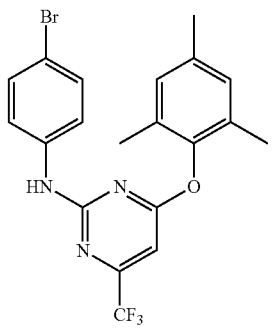

In a flask of 25 ml with magnetic stirring and cooling

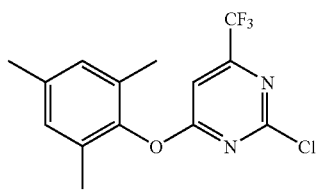

(1.9 mmol) and bromoaniline (4.74 mmol) (2.5 eq.) were added in ethanol (5 ml). The mixture was refluxed for 24 hours. The solvent was evaporated. The residu was dissolved in 5 ml ether and 5 ml H₂O. The layers were separated. The aqueous layer was washed 3 times with ether. The organic layers were dried over Na₂SO₄. Yield: 1.2 g of compound 24. b) Reaction under argon atmosphere. A small portion of 2-(bromomethyl)-1,3-dichloro-benzene in diethylether (40 ml) was added to Mg (0.0813 mol) in diethylether (80 ml). Once the Grignard started to form, the solution of 2-(bromomethyl)-1,3-dichloro-benzene (0.0813 mol) in diethylether (40 ml) was added at a rate that kept the solution refluxing. The solution was stirred at room temperature for 2 hours and, then, added to a solution of 2,4,6-trichloro-1,3,5-triazine (0.0531 mol) in benzene (80 ml) at 0° C. The resulting solution was stirred at 0° C. for 1 hour and, then, at room temperature for 2 hours followed by the addition of 4-aminobenzonitrile (0.0542 mol) in 1,4-dioxane (100 ml). The reaction mixture was stirred at room temperature for 16 hours. Then, N,N-diethylethanamine (0.0542 mol) was added, and the reaction mixture was stirred further at room temperature. The reaction mixture was quenched with H₂O, extracted with ethyl acetate, washed with brine (3×), and dried over K₂CO₃, filtered and the solvent was evaporated. The residue was treated with CH₂Cl₂ and the resulting precipitate was collected by filtration. Yield: 6.99 g of fraction 1 (an off-white solid). The collection of precipitate from subsequent filtrations yielded: 1.80 g of fraction 2 and 1.30 g of fraction 3. Fraction 3 was purified by flash column chromatography over silica gel (eluent: CH₂Cl₂). The desired fractions were collected and the solvent was evaporated. The residue was treated with CH₂Cl₂, filtered off and dried. Yield: 1.47 g of fraction 4.

Fractions 1, 2 and 4 were combined and treated with CH₃CN (600 ml). The solvent was evaporated and the residue was dried under vacuum at 80° C. and 2.0 mm Hg for 16 hours. The residue was treated with CH₃CN (300 ml), filtered off and dried (2×). The product was dried under vacuum at 100° C. and 0.2 mm Hg for 16 hours. Yield: 2.87 g of 4-[[4-chloro-6-[(2,6-dichlorophenyl)methyl]-1,3,5-triazin-2-yl]amino]-benzonitrile (14.3%); (compound 1) (mp.: 243-244° C.).

c) Preparation of Compound 71

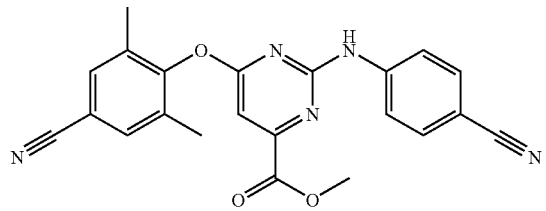

Intermediate (9)

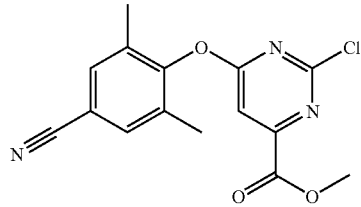

(prepared according to A2b)) (0.00737 mol), 4-aminobenzonitrile (0.01511 mol), and 1-methyl-2-pyrrolidinone (5 ml) were added to a pressure vessel under argon. The mixture was heated at 125-130° C. for 7 hours, and the heat was removed. Water, then ether were added. The mixture was stirred and filtered. The filtrate was stirred for 6 hours, and filtered. The filtrate was filtered again. This filtrate was evaporated, then extracted with CH₂Cl₂. This sample was purified by preparative HPLC (gradient of 0.1% trifluoroacetic acid in water and 0.1% trifluoroacetic acid in CH₃CN). Yield: 0.20 g of compound 71 (white powder) (mp.: 258-259° C.).

d) Preparation of Compound 39

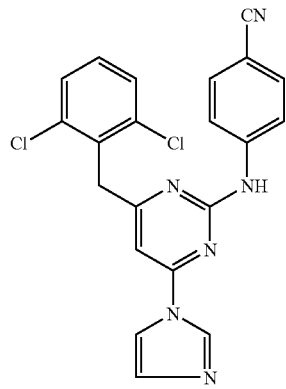

To a solution of

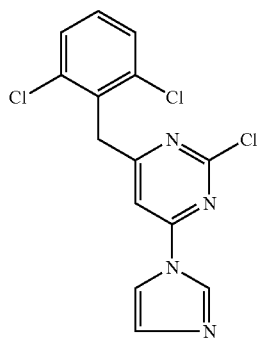

,4-aminobenzonitrile and 2-methyl-2-propanol in dry dioxane was added catalysator Pd(PPh₃)₄. The solution was heated to 100° C. with stirring until 2-chloro-4-[(2,6-dichlorophenyl)methyl]-6-(1-imidazolyl)-pyrimidine had been completely consumed. The solution was then cooled to room temperature, taken up in ether (30 ml), and washed with brine (15 ml). The organic layer was dried over anhydrous sodium sulfate, filtered and concentrated. The crude product was then suspended in 15% HCl and the solid was filtered off. The crude product was purified by gradient elution from Silica gel 60 column (0-25% acetone in hexane). Yield: compound 39 (mp.: 275-285° C.).

e) Preparation of Compound 43

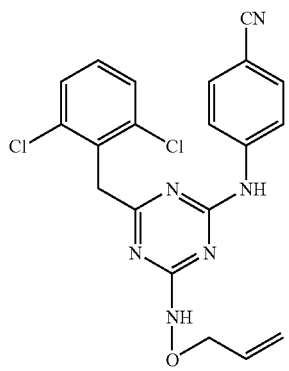

Compound 1 (0.001 mol) and O-2-propenyl-hydroxylamine (0.0022 mol) were dissolved in 1,4-dioxane (3 ml) in a sealable tube, and NaOH 3M (0.002 mol) was added. The tube was flushed with argon, sealed, and heated for 2 hours to 95° C., and cooled to room temperature. The solvent was evaporated at 60° C. under a strong nitrogen flow, and the residue was purified by reverse phase HPLC. The product fractions were collected and the solvent was evaporated. Yield: 0.330 g of compound 43 (77.3%, white solid) (mp.: 225-227° C.).

EXAMPLE B2 a) Preparation of Compound 2

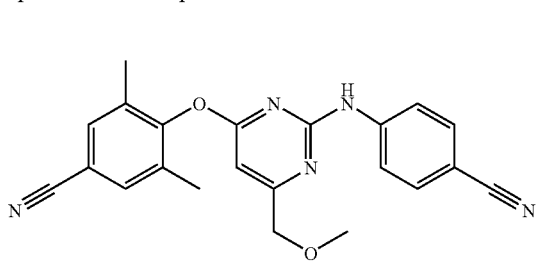

NaH (0.00120 mol) was added to a solution of intermediate (5) (0.00109 mol), 4-hydroxy-3,5-dimethylbenzonitrile (0.00120 mol), 1,4-dioxane (15 ml) and 1-methyl-2-pyrrolidinone (15 ml) in a flask under argon. After the gas evolution ceased, the reaction was heated in an oil bath at 135-140° C. for 16 hours. The solvent was evaporated, acetonitrile added, the precipitate filtered and washed with cold CH$_3$CN to give 3.95 g of fraction 1. The filtrate was filtered to give 0.46 g of fraction 2. The solids were combined and chromatographed on silica gel eluting with 0 and 1% methanol:methylene chloride to give 3.25 g of white solid. This solid was stirred in refluxing CH$_3$CN and filtered to give 2.56 g of compound (2) (mp.: 203-204° C.).

b) Preparation of Compound 72

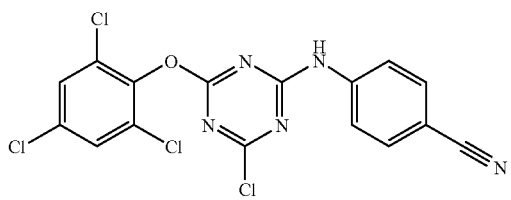

A solution of 2,4,6-trichlorophenol (0.0075 mol) in dry THF (35 ml) was added dropwise over 30 minutes. to a suspension of cleaned NaH (0.0075 mol) in dry THF (5 ml). After 30 minutes of stirring (some effervescence), the mixture was a clear solution, and intermediate (3) (0.0076 mol) was added in one portion followed by additional THF (40 ml). The heterogeneous mixture was stirred over the weekend. More NaH (0.09 g) was added in one portion and the reaction mixture was stirred for 18 hours. The reaction was quenched by pouring into 250 ml of ice. A precipitate formed. The sample and filtrate were treated with ethyl acetate and the layers were separated. The aqueous pH was adjusted with 1 M NaOH and re-extraction was performed. The basic aqueous fraction was then extracted further with ethyl acetate and the combined organic fractions were dried (MgSO$_4$), filtered and the solvent was evaporated in vacuo. The residue was purified by flash column chromatography over silica gel (eluent: 100% CH$_2$Cl$_2$). Two pure fraction groups were collected. The appropriate di-addition fractions were combined to afford 0.28 g of off-white solid which was triturated under diethyl ether, then dried. The appropriate mono-addition fractions were combined and, when needed, recrystallized from ethyl acetate. The obtained residue was purified by chromatography. Yield: 1.28 g of compound 72 (mp.: 238-239° C.).

c) Preparation of Compound 60

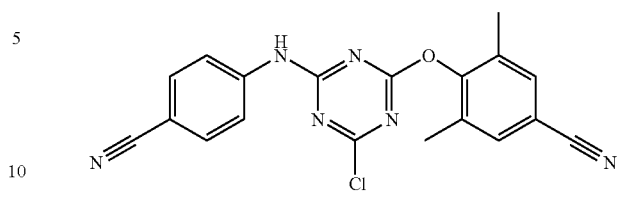

NaOH (0.0036 mol) was added to a solution of 4-hydroxy-3,5-dimethylbenzonitrile in acetone (3.6 ml). The product

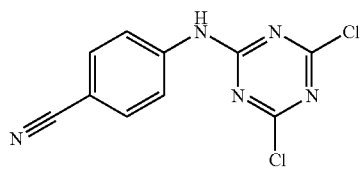

was suspended in acetone/H$_2$O (50 ml). The solution of 4-hydroxy-3,5-dimethylbenzonitrile was added to the suspension and mixed overnight at laboratory temperature. The reaction mixture was diluted with water to 100 ml and neutralised by acetic acid. The crude product was separated by filtration, dried in air and crystallised from chloroform. Yield: 1.04 g (92%) of compound 60 (mp. 260-265° C.).

EXAMPLE B3

Preparation of Compound 3

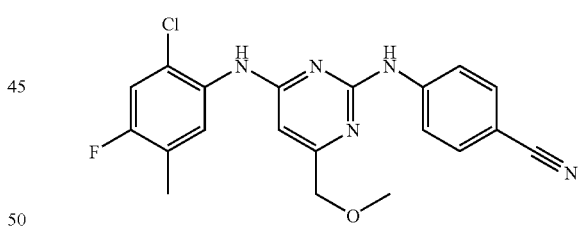

Reaction in a pressure flask under argon. A mixture of intermediate (5) (0.00364 mol), 2-chloro-4-fluoro-5-methylbenzenamine (0.00401 mol), N-ethyl-N-(1-methylethyl)-2-propanamine (0.00401 mol) and 1-methyl-2-pyrrolidinone (2 ml) in 1,4-dioxane (3 ml) was heated in an oil bath at 140° C. for 3 days. The heat was increased to 160-165° C., and the mixture was heated for 2 days. The heat was increased to 180-185° C., and the mixture was heated for 4 days. The mixture was poured into H$_2$O, extracted (Et$_2$O), washed with brine, dried (Na$_2$SO$_4$), and evaporated to produce 1.55 g of pale yellow solid. The solid was sonicated in CH$_2$Cl$_2$, filtered and recrystallized from CH$_3$CN to yield 0.32 g of compound (3) (22.1%) (mp.: 213-214° C.).

EXAMPLE B4

Preparation of Compound 4

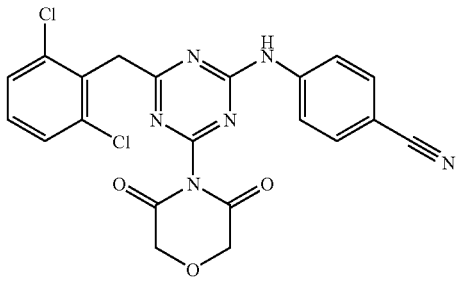

1,4-Dioxane-2,6-dione (0.067 mol) and 4-[[4-amino-6-[(2,6-dichlorophenyl)methyl]-1,3,5-triazin-2-yl]amino]benzonitrile (0.00135 mol) were added to a flask and heated in an oil bath while stirring to give a clear solution. The reaction reached 165° C. in 15 minutes, and was maintained at 165° C. for 35 minutes. The reaction mixture was then removed from the oil bath, cooled to room temperature, then treated between cold water and diethyl ether, using sonication to break up all of the solid mass. The mixture was transferred to a separatory funnel, which gave a quantity of insoluble material. The mixture was suction filtered (collected 0.33 g of white powder) and the filtrate was returned to the funnel. The $Et_2O$ was washed with distilled water until the pH was brought from about 3.0 to neutrality. The mixture was dried over $Na_2SO_4$ to yield 0.24 g of fluffy white wax from the extraction. All material was recombined and purified by flash column chromatography with a solvent coated onto the silica gel using $CH_2Cl_2/CH_3CN$ and a forerun of 250 ml of $CH_2Cl_2$. The solvent was changed to 95:5 $CH_2Cl_2/Et_2O$, then 90:10. The desired fractions were collected and the solvent was evaporated. The residue was recrystallized once more. Yield: 0.090 g of compound (4) (14.2%) (mp.: 268-269° C.).

EXAMPLE B5 a) Preparation of Compound 5

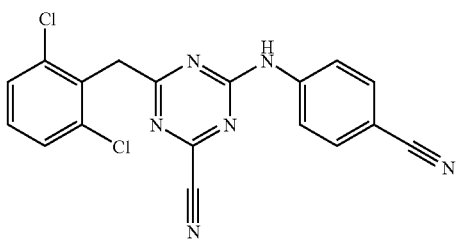

A mixture of compound (1) (0.00768 mol), NaCN (0.00971 mol) and $Pd(PPh_3)_4$ (0.0247 mol) in N,N-dimethylacetamide (200 ml, freshly distilled) was stirred for 40 minutes at 120° C. The reaction mixture was cooled, poured out into ice-cold water and the resulting precipitate was filtered off, washed with water and dried (vacuum). Some impurities were then removed by double extraction with diethyl ether. This fraction (2.70 g) was purified by column chromatography over silica gel (eluent: $CH_2Cl_2/(CH_3OH/NH_3$ satd.) from 100/0 to 90/10). The desired fractions were collected and the solvent was evaporated. Yield: 1.7 g of compound (5) (mp.: 221-230° C.).

b) Preparation of Compound 40

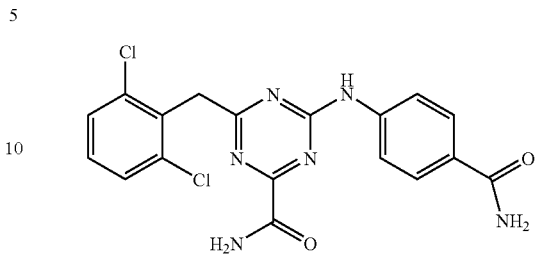

Compound 5 (prepared according to B5a)) was suspended in HCOOH (25 ml) with stirring on a magnetic stirrer. A stream of gas HCL was then passed through the reaction mixture for 1 hour. The mixture was stirred for 20 hours. A product was precipitated by pouring of the reaction mixture into water. Precipitated solid was then filtered off, washed with water and dried in vacuum dryer. Yield: 4.10 g (89.3%) of compound 40 (mp.: 287-295° C.).

c) Preparation of Compound 42

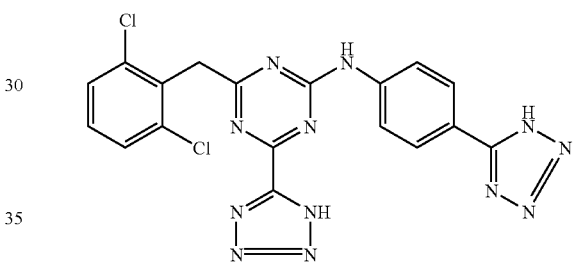

Compound 5 (prepared according to B5a)) (0.0015 mol), $NaN_3$ (0.030 mol), $NH_4Cl$ (0.030 mol) and N,N-dimethylacetoacetamide (15 ml) were combined. The reaction mixture was stirred at 140° C. for 2 hours. The mixture was poured into 150 ml 5% HCl. The crude product was filtered off, washed with cold water and dried. The product was recrystallized from glacial acetic acid. Yield: 0.67 g (96%) of compound 42 (mp.: 249-252° C.).

d) Preparation of Compound 38

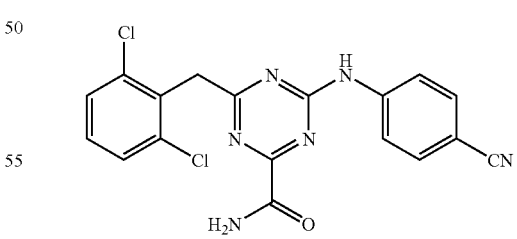

Compound 5 (prepared according B5a)) (5.24 mmol) was suspended in HCOOH (15 ml) with stirring on magnetic stirrer. A stream of gas HCl was then passed through the reaction mixture. The mixture was poured into water after 45 minutes. Precipitated solid was then filtered off, washed with water and dried in vacuum dryer. The crude product (1.91 g) was recrystallized from acetonitrile. Yield: 1.53 g (73.1%) of compound 38 (mp.: 262-263° C.).

e) Preparation of Compound 33

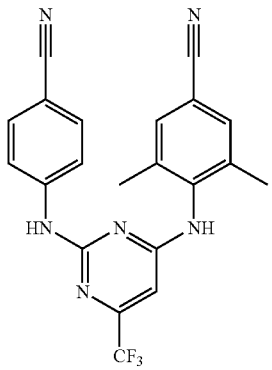

In a flask of 25 ml equipped with magnetic stirring and cooling compound 32 (prepared according to B1c)) (0.47 mmol) and CuCN (2 eq.) were poured into 1-methyl-2-pyrrolidinone (1 ml). The reaction mixture was heated at 150° C. overnight (18 hours.). After cooling, the mixture was diluted with cold $H_2O$ (8 ml) and placed into an icebath for 30 minutes. The precipitate was filtered and washed with ether, carefully triturated and again filtered. Yield: 208 mg of compound 33 (mp.: 249-251° C.).

EXAMPLE B6

Preparation of Compound 6

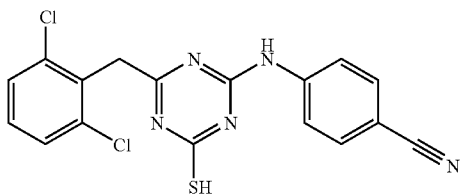

Reaction under argon atmosphere. Sodium sulfide (0.01024 mol) was added to compound (1) (0.00512 mol) in 1,4-dioxane (100 ml). The reaction mixture was stirred at room temperature for three days and the solvent was evaporated. The residue was dissolved in ethyl acetate, washed with 1 N HCl (30 ml), a saturated aqueous sodium bicarbonate solution and with brine, dried with sodium sulfate, filtered, and the solvent was evaporated to give 2.49 g of white solid. This fraction was recrystallized once from acetonitrile to give 0.58 g of fraction 1.

The filtrate was concentrated. The concentrate was cooled and filtered to give 0.59 g of fraction 2. Fractions 1 and 2 were combined and purified by column chromatography over silica gel (eluent: $CH_2Cl_2/CH_3OH$ 100/0, 99/1 and 98/2). The pure fractions were collected and the solvent was evaporated. The residue was recrystallized from acetonitrile.

The precipitate was filtered off and dried (0.2 mm Hg, 80° C., 16 hours). Yield: 0.76 g of compound (6) (38.3%) (mp. 254-255° C.).

EXAMPLE B7 a) Preparation of Compound 7

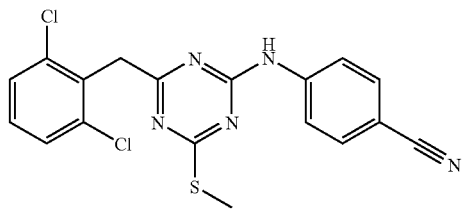

Reaction under argon atmosphere. A mixture of compound (1) (0.00256 mol) and $NaSCH_3$ (0.00269 mol) in dimethylsulfoxide (10 ml) was stirred for 16 hours at room temperature. Water was added and this mixture was extracted with ethyl acetate. The separated organic layer was washed with brine, dried with potassium carbonate, filtered, and the solvent was evaporated. The residue was crystallized from methanol, then recrystallized from acetonitrile. The sample was dried at 80° C., 0.2 mm Hg for 16 hours. Yield: 0.70 g of compound (7) (68.0%) (mp. 184-185° C.).

b) Preparation of Compound 8

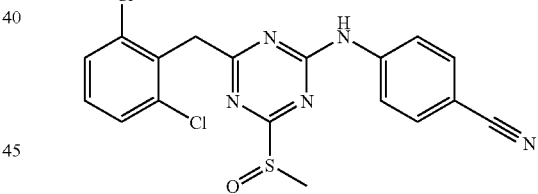

Reaction under argon atmosphere. 3-Chlorobenzenecarboperoxoic acid (0.00373 mol) was added to a solution of compound (7) (0.00249 mol) in ethanol (150 ml). The reaction mixture was stirred at room temperature for 40 minutes, poured into 600 ml of ice water, extracted two times with ethyl acetate, washed with brine, dried with potassium carbonate, filtered and the solvent was evaporated to give an off-white solid. The solid was stirred in 2% methanol:methylene chloride (50 ml) and filtered. The filtrate was purified by column chromatography over silica gel (eluent: $CH_2Cl_2/CH_3OH$ 100/0, 99/1 and 98/2). The desired fractions were collected and the solvent was evaporated to give 0.39 g of product. This fraction was recrystallized from methanol. The precipitate was filtered off and dried. The sample was dried at 80° C., 0.2 mm Hg for 16 hours. Yield: 0.20 g of compound (8) (19.2%) (mp. 219-221° C.).

EXAMPLE B8

Preparation of Compound 9

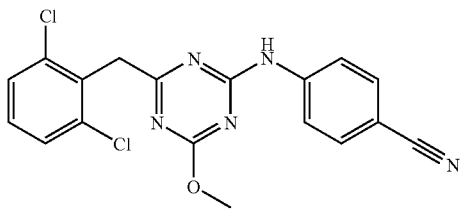

A suspension of compound (1) (0.0205 mol) in methanol (20 ml) was treated with LiOCH$_3$ (0.0021 mol) in one portion and the heterogeneous reaction mixture was stirred vigorously at room temperature for 28 hours. The reaction mixture was diluted with ether and treated with ice cold 1 M HCl. The layers were separated and the acidic aqueous phase was extracted four more times with ether. The combined ether layers were dried over MgSO$_4$/Na$_2$SO$_4$, filtered and the filtrate was evaporated. The residue was recrystallized twice from acetonitrile. The precipitate was filtered off and dried. Yield: 0.43 g of compound (9) (54.3%) (mp. 198-199° C.).

EXAMPLE B9

Preparation of Compound 10

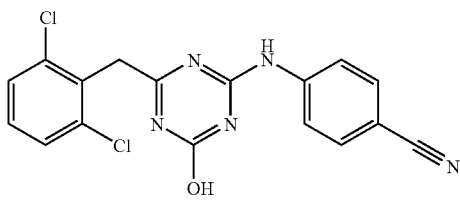

Sodium acetate (0.00463 mol) was added to a solution of compound (1) (0.00153 mol) in dimethylfsulfoxide (15 ml) and the mixture was-stirred for 72 hours at room temperature. The reaction mixture was poured into a 100 ml ice-water slurry which caused a voluminous precipitate to form; the mixture was placed in the refrigerator overnight. The precipitate was filtered off, washed extensively with cold water, then dried to give 1.17 g of white solid. This material was powdered and then triturated with ether to give 0.53 g of white powder. One half (0.26 g) of this material was dissolved in pyridine (5 ml) and treated with acetyl chloride (0.07 ml, 0.00098 mol) in one portion. The reaction mixture was stirred at room temperature for 72 hours, then concentrated in vacuo, and extracted between CH$_2$Cl$_2$ and a saturated aqueous NaHCO$_3$ solution. A voluminous solid was insoluble in either fraction. The triphasic mixture was suction filtered and the collected solid was washed extensively with water, then air-dried. Yield: 0.19 g of compound (10) (mp. >300° C.).

EXAMPLE B10 a) Preparation of Compound 11

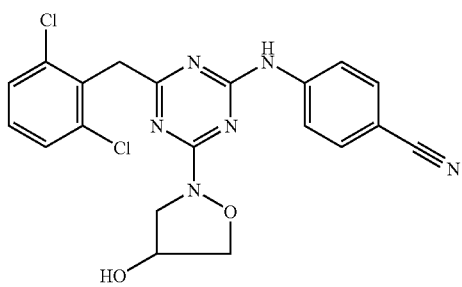

Compound (1) (0.00075 mol) and 4-isoxazolidinol HCl (0.0008 mol) were dissolved in 1,4-dioxane (3 ml) in a sealable tube, and NaOH 3M (0.0018 mol) was added. The tube was flushed with nitrogen, sealed, and heated for 3 hours to 90° C., and cooled to room temperature. Methylene chloride (5 ml) and methanol (2 ml) were added, the tube was shaken vigorously, and the bottom (aqueous) layer was removed with a pipette. The organic layer was dried over potassium carbonate, and the tube was centrifuged. The supernatant was separated and evaporated at 50° C. under a steady nitrogen flow. The residue was purified by reverse phase HPLC. The pure fractions were collected and the solvent was evaporated. Yield: 0.160 g of compound (11) (49.7%) (mp. 175° C.).

b) Preparation of Compound 46

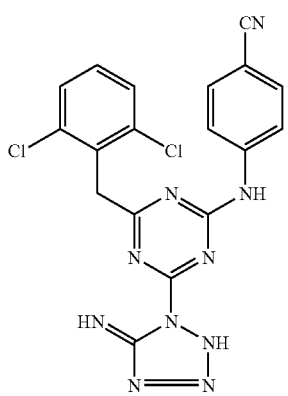

Compound 1 (0.002 mol), 1H-tetrazol-5-amine (0.004 mol), N,N-dimethylacetamide (6 ml) and K$_2$CO$_3$ (0.004 mol) were combined. The reaction mixture was stirred at 120° C. for 60 minutes. Mixture was poured into cold water. A product was filtered off, washed with hot water and dried. The product was crystallized from the mixture of tetrahydrofurane/n-heptane. Yield: 0.79 g (90%) of compound 46 (mp.: 302-304° C.).

EXAMPLE B11 a) Preparation of Compound 12

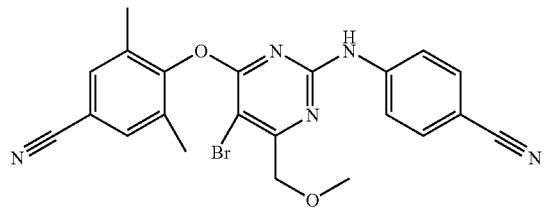

Br$_2$ (0.12523 mol) was added to a solution of compound (2) (0.00475 mol) and THF (55 ml). After 9 hours, N,N-diethylethanamine (1.32 ml), Br$_2$ (0.22 ml), THF (10 ml), and water (10 ml) were added, and the homogeneous clear solution was stirred overnight. Water (100 ml) was added, and the mixture was extracted (ether), washed (water, brine), and dried (K$_2$CO$_3$). The aqueous phase was washed (ether). The ether phase was washed (brine). The organic phases were combined and evaporated to produce 3.75 g white solid. The solid was recrystallized in CH$_3$CN, dried at 80° C. for 16 hours at 0.2 mm Hg to yield 2.19 g of compound (12) (89%) (mp. 198-199° C.).

b) Preparation of Compound 13

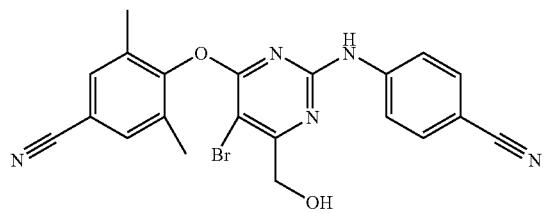

BBr$_3$ in CH$_2$Cl$_2$ (0.01825 mol) was added dropwise over 5 minutes to compound (12) (0.00332 mol) in CH$_2$Cl$_2$ (16 ml) under argon at −78° C. in a dry ice/2-propanol bath. The mixture was stirred at −78° C. for 20 minutes. The bath was replaced with an ice water bath, and the mixture was stirred at 0° C. for 50 minutes. Water and CH$_2$Cl$_2$ were added until the solution became homogeneous. The organic phase was separated and dried (K$_2$CO$_3$). Column chromatography through short path of silica gel (eluent 5% methanol:CH$_2$Cl$_2$) produced 1.71 g off-white solid. The solid was taken up in CH$_2$Cl$_2$, washed (NaHCO$_3$), dried (Na$_2$SO$_4$), and evaporated. The residue was recrystallized in 2-propanol (250 ml) to yield 1.14 g of compound (13) (71.7%) (279-281° C.). The solid was dried at 80° C. for 4 hours at 0.2 mm Hg.

c) Preparation of Compound 73

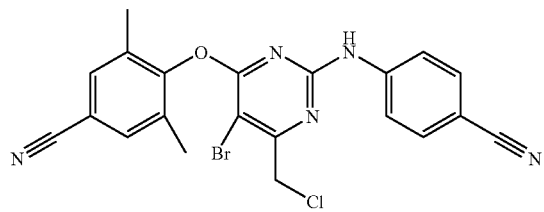

SOCl$_2$ (0.00157 mole) was added to THF (7 ml) and cooled in an ice bath under argon. Compound 13 (prepared according to B11b)) (0.0013 mole) and N,N-diethylethanamine (0.0013 mole) were added in THF (10 ml). The reaction was stirred until the ice melted, and the reaction returned to room temperature. SOCl$_2$ (0.100 ml) was added at room temperature, and the reaction was stirred for 2 hours. More SOCl$_2$ (0.05 ml) was added, and the reaction was stirred for 1.5 hours. The mixture was filtered and the white solid was rinsed with THF. The filtrate was evaporated. Yield 0.600 g of compound 73 (97.9%, light yellow solid) (mp.: 238-240° C.).

d) Preparation of Compound 74

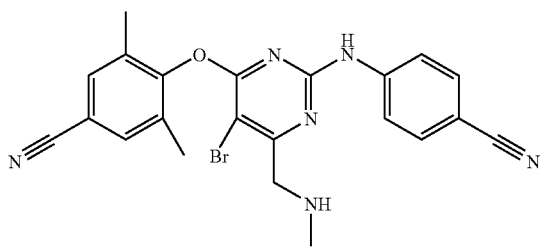

Compound 73 (prepared according to B11c)) (0.000416 mole) was dissolved in methylamine (0.008 mol) in a closed flask and stirred at room temperature for 40 hours. The solvent and excess amine were evaporated. The resulting solid was taken up in ethyl acetate and washed with aqueous NaHCO$_3$ and brine. The organic layer was dried with sodium sulfate and evaporated to give 0.123 g of a yellow solid. The material was recrystallized from ethanol (3×). The solid was dried under vacuum with refluxing toluene overnight. Yield: 0.025 g of compound 74 (13%, yellow orange solid) (mp.: 223-224C.).

EXAMPLE B12

Preparation of

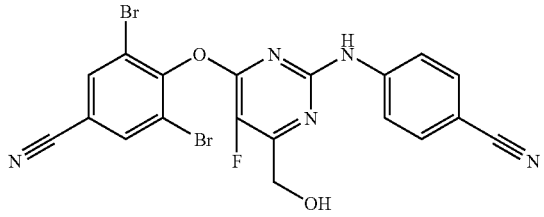

compound 15

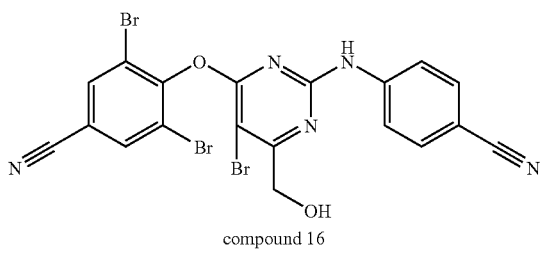

compound 16

-continued

To a flask under argon containing

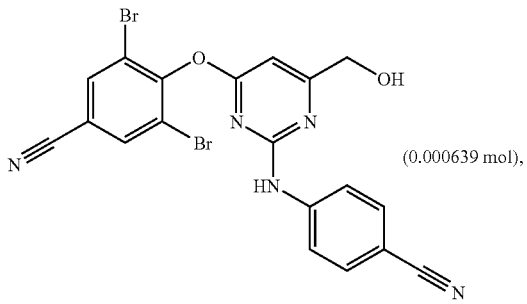

(0.000639 mol), (compound 14) (prepared according to example B11b)), acetonitrile (10 ml), and CHCl₃ (10 mL) was added 1,4-Diazoniabicyclo[2.2.2]octane, 1-(chloromethyl)-4-fluoro-, bis[tetrafluoroborate(1-)] (0.000639 mol). The reaction mixture was refluxed for 15.5 hours, evaporated, dissolved in methylene chloride, washed with water, filtered, dried with potassium carbonate and evaporated. Chromatography on the Gilson Prep LC gave 0.0017 g of compound (15) (0.5%) (240-241° C.) and 0.0097 g of compound (16) (2.6%) (m.p.: 250-251° C.).

EXAMPLE B13

Preparation of Compound 37

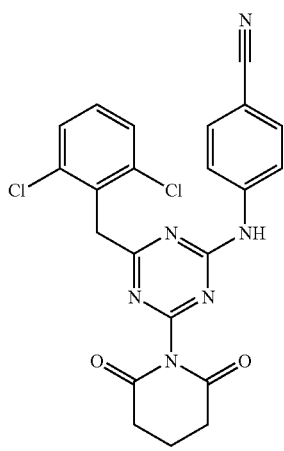

Pentanedioyl dichloride (24 mmol) was added (in portions) to the stirred and refluxed solution of intermediate (2) (6.4 mmol) in dioxane (100 ml). The conversion of intermediate (2) to compound (37) was monitored by HPLC. The reaction mixture was filtered and dioxane was removed in vacuum. The residue obtained was washed with methanol (50 ml) and collected by suction. This solid was purified by slow crystallization from methanol (1000 ml). Yield: 1.09 g (36.5%) of compound (37) (mp. 278-282° C.).

EXAMPLE B14

Preparation of Compound 36

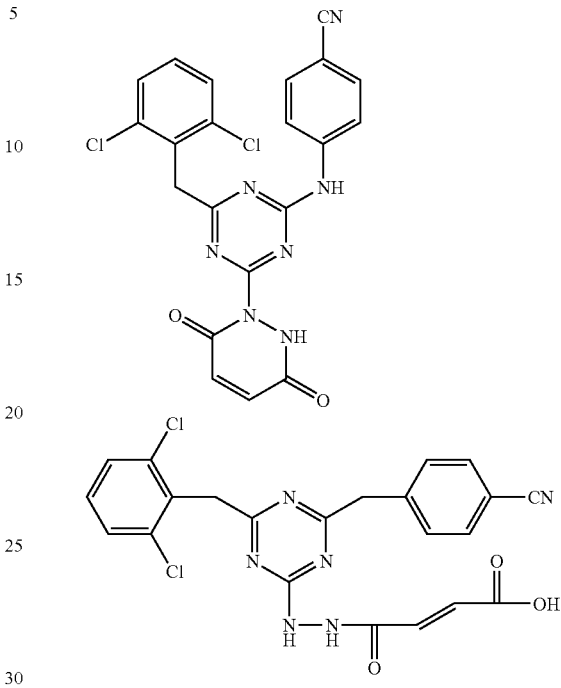

(interm. 8) (2.5 mmol) was added to the suspension of sodium acetate (0.3 g) in acetic acid anhydride (12 ml). The mixture was stirred for 30 minutes at 55° C. The reaction was monitored by HPLC. The reaction mixture was poured into a solution of methanol (8 ml) and stirred for 20 minutes. Precipitated solid was collected by suction, washed with methanol (3 ml) and dried. The raw product was extracted with CHCl₃ (70 ml). The CHCl₃ solution was filtered and concentrated by destillation. Heptane (30 ml) was added to the concentrated CHCl₃ solution (20 ml). The precipitated solid was collected by suction and dried. This solid was finally purified by washing with hot methanol (2×10 ml) and hot acetone (1×3 ml). The solid was collected by suction and dried. Yield: 0.18 g (16%) of compound 36.

EXAMPLE B15

Preparation of Compound 49

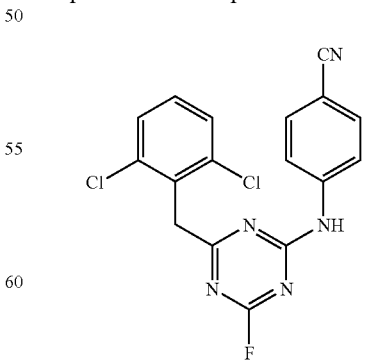

Compound 1 (0.00512 mol) was dissolved in sulfolane (90 ml)(dried, destilled). KF (0.01455 mol) (freshly burnt) was added at 90° C. Reaction was monitored by HPLC analysis. After 8.5 hours the mixture was cooled to laboratory temperature and poured under good mixing into 500 ml of destined water. The precipitate was filtered off and mixed with 500 ml of water and the suspension was sonificated and filtered. This procedure was repeated once more. Finally the solid was washed with 150 ml water and dried in the vacuum dryer at 70° C. Yield: 1.87 g of compound 49 (white solid) (mp.: 199-201° C.).

EXAMPLE B16 a) Preparation of Compound 62

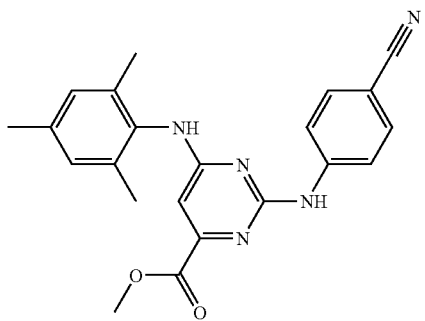

1.00 gram (2.67 mmol) of 2-N-(4-cyanoaniline)-4-N-(2,4,6-trimethylaniline)pyrimidine-6-carboxylic acid was dissolved in 10 ml of MeOH and 1.13 ml (5 equiv.) of dimethylcarbonate and 40 drops of concentrated $H_2SO_4$ were added. The reaction mixture was stirred at 65° C. for 1 week. After that the reaction was quenched with aqueous saturated $NaHCO_3$ and the MeOH was evaproated. The product was extracted with ethyl acetate and the extract was washed with brine, dried over $Na_2SO_4$ and evaporated. The residue was purified by column chromatography ($SiO_2$/ethyl acetate) to afford 579 mg (56%) of compound 62.

b) Preparation of Compound 61

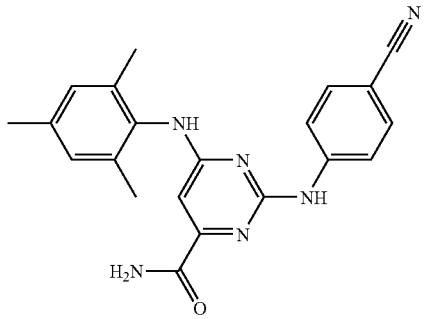

80 mg (0.206 mmol) of compound 62 (prepared according to B16a)) was dissolved in 1.5 ml of dry THF and 1.5 ml of a 7N methanolic solution of $NH_3$ was added. The mixture was stirred at 20° C. overnight. After that the product was filtered off, washed with THF and dried to yield 74 mg (96%) of compound 61.

c) Preparation of Compound 63

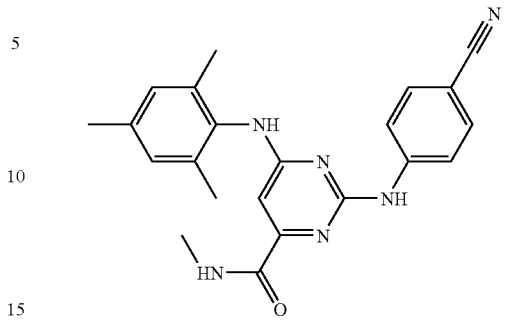

80 mg (0.197 mmol) of compound 62 (prepared according to B16a)) was dissolved in 4 ml THF/MeOH 1/1 and 133 mg (10 eq.) of $H_2NMe.HCl$ and 0.5 ml (15 equiv.) of N,N-diisopropylethanamine were added. The reaction was stirred overnight at 20° C. and after that, the solvents were evaporated. The residue was taken up in ethyl acetate and washed successively with 0.5 N aqueous $KHSO_4$ (2×) and with brine, dried over $Na_2SO_4$ and evaporated. The residue was stirred in n-heptane/diisopropyl ether 1/1 and the product was filtered off and dried to yield 60 mg (75%) of compound 63.

d) Preparation of Compound 66

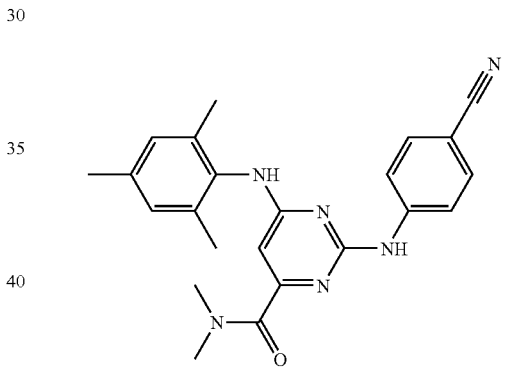

50 mg (0.123 mmol) of compound 62 (prepared according to B16a)) was dissolved in 3 ml of dry THF and 0.200 ml (1.25 equiv.) of

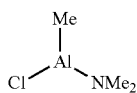

(0.76 M in hexane/toluene) was added. The mixture was stirred overnight at 20° C.; 0.050 ml of

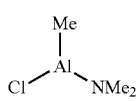

was added and the mixture was stirred for another night. After that the THF was evaporated and the residue was taken up in ethyl acetate and washed successively with saturated

EXAMPLE B17

Preparation of Compound 41

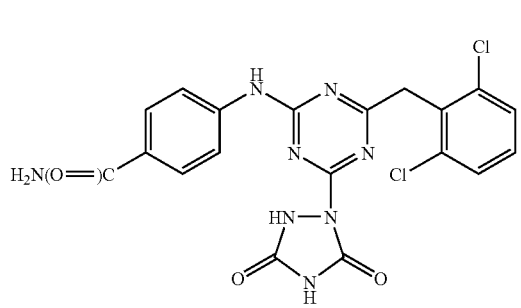

20 ml of solution C(=O)Cl₂ in dioxane (circa 20%) was warmed up to 75° C. Intermediate 7 (prepared according to A5) was added in small portions in 4.5 hours. Content C(=O)Cl₂ was checked (aniline) in reaction mixture and excess was maintained by addition of solution C(=O)Cl₂. Dioxane was evaporated to dryness and yellow solid was treated with acetone. White solid obtained was filtered and recrystallized from methanol. Yield: 0.87 g (39.3%) of compound 41 (mp.: 192-195° C.).

EXAMPLE B18

Preparation of Compound 35

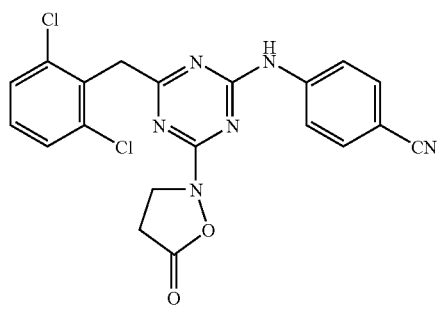

The mixture of 4-[[4-[(2,6-dichlorophenyl)methyl]-6-(hydroxyamino)-1,3,5-triazin-2-yl]amino]benzonitrile(9 mmol) and THF (50 ml) was stirred and cooled (−12° C.). ClCH₂CH₂C(=O)Cl (10.5 mmol) in THF (15 ml) was added dropwise into the previously prepared mixture for about 15 minutes. The solvent was removed by destination under reduced pressure. The part of raw product was chromatographed on silica gel (CH₂Cl₂/acetone 95:5). The obtained solid was recrystallized from mixture chloroform-heptane (25% chloroform). Yield: 0.1 g (2.5%, white solid) of compound 35 (mp.: 168-173° C.).

EXAMPLE B19

Preparation of Compound 34

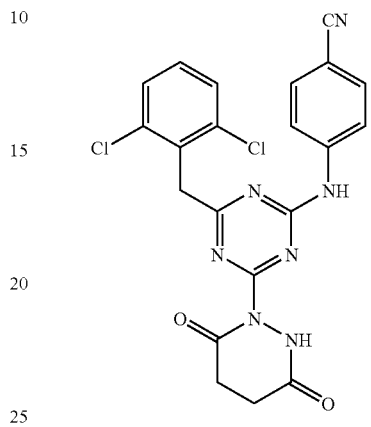

The mixture of compound 47 (prepared according to B14) (0.4 mmol) in methanol (50 ml) was refluxed and stirred for 5.5 hours. The conversion of compound 47 to compound 34 was monitored by HPLC. The reaction mixture was concentrated by destillation. The precipitated solid was collected by suction and dried. Yield: 102 mg (55%, white solid) of compound 34 (mp.: 155-157° C.).

EXAMPLE B20 a) Preparation of Compound 52

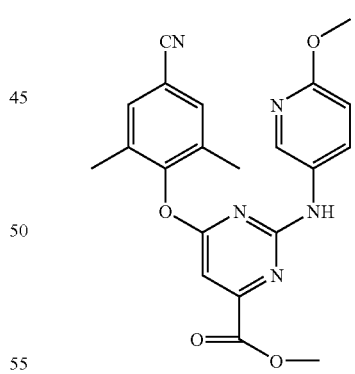

500 mg (1.57 mmol) of interm. (9), 586 mg (3 equiv.) of 5-amino-2-methoxy-pyridine and 47 mg (0.2 mol %) of NaI were dissolved in 10 ml of 1,2-dimethoxy-ethane and stirred at 60° C. for 3 days. Then, the mixture was diluted with ethyl acetate and washed succesively with 0.5 N aqueous KHSO₄ (2×) and with brine. The organic layer was dried over Na₂SO₄ and evaporated. The residue was purified by silica column chromatography using ethyl acetate/n-heptane 1/1 as the eluent to obtain 306 mg (48%) of compound 52.

b) Preparation of Compound 56

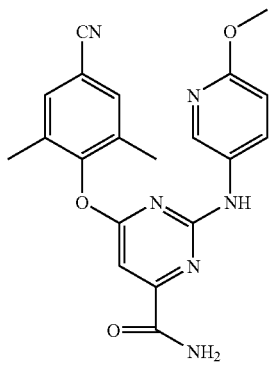

100 mg (0.247 mmol) of compound 52 was dissolved in 2.5 ml of THF and cooled to 0° C. 2.5 ml of a 7 N methanolic NH3 solution was added. The mixture was stirred overnight in a cooler at ±4° C. The reaction mixture was diluted with diisopropyl ether and evaporated. More diisopropyl ether was added and the mixture was cooled. The product was filtered off to yield 93 mg (96%) of compound 56.

c) Preparation of Compound 54

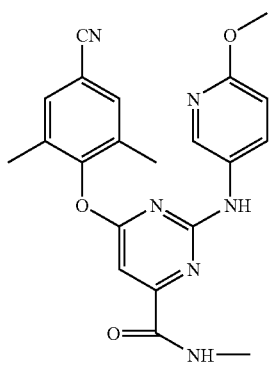

80 mg (o,197 mmol) of compound 52, 133 mg (10 equiv.) of H₂NMe.HCl and 0.5 ml (15 equiv.) of N,N-diisopropy-lethanamine were dissolved in 4 ml THF/MeOH 1/1 and stirred overnight at 20° C. After that, the solvents were evaporated and the residue was dissolved in ethyl acetate and washed succesively with 0.5 N KHSO₄ (2×) and brine, dried over Na₂SO₄ and evaporated. The residue was stirred in n-heptane/diisopropyl ether 1/1 and the product was filtered off and dried to yield 60 mg (75%) of compound 54.

d) Preparation of Compound 65

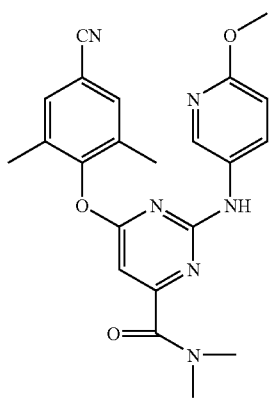

50 mg (o. 123 mmol) of compound 52 was dissolved in 3 ml of dry THF and 200 μl (1.25 equiv.) of

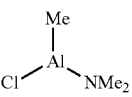

(0.76 M in hexane/toluene) was added. The mixture was stirred overnight at 20° C. 50 μl of

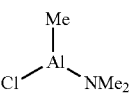

was added and stirring was continued for another night. Then, THF was evaporated and the residue was taken up in ethyl acetate and washed successively with saturated aqueous NaHCO₃ and with brine, dried over Na₂SO₄ and evaporated. The residue was stirred in n-heptane/diisopropyl ether 1/1 and the product was filtered off and dried to yield 44 mg (85%) of compound 65.

e) Preparation of Compound 95

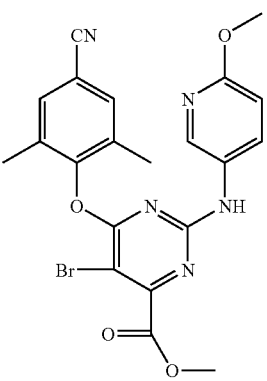

31 mg (o.o765 mmol) of compound 52 was dissolved in 0.73 ml of 0.1 N solution of Br₂ in acetic acid (0.95 equiv.). After overnight stirring at 20° C., the solvent was evaporated and the residue was stirred in ethyl acetate/saturated aqueous NaHCO₃ until gas evolution ceased. The organic layer was washed with brine, dried over Na₂SO₄ and evaporated. The residue was purified by silica preparative thin layer chromatography using ethyl acetate/n-heptane 1/4 as the eluent. The major band is scraped off the thin layer chromatography plate and extracted. The extract was evaporated and dried to yield 21 mg (58%) of compound 95.

f) Preparation of Compound 55

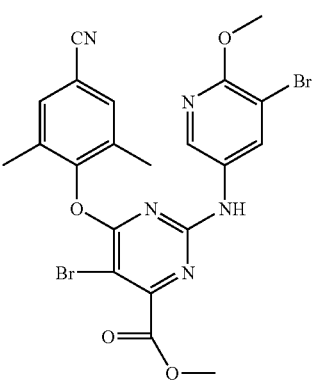

20 mg (0.0494 mmol) of compound 52 was suspended in 2 ml of H$_2$O and 23 mg (3 equiv.) of Br$_2$ were added. The mixture was stirred at 60° C. overnight. Then, the mixture was cooled to 20° C. and filtered off. The residue was purified by silica preparative thin layer chromatography using ethyl acetate/n-heptane 1/2 as the eluent. The major band is scraped off the thin layer chromatography plate and extracted. The extract was evaporated and dried to yield 10 mg (36%) of compound 55.

g) Preparation of Compound 53

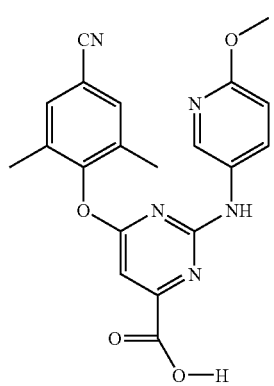

100 mg (0.247 mmol) of compound 52 was dissolved in 7.5 ml of MeOH and 1.75 ml of a 0.4 N aqueous LiOH solution was added. The mixture was stirred at 20° C. for 4 hours. Then, Amberlite ion exchange material (H$^+$-form) was added and 2 ml of MeOH. When the solution was neutral, the Amberlite was filtered off, MeOH was evaporated and the residue was stirred in diisopropyl ether, filtered off and dried to yield 80 mg (83%) of compound 53.

EXAMPLE B21 a) Preparation of Compound 50

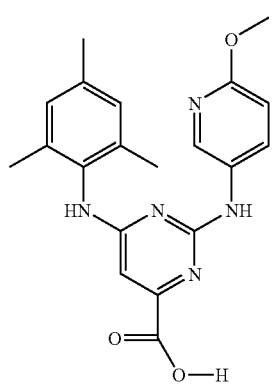

200 mg (0.654 mmol) of 2-chloro-4-N-(2,4,6-trimethylanilinyl)-pyrimidine-6-carboxy methyl ester, prepared according to A2a), and 244 mg (3 equiv.) of 5-amino-2-methoxy-pyridine were dissolved in 2 ml of n-BuOH and 2 ml of H$_2$O and 3 drops of 37% aqueous HCl were added. The reaction mixture was stirred at 85° C. for 2 days. Then, the solvents were evaporated, the residue was stirred in 15 ml H$_2$O/15 ml CH$_2$Cl$_2$ and the solid material was filtered off. The residue was washed with H$_2$O, with diethyl ether and with CH$_2$Cl$_2$ to yield 127 mg (51%) of compound 50.

b) Preparation of Compound 51

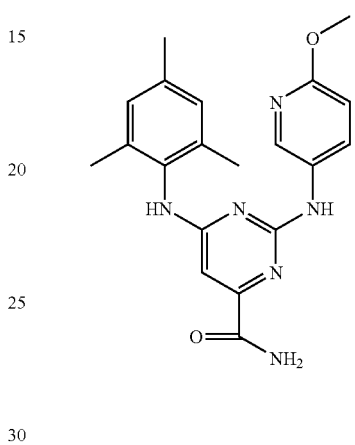

60 mg (0.158 mmol) of compound 50 was suspended in dry DMF and 58 μl (5 equiv.) of SOCl$_2$ were added. The reaction mixture was stirred at 60° C. overnight and the excess SOCl$_2$ was removed by evaporation. The DMF solution was cooled to 0° C. and 2 ml of 37° C. NH$_4$OH was added. The reaction mixture was stirred for 1 hour at 0° C. Then, the solvents were evaporated and the residue was stirred in MeOH for 2 hours, filtered off and washed with diisopropyl ether to yield 30 mg (50%) of compound 51.

EXAMPLE B22 a) Preparation of Compound 96

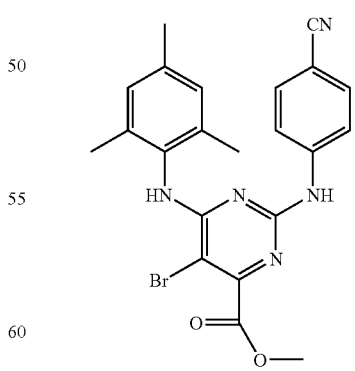

60 mg (0.155 mmol) of compound 62, prepared according to B16a), was dissolved in 1.7 ml of 0.1 N solution of Br$_2$ in acetic acid (1.1 equiv.). After 1 hour, the solvent was evaporated and the residue was stirred in ethyl acetate/ saturated aqueous NaHCO₃ until gas evolution ceased. The organic layer was washed with brine, dried over Na₂SO₄ and evaporated. The residue was stripped with n-heptane and stirred in n-heptane/diisopropyl ether 1/1 and the product was filtered off and dried to yield 72 mg (100%) of compound 96.

b) Preparation of Compound 98

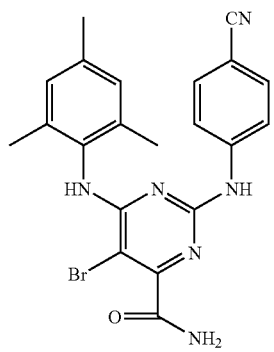

105 mg (0.225 mmol) of compound 96 was dissolved in 2 ml of MeOH and 2 ml of a 7 N NH₃ solution in MeOH was added. The reaction was stirred at 20° C. over the weekend. The solvent was evaporated and the residue stripped with CH₂Cl₂, stirred in diisopropyl ether and filtered off to yield 64 mg (63%) of compound 98.

EXAMPLE B23

Preparation of Compound 93

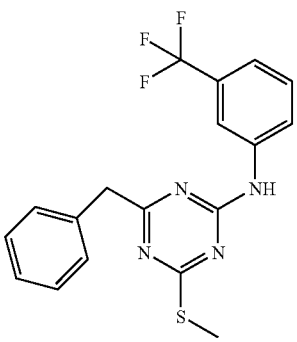

A mixture of interm. 12 (0.00028 mol) and benzeneacetyl chloride (0.00028 mol) in acetonitrile (10 ml) was stirred while cooling on an ice-bath. Sodium acetate (0.00084 mol) was added and the mixture was stirred for 30 minutes on an ice-bath, then stirred overnight at room temperature. Methyl carbamimidothioate (0.00056 mol) was added. Na₂CO₃ (0.0011 mol) was added and the mixture was stirred overnight at 80° C., then cooled to room temperature. CH₂Cl₂ (10 ml) was added. Water (2 ml) was added and the mixture was stirred for 30 minutes. The mixture was filtered through Extrelut and the filtrate was evaporated. The residue was purified by HPLC over silica gel (eluent: CH₂Cl₂/CH₃OH 90/10). The product fractions were collected and the solvent was evaporated to yield compound 93.

The following Tables list compounds of formula (I) as prepared according to one of the above examples (Ex. No.).

TABLE 1

| Co. No. | Ex. No. | Z | R² | L | Q | Physical data/mp. |
|---|---|---|---|---|---|---|
| 17 | B1a-2 | CH | Br | (2,4,6-trimethylphenyl)amino | CF₃ | 198–201° C. |
| 18 | B5a | N | CN | (2,4,6-trimethylphenyl)amino | CN | 309–313° C. |
| 19 | B5d | N | CN | (2,4,6-trimethylphenyl)amino | C(=O)—NH₂ | |
| 20 | B7 | N | CN | (2,4,6-trimethylphenyl)aniino | SCH₃ | 108–109° C. |
| 21 | B5e | CH | CN | (2,4,6-trimethylphenyl)amino | CF₃ | 179–182° C. |
| 22 | B21a | CH | CN | (2,4,6-trimethylphenyl)amino | COOH | |
| 23 | B5a | N | CN | (2,4,6-trimethylphenyl)oxy | CN | |
| 24 | B1a-4 | CH | Br | (2,4,6-trimethylphenyl)oxy | CF₃ | 129° C. |
| 25 | B5e | CH | CN | (2,4,6-trimethylphenyl)oxy | CF₃ | 202° C. |
| 26 | B5d | N | CN | (2,4,6-trimethylphenyl)oxy | C(=O)—NH₂ | 280–286° C. |
| 27 | B2 | CH | CN | (2,6-dibromo-4-cyano phenyl)oxy | CH₂—O—CH₃ | 218–220° C. |
| 14 | B12 | CH | CN | (2,6-dibromo-4-cyano phenyl)oxy | CH₂—OH | 277–278° C. |
| 15 | B12 | C—F | CN | (2,6-dibromo-4-cyano phenyl)oxy | CH₂—OH | 240–241° C. |
| 16 | B12 | C—Br | CN | (2,6-dibromo-4-cyano phenyl)oxy | CH₂—OH | 250–251° C. |
| 28 | B5 | N | CN | (4-cyano-2,6-dimethyl phenyl)oxy | CN | 288–291.5° C. |
| 29 | B5e | CH | CN | (2,6-dimethylphenyl)amino | CF₃ | |
| 30 | B5e | CH | CN | (2,6-dimethylphenyl)oxy | CF₃ | |

TABLE 1-continued

| Co. No. | Ex. No. | Z | R² | L | Q | Physical data/mp. |
|---|---|---|---|---|---|---|
| 31 | B1a-4 | CH | Br | (2,6-dimethylphenyl)oxy | CF₃ | |
| 3 | B3 | CH | CN | (2-chloro-4-fluoro-5-methyl-phenyl)amino | CH₂—O—CH₃ | 213–214° C. |
| 32 | B1c | CH | CN | (4-bromo-2,6-dimethyl-phenyl)amino | CF₃ | 209–211° C. |
| 33 | B5e | CH | CN | (4-cyano-2,6-dimethyl-phenyl)amino | CF₃ | 249–251° C. |
| 2 | B2 | CH | CN | (4-cyano-2,6-dimethyl phenyl)oxy | CH₂—O—CH₃ | 203–204° C. |
| 12 | B11a | C—Br | CN | (4-cyano-2,6-dimethyl phenyl)oxy | CH₂—O—CH₃ | 198–199° C. |
| 13 | B11b | C—Br | CN | (4-cyano-2,6-dimethyl phenyl)oxy | CH₂—OH | 279–281° C. |
| 57 | B2b | N | CN | (2,4,6-trimethylphenyl)oxy | Cl | 234–236° C. |
| 60 | B2c | N | CN | (4-cyano-2,6-dimethyl phenyl)oxy | Cl | 260–265° C. |
| 61 | B16b | CH | CN | (2,4,6-trimethylphenyl)amino | C(=O)—NH₂ | |
| 62 | B16a | CH | CN | (2,4,6-trimethylphenyl)amino | C(=O)—OCH₃ | |
| 63 | B16c | CH | CN | (2,4,6-trimethylphenyl)amino | C(=O)—NHCH₃ | |
| 66 | B16d | CH | CN | (2,4,6-trimethylphenyl)amino | C(=O)—N(CH₃)₂ | |
| 67 | B1a-2 | N | CN | (2,4,6-trimethylphenyl)amino | Cl | 275–276° C. |
| 79 | B1a-2 | N | CN | (2,6-ethylphenyl)amino | Cl | |
| 80 | B1a-2 | N | CN | (2-oxomethyl-5-methyl-phenyl)amino | Cl | |
| 81 | B1a-2 | N | CN | (4-bromo-2,6-dimethyl-phenyl)amino | Cl | |
| 82 | B1a-2 | N | CN | (5-bromo-2,4,6-trimethyl-phenyl)amino | Cl | |
| 83 | B1a-2 | N | CN | (2-ethyl-6-methylphenyl)amino | Cl | |
| 84 | B1a-2 | N | CN | (2-broom-4,6-difluoro-phenyl)amino | Cl | |
| 85 | B1a-2 | N | CN | (2,4,6-trichlorophenyl)amino | Cl | 295–296° C. |
| 70 | B1a-3 | N | CN | (2,6-dichlorophenyl)amino | Cl | 268–269° C. |
| 86 | B1a-2 | N | CN | (2,6-dichloro-4-trifluoromethyl-phenyl)amino | Cl | 247–248° C. |
| 87 | B1a-2 | N | CN | (2,4-dichloro-6-trifluoromethyl-phenyl)amino | Cl | 275–276° C. |
| 88 | B1a-2 | N | CN | (2,4,6-tribromophenyl)amino | Cl | 292–294° C. |
| 89 | B1a-2 | N | CN | (2,6-dibromo-4-methyl-phenyl)amino | Cl | 283–284° C. |
| 90 | B1a-2 | N | CN | (2,6-dibromo-4-ipropyl-phenyl)amino | Cl | 263–264° C. |
| 91 | B1a-2 | N | OCH₃ | (4-methoxyphenyl)amino | Cl | |
| 96 | B22a | C—Br | CN | (2,4,6-trimethylphenyl)amino | COOCH₃ | |
| 71 | B1c | CH | CN | (4-cyano-2,6-dimethyl-phenyl)amino | COOCH₃ | 258–259° C. |
| 97 | B1c | CH | CN | (4-cyano-2,6-dimethyl-phenyl)amino | COOH | 258–259° C. |
| 98 | B22b | C—Br | CN | (2,4,6-trimethylphenyl)amino | CONH₂ | |
| 73 | B11c | C—Br | CN | (4-cyano-2,6-dimethyl-phenyl)amino | CH₂Cl | 238–240° C. |
| 74 | B11d | C—Br | CN | (4-cyano-2,6-dimethyl-phenyl)oxy | CH₂NHCH₃ | 223–224° C. |
| 100 | B11d | C—Br | CN | (4-cyano-2,6-dimethyl-phenyl)oxy | CH₂N(CH₃)₂ | 189–191° C. |
| 101 | B11d | C—Br | CN | (4-cyano-2,6-dimethyl-phenyl)oxy | CH₂NHCH₂CH | 202–203° C. |
| 103 | B2a | N | CN | (2,6-dichlorophenyl)oxy | Cl | |
| 104 | B1b | N | CN | (2-chloro-4-fluorophenyl)methyl | Cl | 201–202° C. |
| 105 | B1b | N | CN | (2,4-dichlorophenyl)methyl | Cl | 191–192° C. |
| 106 | B1a | N | CN | (2,6-dichlorophenyl)amino | Cl | |
| 107 | B1a-1 | N | CN | (2,6-dimethylphenyl)amino | Cl | |
| 69 | B1a-2 | N | CN | (2-chloro-6-methylphenyl)amino | Cl | |
| 108 | B1a-2 | N | CN | (2-ipropyl-6-methyl-phenyl)amino | Cl | |

TABLE 1-continued
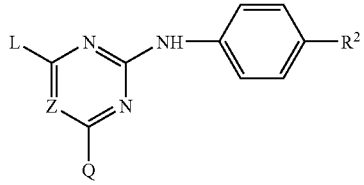
| Co. No. | Ex. No. | Z | R² | L | Q | Physical data/mp. |
|---|---|---|---|---|---|---|
| 109 | B1a-2 | N | CN | (2,4-dichloro-6-methyl-phenyl)amino | Cl | |
| 110 | B1a-2 | N | CN | (3-chloro-2,6-dimethyl-phenyl)amino | Cl | 142–143° C. |
| 72 | B2b | N | CN | (2,4,6-trichlorophenyl)oxy | Cl | 238–239° C. |
TABLE 2
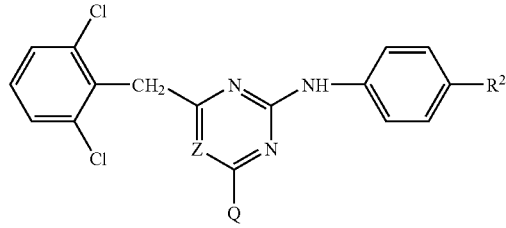
| Co. No. | Ex. No. | Z | R² | Q | Physical data mp. |
|---|---|---|---|---|---|
| 34 | B19 | N | CN | 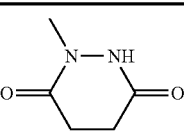 | 155–157° C. |
| 35 | B18 | N | CN | 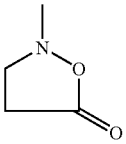 | 168–173° C. |
| 36 | B14 | N | CN | 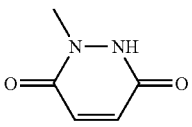 | |
| 37 | B13 | N | CN | 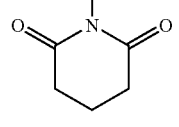 | 278–282° C. |
| 38 | B5d | N | CN | C(=O)—NH₂ | 262–263° C. |
| 39 | B1d | CH | CN | 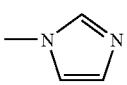 | 275–285° C. |
| 5 | B5 | N | CN | CN | 221–230° C. |
| 40 | B5b | N | C(=O)—NH₂ | C(=O)—NH₂ | 287–295° C. |

TABLE 2-continued
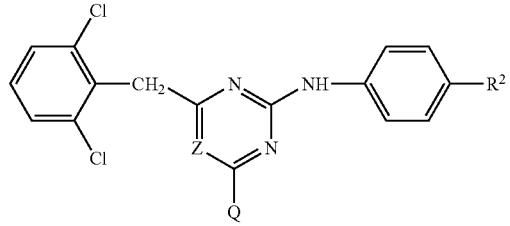
| Co. No. | Ex. No. | Z | R² | Q | Physical data mp. |
|---|---|---|---|---|---|
| 41 | B17 | N | C(=O)—NH₂ | 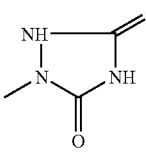 | 192–195° C. |
| 42 | B5c | N | 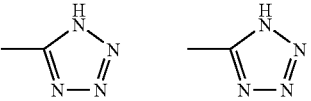 | 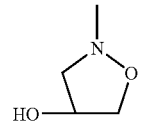 | 249–252° C. |
| 11 | B10a | N | CN | 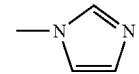 | trifluoroacetate (1:1); 175° C. |
| 1 | B1 | N | CN | Cl | 243–244° C. |
| 7 | B7a | N | CN | S—CH₃ | 184–185° C. |
| 8 | B7b | N | CN | S(=O)—CH₃ | 219–221° C. |
| 9 | B8 | N | CN | OCH₃ | 198–199° C. |
| 6 | B6 | N | CN | SH | 254–255° C. |
| 10 | B9 | N | CN | OH | >300° C. |
| 44 | B10b | N | CN | 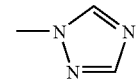 | |
| 45 | B10b | N | CN | 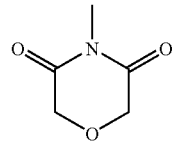 | 267–270° C. |
| 4 | B4 | N | CN | 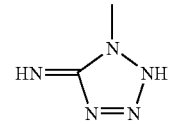 | 268–269° C. |
| 46 | B10b | N | CN | 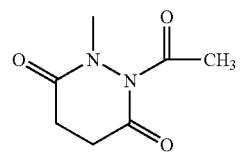 | 302–304° C. |
| 47 | B14 | N | CN |  | 213–215° C. |

TABLE 2-continued

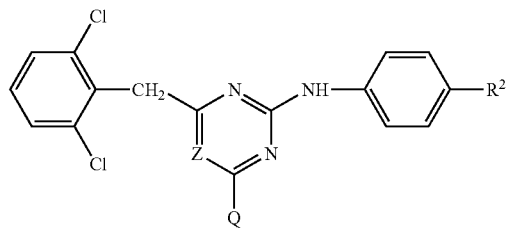

| Co. No. | Ex. No. | Z | R² | Q | Physical data mp. |
|---|---|---|---|---|---|
| 48 | B13 | N | CN | (N-methylsuccinimide) | 223–226° C. |
| 49 | B15 | N | CN | F | 196° C. |
| 58 | B8 | N | CN | OC₂H₅ | 302–304° C. |
| 59 | B10a | N | CN | (tetrazole) | 196–197° C. |
| 43 | B1e | N | CN | NH—O—CH₂—C≡CH | trifluoroacetate (1:1); 225–227° C. |
| 68 | B1e | N | CN | —NH—O—CH₂—C(=O)—morpholine | trifluoroacetate (1:1); >80° C. |

TABLE 3

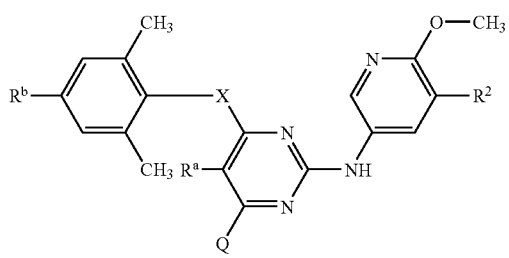

| Co. No. | Ex. No. | X | Rᵃ | Rᵇ | R² | Q | Physical data |
|---|---|---|---|---|---|---|---|
| 50 | B21a | NH | H | CH₃ | H | COOH | |
| 51 | B21b | NH | H | CH₃ | H | C(=O)—NH₂ | |
| 52 | B20a | O | H | CN | H | COOCH₃ | |
| 53 | B20g | O | H | CN | H | COOH | |
| 54 | B20c | O | H | CN | H | C(=O)—NH—CH₃ | |
| 55 | B20f | O | Br | CN | Br | COOCH₃ | |
| 56 | B20b | O | H | CN | H | C(=O)—NH₂ | |
| 65 | B20d | O | H | CN | H | C(=O)—N(CH₃)₂ | |
| 95 | B20e | O | Br | CN | H | COOCH₃ | |

TABLE 4

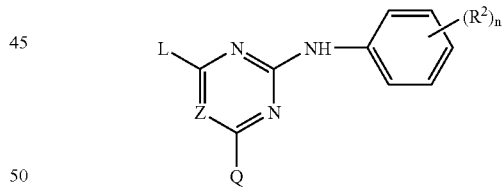

| Co. No. | Ex. No. | Z | R² | L | Q | Physical data/mp. |
|---|---|---|---|---|---|---|
| 92 | B23 | N | 2,3-dichloro | benzyl | SCH₃ | |
| 93 | B23 | N | 3-trifluoromethyl | benzyl | SCH₃ | |
| 94 | B23 | N | 3-trifluoromethyl | benzyl | OCH₃ | |

C. PHARMACOLOGICAL EXAMPLE

The pharmacological activity of the present compounds was examined using the following test.

A rapid, sensitive and automated assay procedure was used for the in vitro evaluation of anti-HIV agents. An HIV-1 transformed T4-cell line, MT-4, which was previously shown (Koyanagi et al., *Int. J. Cancer,* 36, 445-451, 1985) to be highly susceptible to and permissive for HIV infection, served as the target cell line. Inhibition of the HIV-induced cytopathic effect was used as the end point. The viability of both HIV- and mock-infected cells was assessed spectrophotometrically via the in situ reduction of 3-(4,5-dimethylthiazol-2-yl)-2,5-diphenyltetrazolium bromide (MTT). The 50% cytotoxic concentration ($CC_{50}$ in μM) was defined as the concentration of compound that reduced the absorbance of the mock-infected control sample by 50%. The percent protection achieved by the compound in HIV-infected cells was calculated by the following formula:

$$\frac{(OD_T)_{HIV} - (OD_C)_{HIV}}{(OD_C)_{MOCK} - (OD_C)_{HIV}} \text{ expressed in \%,}$$

whereby $(OD_T)_{HIV}$ is the optical density measured with a given concentration of the test compound in HIV-infected cells; $(OD_C)_{HIV}$ is the optical density measured for the control untreated HIV-infected cells; $(OD_C)_{MOCK}$ is the optical density measured for the control untreated mock-infected cells; all optical density values were determined at 540 nm. The dose achieving 50% protection according to the above formula was defined as the 50% inhibitory concentration ($IC_{50}$ in μM). The ratio of $CC_{50}$ to $IC_{50}$ was defined as the selectivity index (SI). Table 5 lists the $IC_{50}$, $CC_{50}$ and SI values for the compounds of formula (I).

TABLE 5

| Co. No. | $IC_{50}$ (μM) | $CC_{50}$ (μM) | SI |
|---|---|---|---|
| 7 | 0.02 | 39.81 | 1990 |
| 9 | 0.01 | >100 | >10000 |
| 67 | 0.001995 | >10 | >5012 |
| 4 | 0.00158 | 39.81 | 25197 |
| 48 | 0.0079 | >200 | >12658 |
| 25 | 0.079 | >100 | >1266 |
| 20 | 0.002 | 3.981 | 1990 |
| 58 | 0.0251 | 50.12 | 1997 |
| 35 | 0.0631 | 50.12 | 794 |
| 33 | 0.00316 | 5.012 | 1586 |
| 38 | 0.00251 | >100 | >39841 |
| 5 | 0.01995 | 10 | 501 |
| 43 | 0.01585 | 63.096 | 3981 |
| 11 | 0.00251 | 63.096 | 25138 |
| 68 | 0.01585 | 19.95 | 1259 |
| 19 | 0.001259 | 3.981 | 3162 |
| 2 | 0.001585 | 50.12 | 31621 |
| 12 | 0.0040 | >100 | >25000 |
| 13 | 0.0040 | >100 | >25000 |
| 26 | 0.001 | 1.995 | 1995 |
| 3 | 0.0501 | >100 | >1996 |
| 27 | 0.01 | >10 | >1000 |
| 14 | 0.0040 | >10 | 2500 |
| 56 | 0.0631 | >100 | 1585 |
| 16 | 0.0251 | >100 | >39841 |
| 65 | 0.07943 | 79.43 | 1000 |
| 62 | 0.0063 | 7.943 | 1261 |
| 61 | 0.00251 | 50.12 | 19968 |
| 63 | 0.00501 | 39.81 | 7946 |
| 66 | 0.001585 | 31.62 | 19950 |
| 71 | 0.0251 | >100 | >3984 |
| 109 | 0.00398 | 12.59 | 3163 |
| 85 | 0.02 | 50.12 | 2506 |
| 89 | 0.00501 | 10 | 1996 |
| 98 | 0.00316 | 50.12 | 15861 |

What is claimed is:
1. A compound having the formula

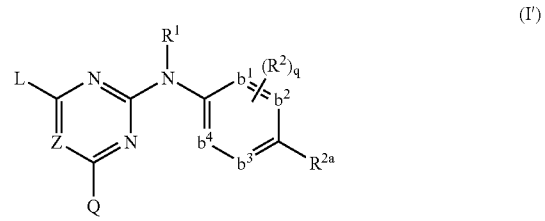

a N-oxide, a pharmaceutically acceptable addition salt, a quaternary amine and a stereochemically isomeric form thereof, wherein
-$b^1$=$b^2$-C($R^{2a}$)=$b^3$-$b^4$=represents a bivalent radical of formula —CH=CH—C($R^{2a}$)=CH—CH=    (b-1);

q is 0, 1, 2; or where possible q is 3 or 4;
$R^1$ is hydrogen; aryl; formyl; $C_{1-6}$alkylcarbonyl; $C_{1-6}$alkyl; $C_{1-6}$alkyloxycarbonyl; $C_{1-6}$alkyl substituted with formyl, $C_{1-6}$alkylcarbonyl, $C_{1-6}$alkyloxycarbonyl, $C_{1-6}$alkylcarbonyloxy; $C_{1-6}$alkyloxy$C_{1-6}$alkylcarbonyl substituted with $C_{1-6}$alkyloxycarbonyl;
L is $C_{1-10}$alkyl, $C_{2-10}$alkenyl, $C_{2-10}$alkynyl, $C_{3-7}$cycloalkyl, whereby each of said groups may be substituted with one or two substituents independently selected from $C_{3-7}$cycloalkyl, indolyl or isoindolyl, each optionally substituted with one, two, three or four substituents each independently selected from halo, $C_{1-6}$alkyl, hydroxy, $C_{1-6}$alkyloxy, cyano, aminocarbonyl, nitro, amino, polyhalomethyl, polyhalomethyloxy and $C_{1-6}$alkylcarbonyl, phenyl, pyridyl, pyrimidinyl, pyrazinyl or pyridazinyl, wherein each of said aromatic rings may optionally be substituted with one, two, three, four or five substituents each independently selected from the substituents defined in $R^2$; or
L is —$X^1$—$R^3$ or —$X^2$-Alk-$R^4$ wherein
Alk is $C_{1-4}$alkanediyl;
$R^3$ or $R^4$ each independently are phenyl, pyridyl, pyrimidinyl, pyrazinyl or pyridazinyl, wherein each of said aromatic rings may optionally be substituted with one, two, three, four or five substituents each independently selected from the substituents defined in $R^2$; and
$X^1$ or $X^2$ each independently are —$NR^7$—, —NH—NH—, —N=N—, —O—, —C(=O)—, —CHOH—, —S—, —S(=O)$_p$—;
Q represents cyano, hydroxy, mercapto, carboxyl, formyl, cyano$C_{1-6}$alkyl, hydroxy$C_{1-6}$alkyl, mercapto$C_{1-6}$alkyl, amino$C_{1-6}$alkyl, mono- or di($C_{1-4}$alkyl)-amino$C_{1-6}$alkyl, aminocarbonyl, mono- or di($C_{1-4}$alkyl)aminocarbonyl, $C_{1-6}$alkyloxy, $C_{1-6}$alkylthio, $C_{1-6}$alkylS(=O)$_p$, $C_{1-6}$alkylcarbonyl, $C_{1-6}$alkylcarbonyloxy, $C_{1-6}$alkyloxycarbonyl, $C_{1-6}$alkylcarbonyloxy$C_{1-6}$alkyl, $C_{2-6}$alkenyl, $C_{2-6}$alkenyloxyamino, $R^5$—C(=O)—$C_{1-6}$alkyloxyamino, $C_{2-6}$alkynyl, polyhalo$C_{1-6}$alkyl, hydroxypolyhalo$C_{1-6}$alkyl, Het or $C_{1-6}$alkyloxy$C_{1-6}$alkyl wherein each hydrogen atom may optionally be substituted with $C_{1-6}$alkyloxy;

Z is C—Y wherein

Y represents hydrogen, hydroxy, halo, $C_{1-6}$alkyl, $C_{3-7}$cycloalkyl, $C_{2-6}$alkenyl optionally substituted with one or more halogen atoms, $C_{2-6}$alkynyl optionally substituted with one or more halogen atoms, $C_{1-6}$alkyl substituted with cyano or —C(=O)$R^8$, $C_{1-6}$alkyloxy, $C_{1-6}$alkyloxycarbonyl, carboxyl, cyano, nitro, amino, mono- or di($C_{1-6}$alkyl)amino, polyhalomethyl, polyhalomethyloxy, polyhalomethylthio, —S(=O)$_p$$R^8$, —NH—S(=O)$_p$$R^8$, —C(=O)$R^8$, —NHC(=O)H, —C(=O)NHNH$_2$, —NHC(=O)$R^8$, —C(=NH)$R^8$ or aryl;

$R^5$ is hydrogen or a radical of formula

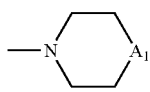

(d)

with $A_1$ in (d) being CH$_2$ or O;

$R^6$ is methyl, amino, mono- or dimethylamino or polyhalomethyl;

$R^7$ is hydrogen; aryl; formyl; $C_{1-6}$alkylcarbonyl; $C_{1-6}$alkyl; $C_{1-6}$alkyloxycarbonyl; $C_{1-6}$alkyl substituted with formyl, $C_{1-6}$alkylcarbonyl, $C_{1-6}$alkyloxycarbonyl, $C_{1-6}$alkylcarbonyloxy; $C_{1-6}$alkyloxy$C_{1-6}$alkylcarbonyl substituted with $C_{1-6}$alkyloxycarbonyl;

$R^8$ is methyl, amino, mono- or dimethylamino or polyhalomethyl;

p is 1 or 2;

aryl is phenyl or phenyl substituted with one, two, three, four or five substituents each independently selected from halo, $C_{1-6}$alkyl, $C_{3-7}$cycloalkyl, $C_{1-6}$alkyloxy, cyano, nitro, polyhalo$C_{1-6}$alkyl, polyhalo$C_{1-6}$alkyloxy, aminocarbonyl, tetrazolyl;

Het is imidazolyl, thiazolyl, oxazolyl, pyrazolyl, isothiazolyl, isoxazolyl, triazolyl, tetrazolyl optionally substituted with imino, a radical of formula (c) as described hereinabove, imidazolidinyl, pyrazolidinyl, thiazolidinyl, isothiazolidinyl, oxazolidinyl, isoxazolidinyl optionally substituted with hydroxy, isoxazolidinone, or a radical of formula

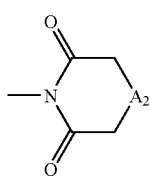

(e-1)

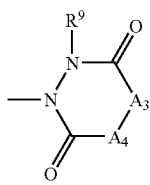

(e-2)

with $A_2$ in (e-1) being O, CH$_2$ or a direct bond;
$A_3$ being CH$_2$ or NH;
$A_4$ being CH$_2$ or a direct bond; or
$A_3$-$A_4$ representing CH=CH;

$R^9$ being hydrogen or $C_{1-4}$alkylcarbonyl;

provided that when Q is polyhalo$C_{1-6}$alkyl then Y is hydrogen or $C_{1-6}$alkyl;

$R^{2a}$ is cyano, aminocarbonyl, mono- or di(methyl)aminocarbonyl, $C_{1-6}$alkyl substituted with cyano, aminocarbonyl or mono- or di(methyl)aminocarbonyl, $C_{2-6}$alkenyl substituted with cyano, or $C_{2-6}$alkynyl substituted with cyano;

each $R^2$ independently is hydroxy, halo, $C_{1-6}$alkyl optionally substituted with cyano or —C(=O)$R^6$, $C_{3-7}$cycloalkyl, $C_{2-6}$alkenyl optionally substituted with one or more halogen atoms or cyano, $C_{2-6}$alkynyl optionally substituted with one or more halogen atoms or cyano, $C_{1-6}$alkyloxy, $C_{1-6}$alkyloxycarbonyl, carboxyl, cyano, nitro, amino, mono- or di($C_{1-6}$alkyl)amino, polyhalomethyl, polyhalomethyloxy, polyhalomethylthio, —S(=O)$_p$$R^6$, —NH—S(=O)$_p$$R^6$, —C(=O)$R^6$, —NHC(=O)H, —C(=O)NHNH$_2$, —NHC(=O)$R^6$, —C(=NH)$R^6$ or a radical of formula

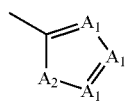

(c)

wherein each $A_1$ in (c) independently is N, CH or CR$^6$;
$A_2$ in (c) is NH, O, S or NR$^6$;
p is 1 or 2.

2. A compound as claimed in claim 1, wherein Q is cyano, hydroxy, mercapto, carboxyl, hydroxy$C_{1-6}$alkyl, mono- or di($C_{1-4}$alkyl)amino$C_{1-6}$alkyl, aminocarbonyl, $C_{1-6}$alkyloxy$C_{1-6}$alkyl wherein each hydrogen atom may optionally be substituted with $C_{1-6}$alkyloxy, $C_{1-6}$alkyloxy, $C_{1-6}$alkylthio, $C_{1-6}$alkylS(=O), $C_{1-6}$alkyloxycarbonyl, polyhalo$C_{1-6}$alkyl, $C_{2-6}$alkenyloxyamino, $R^5$—C(=O)—$C_{1-6}$alkyloxyamino, a radical of formula (c) or (e-1) or (e-2), imidazolyl, triazolyl, tetrazolyl optionally substituted with imino, isoxazolidinyl optionally substituted with hydroxy, isoxazolidinone.

3. A compound as claimed in claim 1, wherein L is —X$^1$—$R^3$ wherein $R^3$ is 2,4,6-trisubstituted phenyl.

4. A compound as claimed in claim 2, wherein L is —X$^1$—$R^3$ wherein $R^3$ is 2,4,6-trisubstituted phenyl.

5. A compound as claimed in claim 1, wherein the moiety in the 2 position of the pyrimidine ring is a 4-cyano-anilino group, L is —X$^1$—$R^3$ wherein $R^3$ is a 2,4,6-trisubstituted phenyl, Z is C—Y with Y being halo or hydrogen and Q is hydroxy$C_{1-6}$alkyl, $C_{1-6}$alkyloxy$C_{1-6}$alkyl, polyhalo$C_{1-6}$alkyl, aminocarbonyl, mono- or di($C_{1-4}$alkyl)aminocarbonyl, cyano or Het.

6. A compound as claimed in claim 2, wherein the moiety in the 2 position of the pyrimidine ring is a 4-cyano-anilino group, L is —X$^1$—$R^3$ wherein $R^3$ is a 2,4,6-trisubstituted phenyl, Z is C—Y with Y being halo or hydrogen and Q is hydroxy$C_{1-6}$alkyl, $C_{1-6}$alkyloxy$C_{1-6}$alkyl, polyhalo$C_{1-6}$alkyl, aminocarbonyl, mono- or di($C_{1-4}$alkyl)aminocarbonyl, cyano or Het.

7. A compound as claimed in claim 3, wherein the moiety in the 2 position of the pyrimidine ring is a 4-cyano-anilino group, L is —X$^1$—$R^3$ wherein $R^3$ is a 2,4,6-trisubstituted phenyl, Z is C—Y with Y being halo or hydrogen and Q is hydroxy$C_{1-6}$alkyl, $C_{1-6}$alkyloxy$C_{1-6}$alkyl, polyhalo$C_{1-6}$alkyl, aminocarbonyl, mono- or di($C_{1-4}$alkyl)aminocarbonyl, cyano or Het.

8. A compound as claimed in claim 4, wherein the moiety in the 2 position of the pyrimidine ring is a 4-cyano-anilino group, L is —$X^1$—$R^3$ wherein $R^3$ is a 2,4,6-trisubstituted phenyl, Z is C—Y with Y being halo or hydrogen and Q is hydroxy$C_{1-6}$alkyl, $C_{1-6}$alkyloxy$C_{1-6}$alkyl, polyhalo$C_{1-6}$alkyl, aminocarbonyl, mono- or di($C_{1-4}$alkyl)aminocarbonyl, cyano or Het.

9. A compound according to claim 1 wherein Q is hydroxy$C_{1-6}$alkyl, mono- or di($C_{1-4}$alkyl)amino$C_{1-6}$alkyl, $C_{1-6}$alkyloxy$C_{1-6}$alkyl wherein each hydrogen atom may optionally be substituted with $C_{1-6}$alkyloxy, carboxyl, $C_{1-6}$alkyloxycarbonyl, polyhalo$C_{1-6}$alkyl, aminocarbonyl, or imidazolyl.

10. A compound according to claim 1 wherein Q is hydroxy$C_{1-6}$alkyl, mono- or di($C_{1-4}$alkyl)amino$C_{1-6}$alkyl, $C_{1-6}$alkyloxy$C_{1-6}$alkyl wherein each hydrogen atom may optionally be substituted with $C_{1-6}$alkyloxy, carboxyl, $C_{1-6}$alkyloxycarbonyl, aminocarbonyl, or imidazolyl.

11. A compound as claimed in claim 1, wherein the compound is one of:
   4-[[[5-bromo-4-(4-cyano-2,6-dimethylphenoxy)-6-hydroxymethyl]-2-pyrimidinyl]amino]benzonitrile;
   4-[[[6-trifluoromethyl-2-(4-cyanophenylamino)]-4-pyrimidinyl]amino]-3,5-dimethylbenzonitrile;
   4-[[[5-bromo-4-(4-cyano-2,6-dimethylphenoxy)-6-methoxymethyl]-2-pyrimidinyl]amino]benzonitrile;
   4-[[[5-bromo-4-(4-cyano-2,6-dibromophenoxy)-6-hydroxymethyl]2-pyrimidinyl]amino]benzonitrile;
   2-[(4-cyanophenyl)amino]-6-[(2,4,6-trimethylphenyl)amino]-4-pyrimidine carboxamide;
   5-bromo-2-[(4-cyanophenyl)amino]-6-[(2,4,6-trimethylphenyl)amino]-4-pyrimidine carboxamide; a N-oxide, a pharmaceutically acceptable addition salt, a quaternary amine and a stereochemically isomeric form thereof.

12. A process for preparing a compound as claimed in claim 1, characterized by
   a) reacting an intermediate of formula (II) with an amino derivative of formula (III) optionally under solvent-free conditions or in a reaction-inert solvent under a reaction-inert atmosphere

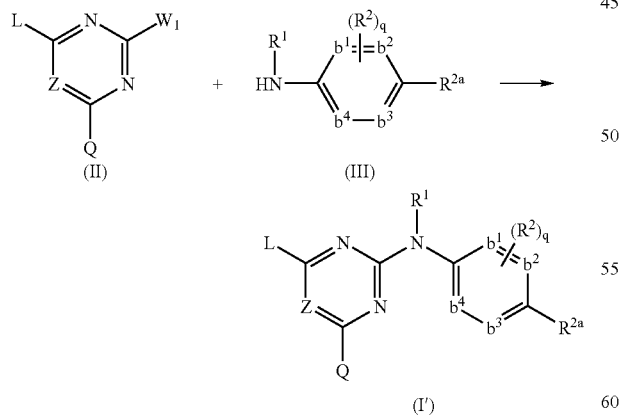

with $W_1$ being a suitable leaving group, and L, Q, Z, $R^1$, $R^2$, q and -$b^1$=$b^2$-C($R^{2a}$)=$b^3$-$b^4$=as defined in claim 1;
   b) by reacting an intermediate of formula (III) with an intermediate of formula (IV) and an intermediate of formula (V) in the presence of a suitable solvent

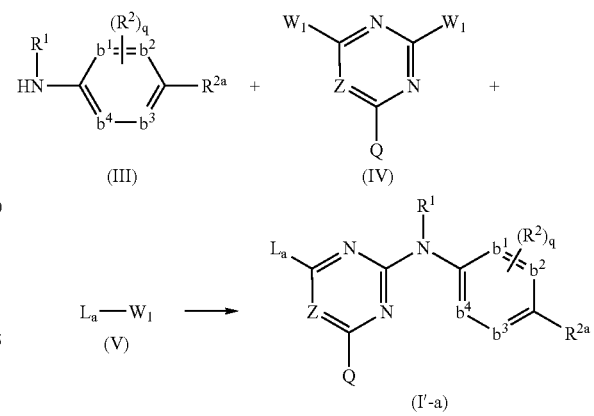

with $W_1$ being a suitable leaving group, Q, Z, $R^1$, $R^2$, q and -$b^1$=$b^2$-C($R^{2a}$)=$b^3$-$b^4$=as defined in claim 1, and $L_a$ being $C_{1-10}$alkyl, $C_{2-10}$alkenyl, $C_{2-10}$alkynyl, $C_{3-7}$cycloalkyl, each of said groups being substituted with one or two substituents independently selected from $C_{3-7}$cycloalkyl; indolyl or isoindolyl, each optionally substituted with one, two, three or four substituents each independently selected from halo, $C_{1-6}$alkyl, hydroxy, $C_{1-6}$alkyloxy, cyano, aminocarbonyl, nitro, amino, polyhalomethyl, polyhalomethyloxy and $C_{1-6}$alkylcarbonyl; phenyl, pyridinyl, pyrimidinyl, pyrazinyl or pyridazinyl, wherein each of said aromatic rings may optionally be substituted with one, two, three, four or five substituents each independently selected from the substituents defined in $R^2$;
   c) reacting an intermediate of formula (VI) with an intermediate of formula (VII) under solvent-free conditions or in an appropriate solvent under a reaction-inert atmosphere

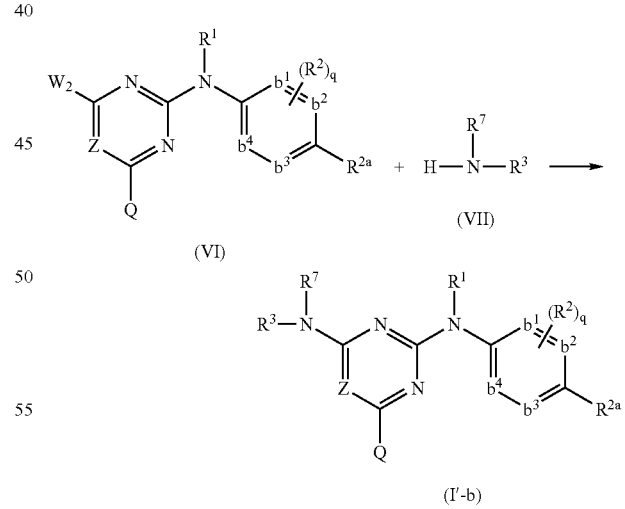

with $W_2$ being a suitable leaving group, and Q, Z, $R^1$, $R^2$, $R^3$, $R^7$, q and -$b^1$=$b^2$-C($R^{2a}$)=$b^3$-$b^4$=as defined in claim 1;
   d) reacting an intermediate of formula (VI) with an intermediate of formula (VIII) in an appropriate solvent under a reaction-inert atmosphere in the presence of a suitable base

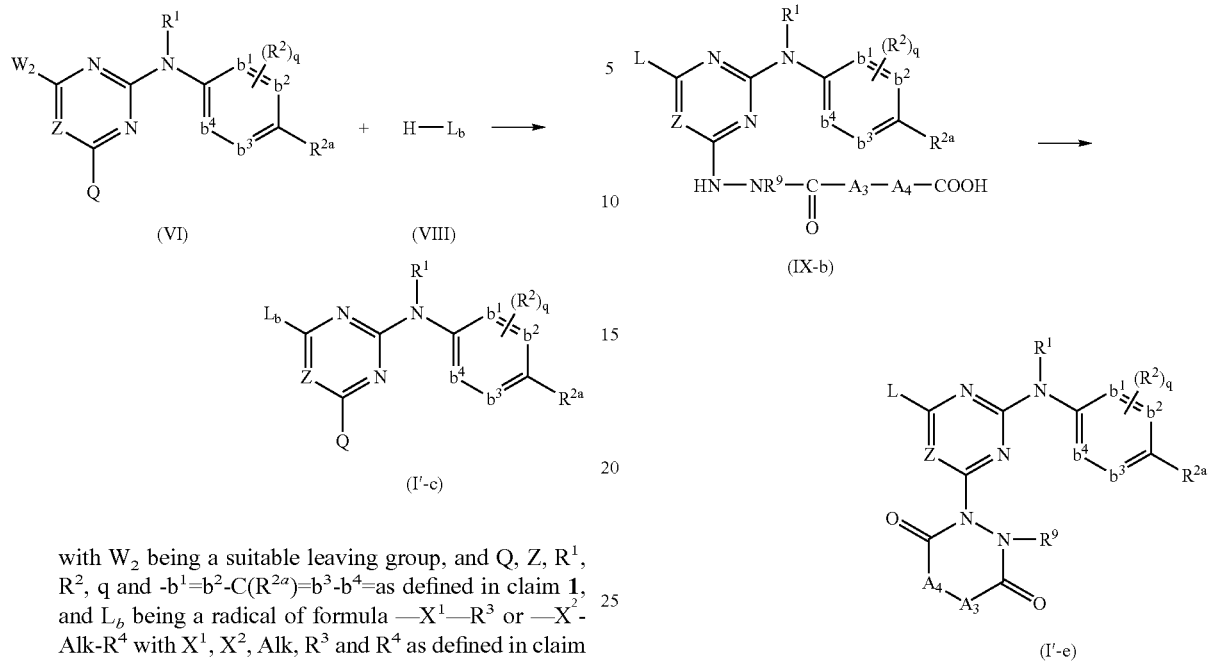

with $W_2$ being a suitable leaving group, and Q, Z, $R^1$, $R^2$, q and $-b^1=b^2-C(R^{2a})=b^3-b^4=$ as defined in claim 1, and $L_b$ being a radical of formula $-X^1-R^3$ or $-X^2-Alk-R^4$ with $X^1$, $X^2$, Alk, $R^3$ and $R^4$ as defined in claim 1;

e) reacting an intermediate of formula (IX-a) with an intermediate of formula (X)

with $W_3$ being a suitable leaving group and L, Z, $R^1$, $R^2$, q, $A_2$ and $-b^1=b^2-C(R^{2a})=b^3-b^4=$ as defined in claim 1;

f) cyclizing an intermediate of formula (IX-b) in the presence of a suitable carbonic derivative and a suitable base

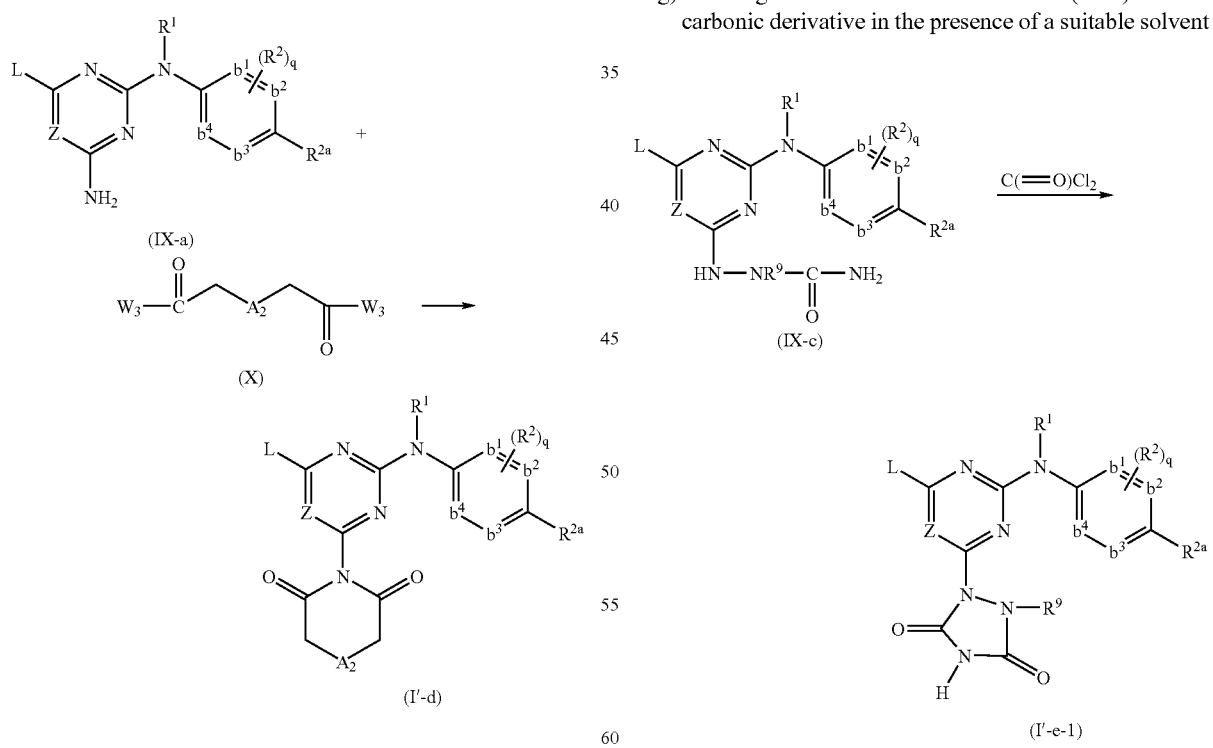

with L, Z, $R^1$, $R^2$, $R^9$, q, $A_3$, $A_4$ and $-b^1=b^2-C(R^{2a})=b^3-b^4=$ as defined in claim 1;

g) reacting an intermediate of formula (IX-c) with a carbonic derivative in the presence of a suitable solvent with L, Z, $R^1$, $R^2$, $R^9$, q, and $-b^1=b^2-C(R^{2a})=b^3-b^4=$ as defined in claim 1;

h) reacting an intermediate of formula (IX-d) with $W_4-CH_2-CH_2-C(=O)-W_4$ in the presence of a suitable base and a suitable solvent

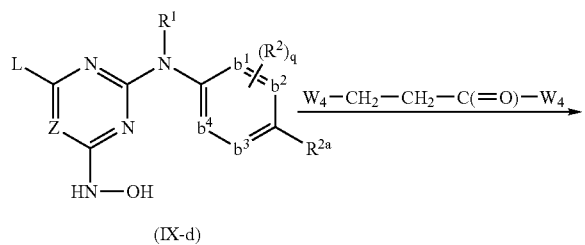

(IX-d)

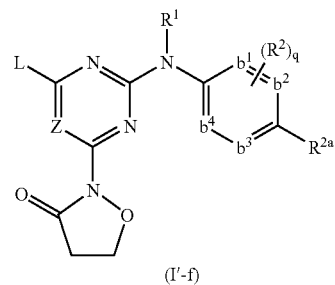

(I'-f)

with $W_4$ being a suitable leaving group and L, Z, $R^1$, $R^2$, q, and $-b^1=b^2-C(R^{2a})=b^3-b^4=$ as defined in claim 1;

i) reacting an intermediate of formula (XXIII) with an intermediate of formula (XXIV) and (XXV) in the presence of a suitable base and a suitable solvent

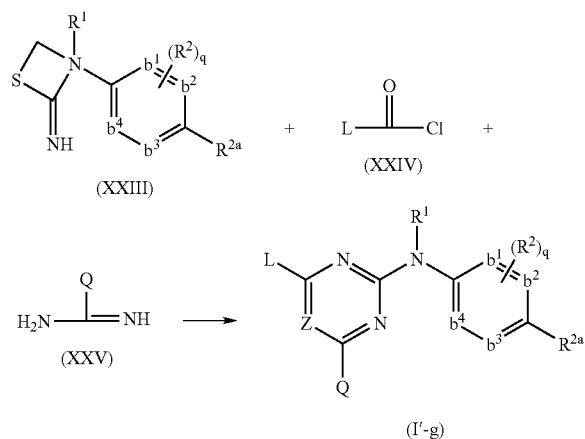

with L, Q, $R^1$, $R^2$, q, and $-b^1=b^2-C(R^{2a})=b^3-b^4=$ as defined in claim 1.

13. A process as recited in claim 12, further comprising converting compounds of formula (I) into a therapeutically active non-toxic acid addition salt by treatment with an acid.

14. A process as recited in claim 12, further comprising converting compounds of formula (I) into a therapeutically active non-toxic acid addition salt and converting the acid addition salt form into a free base by treatment with alkali.

15. A process as recited in claim 12, further comprising preparing at least one of stereochemically isomeric forms, N-oxide forms, and quaternary amines thereof.

16. A pharmaceutical composition comprising a pharmaceutically acceptable carrier and as active ingredient a therapeutically effective amount of a compound as claimed in claim 1.

17. A process for preparing a pharmaceutical composition comprising: providing a therapeutically effective amount of a compound as claimed in claim 1, and intimately mixing said therapeutically effective amount of the compound with a pharmaceutically acceptable carrier.

18. A product containing (a) a compound as claimed in claim 1, and (b) another antiretroviral compound, as a combined preparation for simultaneous, separate or sequential use in the treatment of HIV-1 infection.

19. A pharmaceutical composition for use in the treatment of HIV-1 infection comprising a pharmaceutically acceptable carrier and as active ingredients (a) a compound as claimed in claim 1, and (b) another antiretroviral compound, as a combined preparation.

20. A pharmaceutical composition comprising a pharmaceutically acceptable carrier and as active ingredient a therapeutically effective amount of a compound as claimed in claim 4.

21. A pharmaceutical composition comprising a pharmaceutically acceptable carrier and as active ingredient a therapeutically effective amount of a compound as claimed in claim 2.

22. A pharmaceutical composition comprising a pharmaceutically acceptable carrier and as active ingredient a therapeutically effective amount of a compound as claimed in claim 7.

23. A pharmaceutical composition comprising a pharmaceutically acceptable carrier and as active ingredient a therapeutically effective amount of a compound as claimed in claim 11.

24. A process for preparing a pharmaceutical composition as claimed in claim 19 comprising: providing a therapeutically effective amount of a compound having the formula

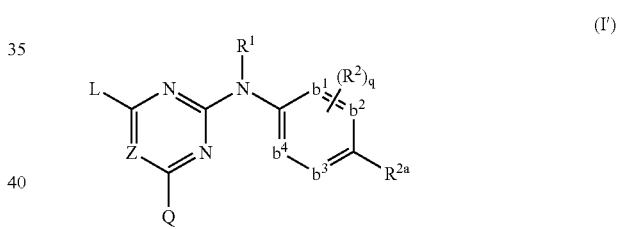

(I')

a N-oxide, a pharmaceutically acceptable addition salt, a quaternary amine and a stereochemically isomeric form thereof, wherein $-b^1=b^2-C(R^{2a})=b^3-b^4=$ represents a bivalent radical of formula $-CH=CH-C(R^{2a})=CH-CH=$ (b-1);

q is 0, 1, 2; or where possible q is 3 or 4;

$R^1$ is hydrogen; aryl; formyl; $C_{1-6}$alkylcarbonyl; $C_{1-6}$alkyl; $C_{1-6}$alkyloxycarbonyl;

1$C_{1-6}$alkyl substituted with formyl, $C_{1-6}$alkylcarbonyl, $C_{1-6}$alkyloxycarbonyl, $C_{1-6}$alkylcarbonyloxy; $C_{1-6}$alkyloxy$C_{1-6}$alkyloxycarbonyl substituted with $C_{1-6}$alkyloxycarbonyl;

L is $C_{1-10}$alkyl, $C_{2-10}$alkenyl, $C_{2-10}$alkynyl, $C_{3-7}$cycloalkyl, whereby each of said groups may be substituted with one or two substituents independently selected from $C_{3-7}$cycloalkyl, indolyl or isoindolyl, each optionally subsituted with one, two, three or four substituents each independently selected from halo, $C_{1-6}$alkyl, hydroxy, $C_{1-6}$alkyloxy, cyano, aminocarbonyl, nitro, amino, polyhalomethyl, polyhalomethyloxy and $C_{1-6}$alkylcarbonyl, phenyl, pyridyl, pyrimidinyl, pyrazinyl or pyridazinyl, wherein each of said aromatic rings may optionally be substituted with one, two, three, four or five substituents each independently selected from the substituents defined in $R^2$; or L is -$X^1$-$R^3$ or —$X^2$-Alk-$R^4$ wherein
  Alk is $C_{1-4}$alkanediyl;
  $R^3$ or $R^4$ each independently are phenyl, pyridyl, pyrimidinyl, pyrazinyl or pyridazinyl, wherein each of said aromatic rings may optionally be substituted with one, two, three, four or five substituents each independently selected from the substituents defined in $R^2$; and
  $X^1$ or $X^2$ each independently are —$NR^7$—, —NH—NH—, —N=N—, —O—, —C(=O)—, —CHOH—, —S—, —S(=O)$_p$—, O represents cyano, hydroxy, mercapto, carboxyl, formyl, cyano$C_{1-6}$alkyl, hydroxy$C_{1-6}$alkyl, mercapto$C_{1-6}$alkyl, amino$C_{1-6}$alkyl, mono- or di($C_{1-4}$alkyl)-amino$C_{1-6}$alkyl, aminocarbonyl, mono- or di($C_{1-4}$alkyl)aminocarbonyl, $C_{1-6}$alkyloxy, $C_{1-6}$alkylthio, $C_{1-6}$alkylS(=O)$_p$, $C_{1-6}$alkylcarbonyl, $C_{1-6}$alkylcarbonyloxy, $C_{1-6}$alkyloxycarbonyl, $C_{1-6}$alkylcarbonyloxy$C_{1-6}$alkyl, $C_{2-6}$alkenyl, $C_{2-6}$alkenyloxyamino, $R^5$-C(=O)—$C_{1-6}$alkyloxyamino, $C_{2-6}$alkynyl, polyhalo$C_{1-6}$alkyl, hydroxypolyhalo$C_{1-6}$alkyl, Het or $C_{1-6}$alkyloxy$C_{1-6}$alkyl wherein each hydrogen atom may optionally be substituted with $C_{1-6}$alkyloxy;

Z is C-Y wherein

Y represents hydrogen, hydroxy, halo, $C_{1-6}$alkyl, $C_{3-7}$cycloalkyl, $C_{2-6}$alkenyl optionally substituted with one or more halogen atoms, $C_{2-6}$alkynyl optionally substituted with one or more halogen atoms, $C_{1-6}$alkyl substituted with cyano or —C(=O)$R^8$, $C_{1-6}$akyloxy, $C_{1-6}$alkyloxycarbonyl, carboxyl, cyano, nitro, amino, mono- or di($C_{1-6}$alkyl)amino, polyhalomethyl, polyhalomethyloxy, polyhalomethylthio, —S(=O)$_p$$R^8$, —NH—S(=O)$_p$$R^8$, —C(=O)$R^8$, —NHC(=O)H, —C(=O)NHNH$_2$, —NHC(=O)$R^8$, —C(=NH)$R^8$ or aryl;

$R^5$ is hydrogen or a radical of formula

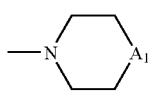

(d)

with
  $A_1$ in (d) being CH$_2$ or O;
  $R^6$ is methyl, amino, mono- or dimethylamino or polyhalomethyl;
  $R^7$ is hydrogen; aryl; formyl; $C_{1-6}$alkylcarbonyl; $C_{1-6}$alkyl; $C_{1-6}$alkyloxycarbonyl;
  $C_{1-6}$alkyl substituted with formyl, $C_{1-6}$alkylcarbonyl, $C_{1-6}$alkyloxycarbonyl, $C_{1-6}$alkylcarbonyloxy; $C_{1-6}$alkyloxy$C_{1-6}$alkylcarbonyl substituted with $C_{1-6}$alkyloxycarbonyl;
  $R^8$ is methyl, amino, mono- or dimethylamino or polyhalomethyl;
  p is 1 or 2;
  aryl is phenyl or phenyl substituted with one, two, three, four or five substituents each independently selected from halo, $C_{1-6}$alkyl, $C_{3-7}$cycloalkyl, $C_{1-6}$alkyloxy, cyano, nitro, polyhalo$C_{1-6}$alkyl, polyhalo$C_{1-6}$alkyloxy, aminocarbonyl, tetrazolyl;
  Het is imidazolyl, thiazolyl, oxazolyl, pyrazolyl, isothiazolyl, isoxazolyl, triazolyl, tetrazolyl optionally substituted with imino, a radical of formula (c) as described hereinabove, imidazolidinyl, pyrazolidinyl, thiazolidinyl, isothiazolidinyl, oxazolidinyl, isoxazolidinyl optionally substituted with hydroxy, isoxazolidinone, or a radical of formula

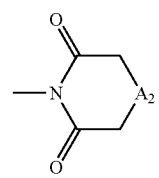

(e-1)

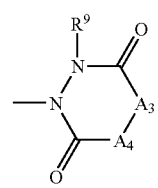

(e-2)

with
  $A_2$ in (e-1) being O, CH$_2$ or a direct bond;
  $A_3$ being CH$_2$ or NH;
  $A_4$ being CH$_2$ or a direct bond; or
  $A_3$-$A_4$ representing CH=CH;
  $R^9$ being hydrogen or $C_{1-4}$alkylcarbonyl;

provided that when O is polyhalo$C_{1-6}$alkyl then Y is hydrogen or $C_{1-6}$alkyl;

$R^{2a}$ is cyano, aminocarbonyl, mono- or di(methyl)aminocarbonyl, $C_{1-6}$alkyl substituted with cyano, aminocarbonyl or mono- or di(methyl)aminocarbonyl, $C_{2-6}$alkenyl substituted with cyano, or $C_{2-6}$alkylnyl substituted with cyano;
  each $R^2$ independently is hydroxy, halo, $C_{1-6}$alkyl optionally substituted with cyano or —C(=O)$R^6$, $C_{3-7}$cycloalkyl, $C_{2-6}$alkenyl optionally substituted with one or more halogen atoms or cyano, $C_{2-6}$alkynyl optionally substituted with one or more halogen atoms or cyano, $C_{1-6}$alkyloxy, $C_{1-6}$alkyloxycarbonyl, carboxyl, cyano, nitro, amino, mono- or di($C_{1-6}$alkyl)amino, polyhalomethyl, polyhalomethyloxy, polyhalomethylthio, —S(=O)$_p$$R^6$, —NH—S(=O)$_p$$R^6$, —C(=O)$R^6$, —NHC(=O)H, —C(=O)NHNH$_2$, —NHC(=O)$R^6$, —C(=NH)$R^6$ or a radical of formula

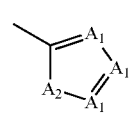

(c)

wherein each
  $A_1$ in (c) independently is N, CH or CR$^6$,
  $A_2$ in (c) is NH, O, S or NR$^6$;
  p is 1 or 2 and intimately mixing said therapeutically effective amount of the compound with a pharmaceutically acceptable carrier.

25. A process for preparing a pharmaceutical composition as claimed in claim 20 comprising: providing a therapeutically effective amount of a compound having the formula

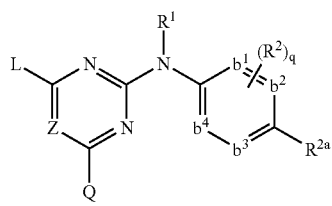
(I')

a N-oxide, a pharmaceutically acceptable addition salt, a quaternary amine and a stereochemically isomeric form thereof, wherein —$b^1$=$b^2$—C($R^{2a}$)=$b^3$-$b^4$=represents a bivalent radical of formula

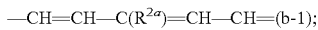
—CH=CH—C($R^{2a}$)=CH—CH=(b-1);

q is 0, 1, 2; or where possible q is 3 or 4;

$R^1$ is hydrogen; aryl; formyl; $C_{1-6}$alkylcarbonyl; $C_{1-6}$alkyl; $C_{1-6}$alkyloxycarbonyl; $C_{1-6}$alkyl substituted with formyl, $C_{1-6}$alkylcarbonyl, $C_{1-6}$alkyloxycarbonyl, $C_{1-6}$alkylcarbonyloxy; $C_{1-6}$alkyloxy$C_{1-6}$alkyloxycarbonyl substituted with $C_{1-6}$alkyloxycarbonyl;

wherein L is —$X^1$-$R^3$ is 2,4,6-trisubstituted phenyl, wherein $R^3$ is phenyl, pyridyl, pyrimidinyl, pyrazinyl or pyridazinyl, wherein each of said aromatic rings may optionally be substituted with one, two, three, four or five substituents each independently selected from the substituents defined in $R^2$; and $X^1$ is —$NR^7$—, —NH—NH—, —N=N—, —O—, —C(=O)—, —CHOH—, —S—, —S(=O)$_p$—;

wherein Q is cyano, hydroxy, mercapto, carboxyl, hydroxy$C_{1-6}$alkyl, mono- or di($C_{1-4}$alkyl)amino$C_{1-6}$alkyl, aminocarbonyl, $C_{1-6}$alkyloxy$C_{1-6}$alkyl wherein each hydrogen atom may optionally be substituted with $C_{1-6}$alkyloxy, $C_{1-6}$alkyloxy, $C_{1-6}$alkylthio, $C_{1-6}$alkylS(=O), $C_{1-6}$alkyloxycarbonyl, polyhalo$C_{1-6}$alkyl, $C_{2-6}$alkenyloxyamino, $R^5$—C(=O)—$C_{1-6}$alkyloxyamino, a radical of formula (c) or e-1) or (e-2), imidazolyl, traizolyl, tetrazolyl optionally substituted with imino, isoxazolidinyl optionally substituted with hydroxy, isoxazolidinone;

Z is C-Y wherein

Y represents hydrogen, hydroxy, halo, $C_{1-6}$alkyl, $C_{3-7}$cycloalkyl, $C_{2-6}$alkenyl optionally substituted with one or more halogen atoms, $C_{2-6}$alkynyl optionally substituted with one or more halogen atoms, $C_{1-6}$alkyl substituted with cyano or —C(=O)$R^8$, $C_{1-6}$akyloxy, $C_{1-6}$alkyloxycarbonyl, carboxyl, cyano, nitro, amino, mono- or di($C_{1-6}$alkyl)amino, polyhalomethyl, polyhalomethyloxy, polyhalomethylthio, —S(=O)$_p R^8$, —NH—S(=O)$_p R^8$, —C(=O)$R^8$, —NHC(=O)H, —C(=O)NHNH$_2$, —NHC(=O)$R^8$, —C(=NH)$R^8$ or aryl;

$R^5$ is hydrogen or a radical of formula

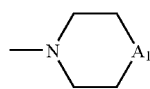
(d)

with $A_1$ in (d) being CH$_2$ or O;

$R^6$ is methyl, amino, mono- or dimethylamino or polyhalomethyl;

$R^7$ is hydrogen; aryl; formyl; $C_{1-6}$alkylcarbonyl; $C_{1-6}$alkyl; $C_{1-6}$alkyloxycarbonyl;

$C_{1-6}$alkyl substituted with formyl, $C_{1-6}$alkylcarbonyl, $C_{1-6}$alkyloxycarbonyl, $C_{1-6}$alkylcarbonyloxy; $C_{1-6}$alkyloxy$C_{1-6}$alkylcarbonyl substituted with $C_{1-6}$alkyloxycarbonyl;

$R^8$ is methyl, amino, mono- or dimethylamino or polyhalomethyl;

p is 1 or 2;

aryl is phenyl or phenyl substituted with one, two, three, four or five substituents each independently selected from halo, $C_{1-6}$alkyl, $C_{3-7}$cycloalkyl, $C_{1-6}$alkyloxy, cyano, nitro, polyhalo$C_{1-6}$alkyl, polyhalo$C_{1-6}$alkyloxy, aminocarbonyl, tetrazolyl;

Het is imidazolyl, thiazolyl, oxazolyl, pyrazolyl, isothiazolyl, isoxazolyl, triazolyl, tetrazolyl optionally substituted with imino, a radical of formula (c) as described hereinabove, imidazolidinyl, pyrazolidinyl, thiazolidinyl, isothiazolidinyl, oxazolidinyl, isoxazolidinyl optionally substituted with hydroxy, isoxazolidinone, or a radical of formula

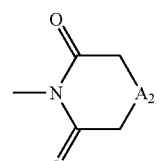
(e-1)

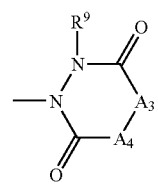
(e-2)

with $A_2$ in (e-1) being O, CH$_2$ or a direct bond;

$A_3$ being CH$_2$ or NH;

$A_4$ being CH$_2$ or a direct bond; or $A_3$-$A_4$ representing CH=CH;

$R^9$ being hydrogen or $C_{1-4}$alkylcarbonyl;

provided that when Q is polyhalo$C_{1-6}$alkyl then Y is hydrogen or $C_{1-6}$alkyl;

$R^{2a}$ is cyano, aminocarbonyl, mono- or di(methyl)aminocarbonyl, $C_{1-6}$alkyl substituted with cyano, aminocarbonyl or mono- or di(methyl)aminocarbonyl, $C_{2-6}$alkenyl substituted with cyano, or $C_{2-6}$alkylnyl substituted with cyano;

each $R^2$ independently is hydroxy, halo, $C_{1-6}$alkyl optionally substituted with cyano or —C(=O)$R^6$, $C_{3-7}$cycloalkyl, $C_{2-6}$alkenyl optionally substituted with one or more halogen atoms or cyano, $C_{2-6}$alkynyl optionally substituted with one or more halogen atoms or cyano, $C_{1-6}$alkyloxy, $C_{1-6}$alkyloxycarbonyl, carboxyl, cyano, nitro, amino, mono- or di($C_{1-6}$alkyl)amino, polyhalomethyl, polyhalomethyloxy, polyhalomethylthio, —S(=O)$_p R^6$, —NH—S(=O)$_p R^6$, —C(=O)$R^6$, —NHC(=O)H, —C(=O)NHNH$_2$, —NHC(=O)$R^6$, —C(=NH)$R^6$ or a radical of formula

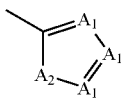

wherein each
- $A_1$ in (c) independently is N, CH or $CR^6$;
- $A_2$ in (c) is NH, O, S or $NR^6$;
- p is 1 or 2 and intimately mixing said therapeutically effective amount of the compound with a pharmaceutically acceptable carrier.

26. A process for preparing a pharmaceutical composition as claimed in claim 21 comprising: providing a therapeutically effective amount of a compound having the formula

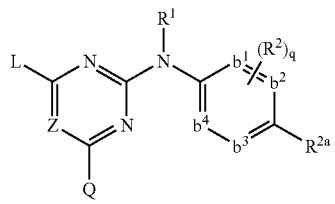

a N-oxide, a pharmaceutically acceptable addition salt, a quaternary amine and a stereochemically isomeric form thereof, wherein —$b^1$=$b^2$—$C(R^{2a})$=$b^3$-$b^4$=represents a bivalent radical of formula —CH=CH—C($R^{2a}$)=CH—CH= (b-1);

q is 0, 1, 2; or where possible q is 3 or 4;

$R^1$ is hydrogen; aryl; formyl; $C_{1-6}$alkylcarbonyl; $C_{1-6}$alkyl; $C_{1-6}$alkyloxycarbonyl; $C_{1-6}$alkyl substituted with formyl, $C_{1-6}$alkylcarbonyl, $C_{1-6}$alkyloxycarbonyl, $C_{1-6}$alkylcarbonyloxy; $C_{1-6}$alkyloxy$C_{1-6}$alkyloxycarbonyl substituted with $C_{1-6}$alkyloxycarbonyl;

L is $C_{1-10}$alkyl, $C_{2-10}$alkenyl, $C_{2-10}$alkynyl, $C_{3-7}$cycloalkyl, whereby each of said groups may be be substituted with one or two substituents independently selected from $C_{3-7}$cycloalkyl, indolyl or isoindolyl, each optionally substituted with one, two, three or four substituents each independently selected from halo, $C_{1-6}$alkyl, hydroxy, $C_{1-6}$alkyloxy, cyano, aminocarbonyl, nitro, amino, polyhalomethyl, polyhalomethyloxy and $C_{1-6}$alkylcrbonyl, phenyl, pyridyl, pyrimidinyl, pyrazinyl or pyridazinyl, wherein each of said aromatic rings may optionally be substituted with one, two, three, four or five substituents each independently selected from the substituents defined in $R^2$; or L is —$X^1$-$R^3$ or —$X^2$-Alk-$R^4$ wherein
Alk is $C_{1-4}$alkanediyl;
$R^3$ or $R^4$ each independently are phenyl, pyridyl, pyrimidinyl, pyrazinyl or pyridazinyl, wherein each of said aromatic rings may optionally be substituted with one, two, three or five substituents each independently selected from the substituents defined in $R^2$; and
$X^1$ or $X^2$ each independently are —$NR^7$—, —NH—NH—, —N=N—, —O—, —C(=O)—, —CHOH—, —S—, —S(=O)$_p$—;

wherein Q is cyano, hydroxy, mercapto, carboxyl, hydroxy$C_{1-6}$alkyl, mono- or di($C_{1-4}$alkyl)amino$C_{1-6}$alkyl, aminocarbonyl, $C_{1-6}$alkyloxy$C_{1-6}$alkyl wherein each hydrogen atom may optionally be substituted with $C_{1-6}$alkyloxy, $C_{1-6}$alkyloxy, $C_{1-6}$alkylthio, $C_{1-6}$alkylS(=O), $C_{1-6}$alkyloxycarbonyl, polyhalo$C_{1-6}$alkyl, $C_{2-6}$alkenyloxyamino, $R^5$—C(=O)—$C_{1-6}$alkyloxyamino, a radical of formula (c) or (e-1) or (e-2), imidazolyl, traizolyl, tetrazolyl optionally substituted with imino, isoxazolidinyl optionally substituted with hydroxy, isoxazolidinone;

Z is C-Y wherein
Y represents hydrogen, hydroxy, halo, $C_{1-6}$alkyl, $C_{3-7}$cycloalkyl, $C_{2-6}$alkenyl optionally substituted with one or more halogen atoms, $C_{2-6}$alkynyl optionally substituted with one or more halogen atoms, $C_{1-6}$alkyl substituted with cyano or —C(=O)$R^8$, $C_{1-6}$akyloxy, $C_{1-6}$alkyloxycarbonyl, carboxyl, cyano, nitro, amino, mono- or di($C_{1-6}$alkyl)amino, polyhalomethyl, polyhalomethyloxy, polyhalomethylthio, —S(=O)$_p$$R^8$, —NH—S(=O)$_p$$R^8$, —C(=O)$R^8$, —NHC(=O)H, —C(=O)NHNH$_2$, —NHC(=O)$R^8$, —C(=NH)$R^8$ or aryl;

$R^5$ is hydrogen or a radical of formula

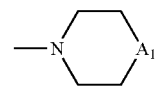

with
$A_1$ in (d) being $CH_2$ or O;
$R^6$ is methyl, amino, mono- or dimethylamino or polyhalomethyl;
$R^7$ is hydrogen; aryl; formyl; $C_{1-6}$alkylcarbonyl; $C_{1-6}$alkyl; $C_{1-6}$alkyloxycarbonyl; $C_{1-6}$alkyl substituted with formyl, $C_{1-6}$alkylcarbonyl, $C_{1-6}$alkyloxycarbonyl, $C_{1-6}$alkylcarbonyloxy; $C_{1-6}$alkyloxy$C_{1-6}$alkylcarbonyl substituted with $C_{1-6}$alkyloxycarbonyl;
$R^8$ is methyl, amino, mono- or dimethylamino or polyhalomethyl;
p is 1 or 2;
aryl is phenyl or phenyl substituted with one, two, three, four or five substituents each independently selected from halo, $C_{1-6}$alkyl, $C_{3-7}$cycloalkyl, $C_{1-6}$alkyloxy, cyano, nitro, polyhalo$C_{1-6}$alkyl, polyhalo$C_{1-6}$alkyloxy, aminocarbonyl, tetrazolyl;
Het is imidazolyl, thiazolyl, oxazolyl, pyrazolyl, isothiazolyl, isoxazolyl, triazolyl, tetrazolyl optionally substituted with imino, a radical of formula (c) as described hereinabove, imidazolidinyl, pyrazolidinyl, thiazolidinyl, isothiazolidinyl, oxazolidinyl, isoxazolidinyl optionally substituted with hydroxy, isoxazolidinone, or a radical of formula

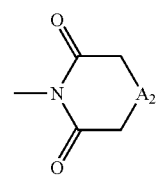

-continued

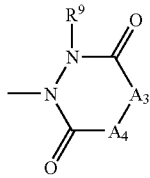
(e-2)

with
- $A_2$ in (e-1) being O, $CH_2$ or a direct bond;
- $A_3$ being $CH_2$ or NH;
- $A_4$ being $CH_2$ or a direct bond; or
- $A_3$-$A_4$ representing CH=CH;
- $R^9$ being hydrogen or $C_{1-4}$alkylcarbonyl;

provided that when O is polyhalo$C_{1-6}$alkyl then Y is hydrogen or $C_{1-6}$alkyl;

$R^{2a}$ is cyano, aminocarbonyl, mono- or di(methyl)aminocarbonyl, $C_{1-6}$alkyl substituted with cyano, aminocarbonyl or mono- or di(methyl)aminocarbonyl, $C_{2-6}$alkenyl substituted with cyano, or $C_{2-6}$alkynyl substituted with cyano;

each $R^2$ independently is hydroxy, halo, $C_{1-6}$alkyl optionally substituted with cyano or —C(=O)$R^6$, $C_{3-7}$cycloalkyl, $C_{2-6}$alkenyl optionally substituted with one or more halogen atoms or cyano, $C_{2-6}$alkynyl optionally substituted with one or more halogen atoms or cyano, $C_{1-6}$alkyloxy, $C_{1-6}$alkyloxycarbonyl, carboxyl, cyano, nitro, amino, mono- or di($C_{1-6}$alkyl)amino, polyhalomethyl, polyhalomethyloxy, polyhalomethylthio, —S(=O)$_p$$R^6$, —NH—S(=O)$_p$$R^6$, —C(=O)$R^6$, —NHC(=O)H, —C(=O)NHNH$_2$, —NHC(=O)$R^6$, —C(=NH)$R^6$ or a radical of formula

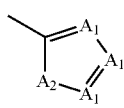
(c)

wherein each
- $A_1$ in (c) independently is N, CH or CR$^6$;
- $A_2$ in (c) is NH, O, S or NR$^6$;
- p is 1 or 2 and intimately mixing said therapeutically effective amount of the compound with a pharmaceutically acceptable carrier.

27. A process for preparing a pharmaceutical composition as claimed in claim 22 comprising: providing a therapeutically effective amount of a compound having the formula

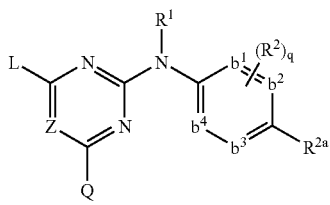
(I')

a N-oxide, a pharmaceutically acceptable addition salt, a quaternary amine and a stereochemically isomeric form thereof, wherein —$b^1$=$b^2$—C($R^{2a}$)=$b^3$—$b^4$= represents a bivalent radical of formula —CH=CH—C($R^{2a}$)=CH—CH= (b-1);

q is 0, 1, 2; or where possible q is 3 or 4;

$R^1$ is hydrogen; aryl; formyl; $C_{1-6}$alkylcarbonyl; $C_{1-6}$alkyl; $C_{1-6}$alkyloxycarbonyl; $C_{1-6}$alkyl substituted with formyl, $C_{1-6}$alkylcarbonyl, $C_{1-6}$alkyloxycarbonyl, $C_{1-6}$alkylcarbonyloxy; $C_{1-6}$alkyloxy$C_{1-6}$alkyloxycarbonyl substituted with $C_{1-6}$alkyloxycarbonyl;

wherein the moiety in the 2 position of the pyrimidine ring is a 4-cyano anilino group, L is —$Z^1R^3$ wherein $R^3$ is a 2,4,6-trisubstituted phenyl, Z is C—Y with Y being halo or hydrogen and Q is hydroxy$C_{1-6}$alkyl, $C_{1-6}$alkyloxy$C_{1-6}$alkyl, polyhalo$C_{1-6}$alkyl, aminocarbonyl, mono- or di($C_{1-4}$alkyl)aminocarbonyl, cyano or Het $R^3$ or $R^4$ each independently are phenyl, pyridyl, pyrimidinyl, pyrazinyl or pyridazinyl, wherein each of said aromatic rings may optionally be substituted with one, two, three, four or five substituents each independently selected from the substituents defined in $R^2$; and $X^1$ or $X^2$ each independently are —$NR^7$—, —NH—NH—, —N=N—, —O—, —C(=O)—, —CHOH—, —S—, —S(=O)$_p$—;

Q represents cyano, hydroxy, mercapto, carboxyl, formyl, cyano $C_{1-6}$alkyl, hydroxy$C_{1-6}$alkyl, mercapto$C_{1-6}$alkyl, amino$C_{1-6}$alkyl, mono- or di($C_{1-4}$alkyl)amino$C_{1-6}$alkyl, aminocarbonyl, mono- or di($C_{1-4}$alkyl)aminocarbonyl, $C_{1-6}$alkyloxy, $C_{1-6}$alkylthio, $C_{1-6}$alkylS(=O)$_p$, $C_{1-6}$alkylcarbonyl, $C_{1-6}$alkylcarbonyloxy, $C_{1-6}$alkyloxycarbonyl, $C_{1-6}$alkylcarbonyloxy$C_{1-6}$alkyl, $C_{2-6}$alkenyl, $C_{2-6}$alkenyloxyamino, $R^5$ —C(=O)-$C_{1-6}$alkyloxyamino, $C_{2-6}$alkynyl, polyhalo$C_{1-6}$alkyl, hydroxypolyhalo$C_{1-6}$alkyl, Het or $C_{1-6}$alkyloxy$C_{1-6}$alkyl wherein each hydrogen atom may optionally be substituted with $C_{1-6}$alkyloxy;

$R^5$ is hydrogen or a radical of formula

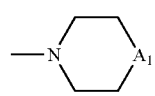
(d)

with
- $A_1$ in (d) being $CH_2$ or O;
- $R^6$ is methyl, amino, mono- or dimethylamino or polyhalomethyl;
- $R^7$ is hydrogen; aryl; formyl; $C_{1-6}$alkylcarbonyl; $C_{1-6}$alkyl; $C_{1-6}$alkyloxycarbonyl; $C_{1-6}$alkyl substituted with formyl, $C_{1-6}$alkylcarbonyl, $C_{1-6}$alkyloxycarbonyl, $C_{1-6}$alkylcarbonyloxy; $C_{1-6}$alkyloxy$C_{1-6}$alkylcarbonyl substituted with $C_{1-6}$alkyloxycarbonyl;
- $R^8$ is methyl, amino, mono- or dimethylamino or polyhalomethyl;
- p is 1 or 2;
- aryl is phenyl or phenyl substituted with one, two, three, four or five substituents each independently selected from halo, $C_{1-6}$alkyl, $C_{3-7}$cycloalkyl, $C_{1-6}$alkyloxy, cyano, nitro, polyhalo$C_{1-6}$alkyl, polyhalo$C_{1-6}$alkyloxy, aminocarbonyl, tetrazolyl;
- Het is imidazolyl, thiazolyl, oxazolyl, pyrazolyl, isothiazolyl, isoxazolyl, triazolyl, tetrazolyl optionally substituted with imino, a radical of formula (c) as described hereinabove, imidazolidinyl, pyrazolidinyl, thiazolidinyl, isothiazolidinyl, oxazolidinyl, isoxazolidinyl optionally substituted with hydroxy, isoxazolidinone, or a radical of formula

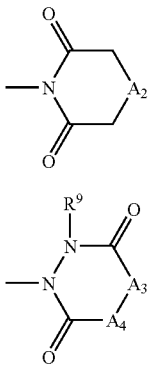

(e-1)

(e-2)

with
A$_2$ in (e-1) being O, CH$_2$ or a direct bond;
A$_3$ being CH$_2$ or NH;
A$_4$ being CH$_2$ or a direct bond; or
A$_3$-A$_4$ representing CH=CH;
R$^9$ being hydrogen or C$_{1-4}$alkylcarbonyl;
R$^{2a}$ is cyano, aminocarbonyl, mono- or di(methyl)aminocarbonyl, C$_{1-6}$alkyl substituted with cyano, aminocarbonyl or mono- or di(methyl)aminocarbonyl, C$_{2-6}$alkenyl substituted with cyano, or C$_{2-6}$alkylnyl substituted with cyano;
each R$^2$ independently is hydroxy, halo, C$_{1-6}$alkyl optionally substituted with cyano or —C(=O)R$^6$, C$_{3-7}$cycloalkyl, C$_{2-6}$alkenyl optionally substituted with one or more halogen atoms or cyano, C$_{2-6}$alkynyl optionally substituted with one or more halogen atoms or cyano, C$_{1-6}$alkyloxy, C$_{1-6}$alkyloxycarbonyl, carboxyl, cyano, nitro, amino, mono- or di(C$_{1-6}$alkyl)amino, polyhalomethyl, polyhalomethyloxy, polyhalomethylthio, —S(=O)$_p$R$^6$, —NH—S(=O)$_p$R$^6$, —C(=O)R$^6$, —NHC(=O)H, —C(=O)NHNH$_2$, —NHC(=O)R$^6$, —C(=NH)R$^6$ or a radical of formula

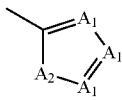

(c)

wherein each
A$_1$ in (c) independently is N, CH or CR$^6$;
A$_2$ in (c) is NH, O, S or NR$^6$;
p is 1 or 2 and intimately mixing said therapeutically effective amount of the compound with a pharmaceutically acceptable carrier.

28. A process for preparing a pharmaceutical composition as claimed in claim 23 comprising: providing a therapeutically effective amount of a compound selected from the group consisting of:
4[[[5-bromo-4-(4-cyano-2,6-dimethylphenoxy)-6-hydroxymethyl]-2-pyrimidinyl]amino]benzonitrile;
4-[[[6-trifluoromethyl-2-(4-cyanophenylamino)]-4-pyrimidinyl]amino]-3,5-dimethylbenzonitrile;
4-[[[5-bromo-4-(4-cyano-2,6-dimethylphenoxy)-6-methoxymethyl]-2pyrimidinyl]amino]benzonitrile;
4-[[[5-bromo-4-(4-cyano-2,6-dibromophenoxy)-6-hydroxymethyl]2-pyrimidinyl]amino]benzonitrile;
2-[(4-cyanophenyl)amino]-6-[(2,4,6-trimethylphenyl) amino]-4-pyrimidine carboxyamide;
5-bromo-2-[(4-cyanophenyl)amino]-6-[(2,4,6-trimethylphenyl)amino]-4-pyrimidine carboxamide;
and N-oxide, pharmaceutically acceptable addition salts, quaternary amine and stereochemically isomeric forms thereof,
and intimately mixing said therapeutically effective amount of the compound with a pharmaceutically acceptable carrier.

29. A product containing (a) a compound as claimed in claim 2, and (b) another antiretroviral compound, as a combined preparation for simultaneous, separate or sequential use in the treatment of HIV-1 infection.

30. A product containing (a) a compound as claimed in claim 3, and (b) another antiretroviral compound, as a combined preparation for simultaneous, separate or sequential use in the treatment of HIV-1 infection.

31. A product containing (a) a compound as claimed in claim 4, and (b) another antiretroviral compound, as a combined preparation for simultaneous, separate or sequential use in the treatment of HIV-1 infection.

32. A product containing (a) a compound as claimed in claim 5, and (b) another antiretroviral compound, as separate preparations for simultaneous, separate or sequential use in the treatment of HIV-1 infection.

33. A product containing (a) a compound as claimed in claim 6, and (b) another antiretroviral compound, as a combined preparation for simultaneous, separate or sequential use in the treatment of HIV-1 infection.

34. A product containing (a) a compound as claimed in claim 7, and (b) another antiretroviral compound, as a combined preparation for simultaneous, separate or sequential use in the treatment of HIV-1infection.

35. A product containing (a) a compound as claimed in claim 8, and (b) another antiretroviral compound, as a combined preparation for simultaneous, separate or sequential use in the treatment of HIV-1 infection.

36. A product containing (a) a compound as claimed in claim 11, and (b) another antiretroviral compound, as a combined preparation for simultaneous, separate or sequential use in the treatment of HIV-1 infection.

37. A pharmaceutical composition for use in treatment of HIV-1 infection comprising a pharmaceutically acceptable carrier and as active ingredients (a) a compound as claimed in claim 2, and (b) another antiretroviral compound, as a combined preparation.

38. A pharmaceutical composition for use in treatment of HIV-1 infection comprising a pharmaceutically acceptable carrier and as active ingredients (a) a compound as claimed in claim 3, and (b) another antiretroviral compound, as a combined preparation.

39. A pharmaceutical composition for use in treatment of HIV-1 infection comprising a pharmaceutically acceptable carrier and as active ingredients (a) a compound as claimed in claim 4, and (b) another antiretroviral compound, as a combined preparation.

40. A pharmaceutical composition for use in treatment of HIV-1 infection comprising a pharmaceutically acceptable carrier and as active ingredients (a) a compound as claimed in claim 5, and (b) another antiretroviral compound, as a combined preparation.

41. A pharmaceutical composition for use in treatment of HIV-1 infection comprising a pharmaceutically acceptable carrier and as active ingredients (a) a compound as claimed in claim 6, and (b) another antiretroviral compound, as a combined preparation.

42. A pharmaceutical composition for use in treatment of HIV-1 infection comprising a pharmaceutically acceptable carrier and as active ingredients (a) a compound as claimed in claim 7, and (b) another antiretroviral compound, as a combined preparation.

43. A pharmaceutical composition for use in treatment of HIV-1 infection comprising a pharmaceutically acceptable carrier and as active ingredients (a) a compound as claimed in claim 8, and (b) another antiretroviral compound, as a combined preparation.

44. A pharmaceutical composition for use in treatment of HIV-1 infection comprising a pharmaceutically acceptable carrier and as active ingredients (a) a compound as claimed in claim 11, and (b) another antiretroviral compound, as a combined preparation.

45. A method for the treatment of HIV-1 infection, comprising: providing an active ingredient, and administering an effective amount of a composition comprising said active ingredient to a human being in need thereof wherein said active ingredient comprises a compound as claimed in claim 1.

46. A method for the treatment of HIV-1 infection, comprising: providing an active ingredient, and administering an effective amount of a composition comprising said active ingredient to a human being in need thereof wherein said active ingredient comprises a compound as claimed in claim 4.

47. A method for the treatment of HIV-1 infection, comprising: providing an active ingredient, and administering an effective amount of a composition comprising said active ingredient to a human being in need thereof wherein said active ingredient comprises a compound as claimed in claim 2.

48. A method for the treatment of HIV-1 infection, comprising: providing an active ingredient, and administering an effective amount of a composition comprising said active ingredient to a human being in need thereof wherein said active ingredient comprises a compound as claimed in claim 7.

49. A method for the treatment of HIV-1 infection, comprising: providing an active ingredient, and administering an effective amount of a composition comprising said active ingredient to a human being in need thereof wherein said active ingredient comprises a compound as claimed in claim 11.

* * * * *